United States Patent
Dimoudis et al.

(10) Patent No.: US 9,663,580 B2
(45) Date of Patent: May 30, 2017

(54) ANTIBODIES AGAINST HUMAN CSF-1R AND USES THEREOF

(71) Applicant: HOFFMANN-LA ROCHE INC., Little Falls, NJ (US)

(72) Inventors: Nikolaos Dimoudis, Wielenbach (DE); Georg Fertig, Penzberg (DE); Alexander Fidler, Penzberg (DE); Klaus Kaluza, Weilheim (DE); Marlene Thomas, Penzberg (DE); Carola Ries, Penzberg (DE); Stefan Seeber, Penzberg (DE); Martin Lanzendoerfer, Tutzing (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 15/292,710

(22) Filed: Oct. 13, 2016

(65) Prior Publication Data
US 2017/0029517 A1 Feb. 2, 2017

Related U.S. Application Data

(62) Division of application No. 14/640,183, filed on Mar. 6, 2015, now Pat. No. 9,499,625, which is a division of application No. 12/962,445, filed on Dec. 7, 2010, now Pat. No. 8,999,327.

(30) Foreign Application Priority Data

Dec. 10, 2009 (EP) .................... 09015310
Aug. 19, 2010 (EP) .................... 10173407

(51) Int. Cl.
*C07K 16/00* (2006.01)
*C07K 16/28* (2006.01)
*A61K 39/00* (2006.01)

(52) U.S. Cl.
CPC .... *C07K 16/2866* (2013.01); *A61K 2039/505* (2013.01); *C07K 2317/21* (2013.01); *C07K 2317/24* (2013.01); *C07K 2317/31* (2013.01); *C07K 2317/56* (2013.01); *C07K 2317/565* (2013.01); *C07K 2317/567* (2013.01); *C07K 2317/622* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,202,238 A | 4/1993 | Fell, Jr. et al. | |
| 5,204,244 A | 4/1993 | Fell et al. | |
| 5,208,020 A | 5/1993 | Chari et al. | |
| 5,416,064 A | 5/1995 | Chari et al. | |
| 5,635,483 A | 6/1997 | Pettit et al. | |
| 5,712,374 A | 1/1998 | Kuntsmann et al. | |
| 5,714,586 A | 2/1998 | Kunstmann et al. | |
| 5,739,116 A | 4/1998 | Hamann et al. | |
| 5,767,285 A | 6/1998 | Hamann et al. | |
| 5,770,710 A | 6/1998 | McGahren et al. | |
| 5,773,001 A | 6/1998 | Hamann et al. | |
| 5,780,588 A | 7/1998 | Pettit et al. | |
| 5,866,114 A | 2/1999 | Pandit et al. | |
| 5,877,296 A | 3/1999 | Hamann et al. | |
| 6,184,354 B1 | 2/2001 | Koths et al. | |
| 6,630,579 B2 | 10/2003 | Chari et al. | |
| 7,108,852 B2 | 9/2006 | Devalaraja et al. | |
| 7,498,298 B2 | 3/2009 | Doronina et al. | |
| 8,182,813 B2 * | 5/2012 | Brasel ................ | C07K 16/2866 424/139.1 |
| 8,470,977 B2 | 6/2013 | Haegel et al. | |
| 8,604,170 B2 | 12/2013 | Haegel et al. | |
| 8,999,327 B2 | 4/2015 | Dimoudis et al. | |
| 9,169,323 B2 | 10/2015 | Fertig et al. | |
| 9,192,667 B2 | 11/2015 | Hoves et al. | |
| 9,221,910 B2 | 12/2015 | Fertig et al. | |
| 2011/0081353 A1 | 4/2011 | Haegel et al. | |
| 2011/0178278 A1 | 7/2011 | Haegel et al. | |
| 2011/0274683 A1 | 11/2011 | Wong et al. | |
| 2013/0289250 A1 | 10/2013 | Haegel et al. | |
| 2014/0057972 A1 | 2/2014 | Haegel et al. | |
| 2014/0079706 A1 | 3/2014 | Cannarile et al. | |
| 2014/0336363 A1 | 11/2014 | Fertig et al. | |
| 2015/0073129 A1 | 3/2015 | Herting et al. | |
| 2015/0080556 A1 | 3/2015 | Fertig et al. | |

(Continued)

FOREIGN PATENT DOCUMENTS

| EP | 0307434 B2 | 3/1989 |
|---|---|---|
| EP | 0668914 B1 | 8/1995 |

(Continued)

OTHER PUBLICATIONS

Abu-Duhier et al., "Mutational analysis of class III receptor tyrosine kinases (C-KIT, C-FMS, FLT3) in idiopathic myelofibrosis," Br J Haematol. 120{3}:464-470 (2003).
Affymetrix Ebioscience. (2000-2014). "Anti-Mouse CD115 (c-fms) Purified," located at <http://www.ebioscience.com/mouse-cd115-antibody-purified-afs98.htm>, last visited on Mar. 26, 2015, one page.
Aharinejad et al., "Colony-stimulating factor-1 blockade by antisense oligonucleotides and small interfering RNAs suppresses growth of human mammary tumor xenografts in mice," CancerRes. 64(15):5378-5384(2004).
Anonymous (1988). "MCSF Receptor antibody (ab 10676)" 38 pages.
Ashmun et al., "Monoclonal antibodies to the human CSF-1 receptor (c-fms proto-oncogene product) detect epitopes on normal mononuclear phagocytes and on human myeloid leukemic blast cells" Blood 73(3):827-37 (Feb. 15, 1989).
Baker et al., "Expression of the colony-stimulating factor 1 receptor in B lymphocytes," Oncogene. 8(2):371-378 (1993).

(Continued)

*Primary Examiner* — Laura B Goddard
*Assistant Examiner* — Meera Natarajan
(74) *Attorney, Agent, or Firm* — Morrison & Foerster LLP

(57) ABSTRACT

The present invention relates to antibodies against human CSF-1R (anti-CSF-1R antibody), methods for their production, pharmaceutical compositions containing said antibodies, and uses thereof.

20 Claims, 10 Drawing Sheets

(56) References Cited

U.S. PATENT DOCUMENTS

| | | | |
|---|---|---|---|
| 2015/0158950 A1 | 6/2015 | Dimoudis et al. |
| 2015/0175696 A1 | 6/2015 | Fertig et al. |
| 2015/0274830 A1 | 10/2015 | Dimoudis et al. |
| 2015/0274831 A1 | 10/2015 | Dimoudis et al. |
| 2016/0053015 A1 | 2/2016 | Fertig et al. |
| 2016/0220669 A1 | 8/2016 | Hoves et al. |
| 2017/0015752 A1 | 1/2017 | Fertig et al. |

FOREIGN PATENT DOCUMENTS

| | | | |
|---|---|---|---|
| EP | 0425235 B1 | 9/1996 |
| EP | 2423228 A1 | 2/2012 |
| JP | H0967400 A | 3/1997 |
| RU | 2008132150 A | 2/2010 |
| WO | WO-93/25687 A1 | 12/1993 |
| WO | WO-94/11026 A2 | 5/1994 |
| WO | WO-98/52976 A1 | 11/1998 |
| WO | WO-99/17798 A1 | 4/1999 |
| WO | WO-01/30381 A2 | 5/2001 |
| WO | WO-2004/045532 A2 | 6/2004 |
| WO | WO-2005/046657 A2 | 5/2005 |
| WO | WO-2006/012451 A2 | 2/2006 |
| WO | WO-2006/096489 A2 | 9/2006 |
| WO | WO-2007/075326 A2 | 7/2007 |
| WO | WO-2007081879 A2 | 7/2007 |
| WO | WO-2009/026303 A1 | 2/2009 |
| WO | WO-2009/112245 A1 | 9/2009 |
| WO | WO-2011/070024 A1 | 6/2011 |
| WO | WO-2011/107553 A1 | 9/2011 |
| WO | WO-2011/117329 A1 | 9/2011 |
| WO | WO-2011/123381 A1 | 10/2011 |
| WO | WO-2011/131407 A1 | 10/2011 |
| WO | WO-2011/140249 A2 | 11/2011 |
| WO | WO-2013/087699 A1 | 6/2013 |
| WO | WO-2013/132044 A1 | 9/2013 |
| WO | WO-2014/173814 A1 | 10/2014 |
| WO | WO-2015/036511 A1 | 3/2015 |

OTHER PUBLICATIONS

Balkwill et al., "Smoldering and polarized inflammation in the initiation and promotion of malignant disease," Cancer Cell. 7(3):211-217 (2005).
Balkwill, "TNF-alpha in promotion and progression of cancer," Cancer Metastasis Rev. 25(3):409-416 (2006).
Barnes et al., "Advances in animal cell recombinant protein production: GS-NSO expression system," Cytotechnology. 32(2): 109-123 (2000).
Barnes et al., "Characterization of the stability of recombinant protein production in the GS-NSO expression system," Biotechnol Bioeng. 73(4):261-270 (2001).
Beiboer et al., "Guided selection of a pan carcinoma specific antibody reveals similar binding characteristics yet structural divergence between the original murine antibody and its human equivalent," J Mol Biol. 296(3):833-849 (2000).
Bingle et al., The role of tumour-associated macrophages in tumour progression: implications for new anticancer therapies, J Pathol. 196(3):254-265 (2002).
Boackle et al., "An IgG primary sequence exposure theory for complement activation using synthetic peptides," Nature. 282(5740):742-743 (1979).
Boerner et al., "Production of antigen-specific human monoclonal antibodies from in vitro-primed human splenocytes," J Immunol. 147(1):86-95 (1991).
Bonham et al., "Antagonistic antibodies to c-fms block c-fms-mediated activities reduce tumor-associated macrophages and decrease tumor growth in preclinical models," In Proc Am Assoc Cancer Res 50:503. Abstract #2077 (2009).
Bourette et al., "Early events in M-CSF receptor signaling," Growth Factors. 17(3): 155-166 (2000).
Bruggemann et al., "Designer mice: the production of human antibody repertoires in transgenic animals," Year Immunol. 7:33-40 (1993).
Brunhouse et al., "Isotypes of IgG: comparison of the primary structures of three pairs of isotypes which differ in their ability to activate complement," Mol Immunol. 16(11):907-917 (1979).
Burmester et al., "Mavrilimumab, a human monoclonal antibody targeting GM-CSF receptor[alpha], in subjects with rheumatoid arthritis: a randomised, double-blind, placebo-controlled, phase 1, first-in-human study," Ann Rheum Dis. 70(9):1542-9 (2011).
Burton et al., "The C1q receptor site on immunoglobulin G," Nature. 288:338-344 (1980).
Campbell et al., "The colony-stimulating factors and collagen-induced arthritis: exacerbation of disease by M-CSF and G-CSF and requirement for endogenous M-CSF," J Leukoc Biol. 68(1):144-150 (2000).
Carter et al., "Humanization of an anti-p185HER2 antibody for human cancer therapy," Proc Natl Acad Sci US A. 89(10):4285-4289 (1992).
Casset et al., "A peptide mimetic of an anti-CD4 monoclonal antibody by rational design," Biochem Biophys Res Commun. 307:198-205 (2003).
Cenci et al., "M-CSF neutralization and Egr-1 deficiency prevent ovariectomy-induced bone loss," J Clin Invest. 105(9):1279-1287 (2000).
Chari et al., "Immunoconjugates containing novel maytansinoids: promising anticancer drugs," Cancer Res. 52(1):127-131 (1992).
Chase et al., "Imatinib sensitivity as a consequence of a CSF1R-Y571 D mutation and CSF1/CSF1 R signaling abnormalities in the cell line GDM1," Leukemia. 23(2):358-364 (2009).
Choueiri et al., "The central role of osteoblasts in the metastasis of prostate cancer," Cancer Metastasis Rev. 25(4):601-609 (2006).
Cole et al., "The EBV-hybridoma technique and its application to human lung cancer," Monoclonal Antibodies and Cancer Therapy. Alan R. Liss, Inc. 77-96 (1985).
Coussens et al., "Structural alteration of viral homologue of receptor proto-oncogene fms at carboxyl terminus," Nature. 320(6059):277-280 (1986).
da Costa et al., "Presence of osteoclast-like multinucleated giant cells in the bone and nonostotic lesions of Langerhans cell histiocytosis," J Exp Med. 201(5):687-693 (2005).
Dai et al., "Targeted disruption of the mouse colony-stimulating factor 1 receptor gene results in osteopetrosis, mononuclear phagocyte deficiency, increased primitive progenitor cell frequencies, and reproductive defects," Blood. 99(1):111-120 (2002).
Daroszewska et al., "Mechanisms of disease: genetics of Paget's disease of bone and related disorders," Nat Clin Pract Rheumatol. 2(5):270-277 (2006).
Davies et al., "Affinity improvement of single antibody VH domains: residues in all three hypervariable regions affect antigen binding," Immunotechnology. 2(3):169-179 (1996).
DeNardo et al., "Leukocyte complexity predicts breast cancer survival an dfunctionally regulates response to chemotherapy," Cancer Research 1(1) pp. 1-15, (Apr. 2011).
Dewar et al., "Macrophage colony-stimulating factor receptor c-fms is a novel target of imatinib," Blood, 105(8):3127-32, (2005).
Drees et al., "Mechanisms of disease: Molecular insights into aseptic loosening of orthopedic implants," Nat Clin Pract Rheumatol. 3(3):165-171 (2007).
Dubowchik et al., "Doxorubicin immunoconjugates containing bivalent, lysosomally-cleavable dipeptide linkages," Bioorg Med Chem Lett. 12(11): 1529-1532 (2002).
Durocher et al., "High-level and high-throughput recombinant protein production by transient transfection of suspension-growing human 293-EBNA1 cells," Nucleic Acids Res. 30(2):E9 (2002).
English Translation of Notification of Reasons for Rejection for Japanese Patent Application No. 2012-542522, dated Feb. 25, 2014 (3 pages}.
European Search Report for Application No. EP 09007224.0 pp. 1-9 (Nov. 24, 2009).
European Search Report for Application No. EP 09015310 pp. 1-8 (Sep. 9, 2010).
Extended Search Report for European Patent Application No. EP 12158519.4, dated Aug. 2, 2012 (8 pages).

(56) References Cited

OTHER PUBLICATIONS

Feldstein et al., "Practice patterns in patients at risk for glucocorticoid-induced osteoporosis," Osteoporos Int. 16(12):2168-2174 (2005).
Flatman et al., "Process analytics for purification of monoclonal antibodies," J Chromatogr B Analyt Techno! Biomed Life Sci. 848{1):79-87 (2007).
Flick et al., "Recognition of activated CSF-1 receptor in breast carcinomas by a tyrosine 723 phosphospecific antibody," Oncogene 14:253-2561, (1997).
Geisse et al., "Eukaryotic expression systems: a comparison," Protein Expr Purif. 8(3):271-282 (1996).
Guzman-Clark et al., "Barriers in the management of glucocorticoid-induced osteoporosis," Arthritis Rheum. 57(1):140-146 (2007).
Hamilton, "Colony-stimulating factors in inflammation and auto-immunity," Nat Rev Immunol.8 (7):533-544 (2008).
Hao et al., "Expression of macrophage colony-stimulating factor and its receptor in microglia activation is linked to teratogen-induced neuronal damage," Neuroscience. 112(4):889-900 (2002).
Haran-Gehera et al., "Increased Circulating Colony-Stimulating Factor-1 (CSF-1) in SJL/J mice with radiation-induced acute myeloid leukemia (AML) is associated with autocrine regulation of AML cells by CSF-1," The American Society of Hematology 89(7):2537-2545, (Apr. 1, 1997).
Hayashi et al., "Osteoclast precursors in bone marrow and perito-neal cavity," J. Cell Physiol. 170(3):241-7, (Mar. 1997).
Hezareh et al., "Effector function activities of a panel of mutants of a broadly neutralizing antibody against human immunodeficiency virus type 1," J Viral. 75(24):12161-12168 (2001).
Hinman et al., "Preparation and characterization of monoclonal antibody conjugates of the calicheamicins: a novel and potent family of antitumor antibiotics," Cancer Res. 53(14):33363342 (1993).
Holt, L. et al., "Domain antibodies: proteins for therapy" Trends in Biotechnology. 21(11):484-490 (Nov. 1, 2003).
Hoogenboom et al., "By-passing immunisation. Human antibodies from synthetic repertoires of germline VH gene segments rear-ranged in vitro," J Mol Biol. 227(2):381-388 (1992).
Hume et al. (2012). "Therapeutic applications of macrophage colony-stimulating factor-1 (CSF-1) and antagonists of CSF-1 receptor (CSF-1R) signaling," Blood. Feb. 23, 2012;119(8):1810-20 (originally published online on Dec. 20, 2011).
Huston et al., "Protein engineering of single-chain Fv analogs and fusion proteins," Methods Enzymol. 203:46-88 (1991).
Ide et al., "Expression of colony-stimulating factor 1 receptor during prostrate development and prostate cancer progression," Proc. Natl. Acad. Sci. U.S.A. 99:14404-14409, (Oct. 29, 2002, e-pub. Oct. 15, 2002).
Idusogie et al., "Mapping of the C1 q binding site on rituxan, a chimeric antibody with a human IgG1 Fc," J Immunol. 164(8):4178-4184 (2000).
Ikonomidis et al., "Increased circulating C-reactive protein and macrophage-colony stimulating factor are complementary predic-tors of long-term outcome in patients with chronic coronary artery disease," Eur Heart J. 26(16):1618-1624 (2005).
Inaba et al., "Expression of M-CSF receptor encoded by c-fms on smooth muscle cells derived from arteriosclerotic lesion," J Biol Chem. 267(8):5693-5699 (1992).
International Search Report and Written Opinion for PCT Applica-tion No. PCT/EP2014/069451, mailed on Nov. 18, 2014, filed on Sep. 11, 2014, 13 pages.
International Search Report for International Patent Application No. PCT/EP2011/053214, mailed Apr. 28, 2011 (6 pages).
International Search Report for International Patent Application No. PCT/EP2013/054676, mailed May 7, 2013 (7 pages).
International Search Report for International Patent Application No. PCT/EP2012/075241, mailed Feb. 22, 2013 (7 pages).
International Search Report for PCT Application No. PCT/EP2011/053213, mailed on Sep. 1, 2011, filed on Mar. 3, 2011, 6 pages.
International Search Report for PCT Application No. PCT/EP2014/057909, mailed on Sep. 1, 2014, filed on Apr. 17, 2014, 6 pages.
Jakobovits et al., "Analysis of homozygous mutant chimeric mice: deletion of the immunoglobulin heavy-chain joining region blocks B-cell development and antibody production," Proc Natl Acad Sci USA. 90(6):2551-2555 (1993).
Jakobovits et al., "Germ-line transmission and expression of a human-derived yeast artificial chromosome," Nature. 362(6417):255-258 (1993).
Jeffrey et al., "Dipeptide-based highly potent doxorubicin antibody conjugates," Bioorg Med Chem Lett. 16(2):358-362 (2006).
Johnson et al., "Kabat database and its applications: 30 years after the first variability plot," Nucleic Acids Res. 28(1):214-218 (2000).
Jose et al., "Blockade of macrophage colony-stimulating factor reduces macrophage proliferation and accumulation in renal allograft rejection," American Journal of Transplantation 3:394-300, (2003).
Kabat et al., "Tabulation and analysis of amino acid and nucleic acid sequences of precursors, v-regions, c-regions, j-chain, beta2-microglobulins, major histocompatibility antigens, thy-1, comple-ment, c-reactive protein, thymopoietin, post-gamma globulin, and alpha2macroglobulin," Sequences of Proteins of Immunological Interest. U.S. Department of Health and Human Services, 10L (1983).
Kacinski et al., "Ovarian adenocarcinomas express fms-comple-mentary transcripts and fms antigen, often with coexpression of CSF-1," American Journal of Pathology 137(1):135-147, (Jul. 1990).
Kacinski, "CSF-1 and its receptor in breast carcinomas and neo-plasms of the female reproductive tract," Mol Reprod Dev. 46(1):71-74 (1997).
Kaku et al., "Amyloid beta protein deposition and neuron loss in osteopetrotic (op/op) mice," Brain Res Protoc. 12(2):1 04-108 (2003).
Kaufman, "Overview of vector design for mammalian gene expres-sion," Mol Biotechnol. 16(2):151-160(2000).
Kawakami et al., "Macophage-colony stimulating factor inhibits the growth of human ovarian cancer cells in vitro," European Journal of Cancer 36:1991-1997, (2000).
King et al., "Monoclonal antibody conjugates of doxorubicin pre-pared with branched peptide linkers: inhibition of aggregation by methoxytriethyleneglycol chains," J Med Chem. 45(19):4336-4343 (2002).
Kirma et al., "Elevated expression of the oncogene c-fms and its ligand, the macrophage colony-stimulating factor-1, in cervical cancer and the role of transforming growth factor-beta1 in inducing c-fms expression," Cancer Res. 67(5):1918-1926 (2007).
Kitaura et al., "M-CSF mediates TNF-induced inflammatory osteolysis," J Clin Invest. 115(12):3418-3427 (2005).
Kitaura, H. et al., "An anti-c-Fms antibody inhibits orthodontic tooth movement," Journal of Dental Research 87(4):396-400 (Apr. 1, 2008).
Kommoss et al., "Co-expression of M-CSF transcripts and protein, FMS (M-CSF receptor) transcripts and protein, and steroid receptor content in adenocarcinomas of the ovary," Journal of Pathology 174:111-119, (1994).
Kratz et al., "Prodrugs of anthracyclines in cancer chemotherapy," Curr Med Chem. 13(5):477-523 (2006).
Kuester et al. (2006). "Pharmacokinetics of Monoclonal Antibod-ies," chapter 3 in "Pharmacokinetics and Pharmacodynamics of Biotech Drugs," Meibohm (Ed.), Wiley-VCH, pp. 45-91.
Lee et al., "The Cbl protooncoprotein stimulates CSF-1 receptor multiubiquitination and endocytosis, and attenuates macrophage proliferation," EMBO J. 18(13):3616-3628 (1999).
Lee, A. et al., "Functional dissection of structural domains in the receptor for colony-stimulating Factor-1*" The Journal of Biologi-cal Chemistry 267(23):16472-16483 (Aug. 15, 1992).
Lenda et al., "Reduced macrophage recruitment, proliferation, and activation in colony-stimulating factor-1-deficient mice results in decreased tubular apoptosis during renal inflammation," J Immunol. 170(6):3254-3262 (2003).

(56) References Cited

OTHER PUBLICATIONS

Lester et al., "Current management of treatment-induced bone loss in women with breast cancer treated in the United Kingdom," Br J Cancer. 94(1):30-35 (2006).
Lewis et al., "Distinct apoptotic signaling characteristics of the anti-CD40 monoclonal antibody dacetuzumab and rituximab produce enhanced antitumor activity in non-Hodgkin lymphoma," Clin Cancer Res. 17(14):4672-4681 (2011).
Li et al., "Role of dimerization and modification of the CSF-1 receptor in its activation and internalization during the CSF-1 response," The EMBO Journal 10(2):277-288, (1991).
Lin et al., "Discovery of a cytokine and its receptor by functional screening of the extracellular proteome," Science 320:807-811, (May 9, 2008).
Lode et al., "Targeted therapy with a novel enediyne antibiotic calicheamicin theta(I)1 effectively suppresses growth and dissemination of liver metastases in a syngeneic model of murine neuroblastoma," Cancer Res. 58(14):2925-2928 (1998).
Lukas et al., "Inhibition of C1-mediated immune hemolysis by monomeric and dimeric peptides from the second constant domain of human immunoglobulin G," J Immunol. 127(6):2555-2560 (1981).
MacCallum et al., "Antibody-antigen interactions: contact analysis and binding site topography," J Mol Biol. 262:732-745 (1996).
MacDonald et al., "An antibody against the colony-stimulating factor 1 receptor depletes the resident subset of monocytes and tissue-and tumor-associated macrophages but does not inhibit inflammation," Blood. 116(19):3955-63 (2010).
Makrides, "Components of vectors for gene transfer and expression in mammalian cells," Protein Expr Purif. 17(2): 183-202 (1999).
Mancino et al., "Breast cancer increases osteoclastogenesis by secreting M-CSF and upregulating RANKL in stromal cells," Journal of Surgical Research 100:18-24, (2001, e-pub. Jul. 24, 2001).
Mantovani et al., "The chemokine system in diverse forms of macrophage activation and polarization," Trends Immunol. 25(12):677-686 (2004).
Marks et al., "By-passing immunization. Human antibodies from V-gene libraries displayed on phage," J Mol Biol. 222(3):581-597 (1991).
Martin et al., "Growth and angiogenesis of human breast cancer in a nude mouse tumour model is reduced by NK4, a HGF/SF antagonist," Carcinogenesis. 24(8):1317-1323 (2003).
Morgan et al., "The N-terminal end of the CH2 domain of chimeric human IgG1 anti-HLA-DR is necessary for C1q, Fc gamma RI and Fc gamma RIII binding," Immunology. 86(2):319-324 (1995).
Morrison et al., "Chimeric human antibody molecules: mouse antigen-binding domains with human constant region domains," Proc Natl Acad Sci U S A. 81(21):6851-6855 (1984).
Murayama, T. et al., "Intraperitoneal administration of ant-c-fms monoclonal antibody prevents initial events of atherogenesis but does not reduce the size of advanced lesions in apolipoprotein E-deficient mice," Circulation 99(13):1740-1746 (Apr. 6, 1999).
Murphy et al., "Expression of macrophage colony-stimulating factor receptor is increased in the AbetaPP(V717F) transgenic mouse model of Alzheimer's disease," Am J Pathol. 157(3):895-904 (2000).
Murphy et al., "Macrophage colony-stimulating factor augments beta-amyloid-induced interleukin-1, interleukin-6, and nitric oxide production by microglial cells," J Biol Chem. 273(33):20967-20971 (1998).
Nagy et al., "Stability of cytotoxic luteinizing hormone-releasing hormone conjugate (AN-152) containing doxorubicin 14-0-hemiglutarate in mouse and human serum in vitro: implications for the design of preclinical studies," Proc Natl Acad Sci U S A. 97(2):829-834 (2000).
Neuberger et al., "A hapten-specific chimaeric IgE antibody with human physiological effector function," Nature. 314(6008):268-270 (1985).

Ngan et al., "Proto-oncogenes and p53 protein expression in normal cervical stratified squamous epithelium and cervical intra-epithelial neoplasia," Eur J Cancer. 35(10):1546-1550l(1999).
Nicola et al., "Neutralizing and nonneutralizing monoclonal antibodies to the human granulocyte-macrophage colony-stimulating factor receptor alpha-chain," Blood. 82(6):1724-31 (1993).
Norderhaug et al., "Versatile vectors for transient and stable expression of recombinant antibody molecules in mammalian cells," J Immunol Methods. 204(1):77-87 (1997).
Orlandi et al., "Cloning immunoglobulin variable domains for expression by the polymerase chain reaction," Proc Natl Acad Sci U S A. 86(10):3833-3837 (1989).
Patel et al., "Colony-stimulating factor-1 receptor inhibitors for the treatment of cancer and inflammatory disease," Curr Top Med Chem. 9(7):599-610 (2009).
Paul, Structure and funtcion of immunoglobulins, Fundamental Immunology, 3rd Ed., Raven Press, 292-295 (1993).
Paulus et al., "Colony-stimulating factor-1 antibody reverses chemoresistance in human MCF7 breast cancer xenografts," Cancer Res. 66(8):4349-4356 (2006).
Pixley et al., "CSF-1 regulation of the wandering macrophage: complexity in action," Trends Cell Biol. 14(11):628-638 (2004).
Pollard, "Role of colony-stimulating factor-1 in reproduction and development," Mol Reprod Dev. 46(1):54-60 (1997).
Pollard, "Tumour-educated macrophages promote tumour progression and metastasis," Nat Rev Cancer. 4(1):71-78 (2004).
Queen et al., "A humanized antibody that binds to the interleukin 2 receptor," Proc Natl Acad Sci U S A. 86(24):10029-10033 (1989).
Rabello et al., "CSF1 gene associated with aggressive periodontitis in the Japanese population," Biochem Biophys Res Commun. 347(3):791-796 (2006).
Ridge et al., "FMS mutations in myelodysplastic, leukemic, and normal subjects," Proc Natl Acad Sci U S A. 87(4):1377-1380 (1990).
Riechmann et al., "Reshaping human antibodies for therapy," Nature. 332(6162): 323-327 (1988).
Ries et al. (2014). "Targeting tumor-associated macrophages with anti-CSF-1R antibody reveals a strategy for cancer therapy," Cancer Cell, 25(6):846-59.
Ritchlin et al., "Mechanisms of TNF-alpha-and RANKL-mediated osteoclastogenesis and bone resorption in psoriatic arthritis," J Clin Invest. 111(6):821-831 (2003).
Roggia et al., "Role of TNF-alpha producing T-cells in bone loss induced by estrogen deficiency," Minerva Med. 95(2):125-132 (2004).
Roth et al., "The biology of CSF-1 and its receptor," Curr Top Microbiol Immunol. 181:141-167 (1992).
Roussel et al., "Mouse NIH 3T3 cells expressing human colony-stimulating factor 1 (CSF-1) receptors overgrow in serum-free medium containing human CSF-1 as their only growth factor," Proc Natl Acad Sci USA. 86(20):7924-7927 (1989).
Roussel et al., "Transforming potential of the c-fms proto-oncogene (CSF-1 receptor)," Nature. 325(6104):549-552 (1987).
Saitoh et al., "Clinical significance of increased plasma concentration of macrophage colony-stimulating factor in patients with angina pectoris," J Am Coll Cardiol. 35(3):655-665 (2000).
Sawada et al., "Activation and proliferation of the isolated microglia by colony stimulating factor-1 and possible involvement of protein kinase C," Brain Res. 509(1):119-124 (1990).
Schlaeger et al., "Transient gene expression in mammalian cells grown in serum-free suspension culture," Cytotechnology. 30(1-3):71-83 (1999).
Schlaeger, "The protein hydrolysate, Primatone RL, is a cost-effective multiple growth promoter of mammalian cell culture in serum-containing and serum-free media and displays anti-apoptosis properties," J Immunol Methods. 194(2):191-199 (1996).
Scholl et al., "Anti-colony-stimulating factor-1 antibody staining in primary breast adenocarcinomas correlates with marked inflammatory cell infiltrates and prognosis," J Natl Cancer Inst. 86(2):120-126 (1994).
Shadduck et al., "Paradoxical stimulation of normal and leukemic rat hematopoiesis by monoclonal antibody to CSF-1 receptor," Experimental Hematology 24:314-317, (1996).

(56) References Cited

OTHER PUBLICATIONS

Sherr et al., "Inhibition of colony-stimulating factor-1 activity by monoclonal antibodies to the human CSF-1 receptor," Blood. 73(7):1786-93 (1989).
Sherr et al., "The c-fms proto-oncogene product is related to the receptor for the mononuclear phagocyte growth factor, CSF-1," Cell. 41(3):665-676 (1985).
Stanley et al., "Biology and action of colony-stimulating factor-1 ," Mol Reprod Dev. 46(1):4-10 (1997).
Stanley et al., "The biology and action of colony stimulating factor-1," Stem Cells. 12(Suppl 1):15-25 (1994).
Stanley et al., "CSF-1—A monoclonal phagocyte lineage-specific hemopoietic growth factor," Journal of Cellular Biochemistry 21(2):151-159, (1983).
Stoch et al., "Bone loss in men with prostate cancer treated with gonadotropin-releasing hormone aQonists," J Clin Endocrinol Metab. 86(6):2787-2791 (2001).
Sudo, T. et al., "Functional hierarchy of c-kit and c-fms in intramarrow production of CFU-M" Oncogene 11(12):2469-2476 (Dec. 21, 1995).
Tanaka et al., "Macrophage colony-stimulating factor is indispensable for both proliferation and differentiation of osteoclast progenitors," J Clin Invest. 91(1):257-263 (1993).
Taylor et al., "FMS receptor for M-CSF (CSF-1) is sensitive to the kinase inhibitor imatinib and mutation of Asp-802 to Val confers resistance," Oncogene pp. 1-5, (2005).
Thommesen et al., "Lysine 322 in the human IgG3 C(H)2 domain is crucial for antibody dependent complement activation," Mol Immunol. 37(16):995-1004 (2000).
Torgov et al., "Generation of an intensely potent anthracycline by a monoclonal antibody-beta-Qalactosidase conjugate," Bioconjugate Chern. 16(3):717-721 (2005).
Tortora et al., "Novel toll-like Receptor 9 (TLR9) agonists IMO inhibits tumor growth an cooperates with cetuximab in K-Ras mutant colon pancreatic cancers," Proceedings of the American Association for Cancer Research. 51:146 (2010).

van Dijk et al., "Human antibodies as next generation therapeutics," Curr Opin Chern Biol. 5(4):368-374(2001).
Vessella et al., "Targeting factors involved in bone remodeling as treatment strategies in prostate cancer bone metastasis," Clin Cancer Res. 12(20 Pt 2):6285s-6290s (2006).
Vitetta et al., "Redesigning nature's poisons to create anti-tumor reagents," Science. 238(4830): 1098-1104 (1987).
Wang et al., "Identification of the ligand-binding regions in the macrophage colony-stimulating factor receptor extracellular domain," Mol Cell Biol. 13(9):5348-59 (1993).
Weir et al., "Colony stimulating factor-1 plays a role in osteoclast formation and function in bone resorption induced by parathyroid hormone and parathyroid hormone-related protein," Journal of Bone and Mineral 11(10):1474-1481 (1996).
Werner et al., "Appropriate mammalian expression systems for biopharmaceuticals," Arzneimittelforschung. 48(8):870-880 (1998).
West et al., "A landscape effect in tenosynovial giant-cell tumor from activation of CSF1 EK expression by a translocation in a minority of tumor cells," Proc Natl Acad Sci U S A. 103(3):690-695 (2006).
White et al. (2001). "Antibody-targeted immunotherapy for treatment of malignancy," Annu Rev Med. 52:125-45.
Yang et al., "The relationship between point mutation and abnormal expression of c-fms oncogene in hepatocellular carcinoma," Hepatobiliary Pancreat Dis Int. 3(1):86-89 (2004).
Yeung et al., "Proteomic approaches to the analysis of early events in colony-stimulating factor-1 signal transduction," Mol Cell Proteomics. 2(11):1143-1155 (2003).
Zheng et al., "Membrane-bound macrophage colony-stimulating factor and its receptor play adhesion molecule-like roles in leukemic cells," Leuk Res. 24(5):375-383 (2000).
Zins et al., "Colon cancer cell-derived tumor necrosis factor-alpha mediates the tumor growth-promoting response in macrophages by up-regulating the colony-stimulating factor-1 pathway," Cancer Res. 67(3):1038-1045 (2007).

* cited by examiner

ANTIBODIES AGAINST HUMAN CSF-1R AND USES THEREOF

CROSS-REFERENCE TO RELATED APPLICATIONS

This application is a Divisional of U.S. patent application Ser. No. 14/640,183, filed Mar. 6, 2015, which is a Divisional of U.S. patent application Ser. No. 12/962,445, filed Dec. 7, 2010, now U.S. Pat. No. 8,999,327, issued Apr. 7, 2015, which claims the benefit of EP Patent Application Nos. 09 015 310.7, filed Dec. 10, 2009, and 10 173 407.7, filed Aug. 19, 2010, the entire disclosures of which are expressly incorporated by reference herein.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392029612SEQLIST.txt, date recorded: Oct. 12, 2016, size: 68 KB).

FIELD OF THE INVENTION

The present invention relates to antibodies against human CSF-1R (anti-CSF-1R antibodies), methods for their production, pharmaceutical compositions containing said antibodies, and uses thereof.

BACKGROUND OF THE INVENTION

The human CSF-1 receptor (CSF-1R; colony stimulating factor 1 receptor; synonyms: M-CSF receptor; Macrophage colony-stimulating factor 1 receptor, Fms proto-oncogene, c-fms, SEQ ID NO: 62) is known since 1986 (Coussens, L., et al., Nature 320 (1986) 277-280). CSF-1R is a growth factor and encoded by the c-fms proto-oncogene (reviewed e.g. in Roth, P and Stanley, E. R., Curr. Top. Microbiol Immunol. 181 (1992) 141-67).

CSF-1R is the receptor for CSF-1 colony stimulating factor 1, also called M-CSF, macrophage colony-stimulating factor) and mediates the biological effects of this cytokine (Sherr, C. J., et al., Cell 41 (1985) 665-676). The cloning of the colony stimulating factor-1 receptor (CSF-1R) (also called c-fms) was described for the first time in Roussel, M. F., et al., Nature 325 (1987) 549-552. In that publication, it was shown that CSF-1R had transforming potential dependent on changes in the Cterminal tail of the protein including the loss of the inhibitory tyrosine 969 phosphorylation which binds Cbl and thereby regulates receptor down regulation (Lee, P. S., et al., Embo J. 18 (1999) 3616-3628). Recently a second ligand for CSF-1R termed interleukin-34 (IL-34) was identified (Lin, H. et al, Science 320 (2008) 807-811).

The cytokine CSF-1 (colony stimulating factor 1, also called M-CSF, macrophage) is found extracellularly as a disulfide-linked homodimer (Stanley, E. R. et al., Journal of Cellular Biochemistry 21 (1983) 151-159; Stanley, E. R. et al., Stem Cells 12 Suppl. 1 (1995) 15-24).

The main biological effects of CSF-1R signaling are the differentiation, proliferation, migration, and survival of hematopoietic precursor cells to the macrophage lineage (including osteoclast). Activation of CSF-1R is mediated by its ligands, CSF-1 (M-CSF) and IL-34. Binding of CSF-1 (M-CSF) to CSF-1R induces the formation of homodimers and activation of the kinase by tyrosine phosphorylation (Li, W. et al, EMBO Journal.10 (1991) 277-288; Stanley, E. R., et al., Mol. Reprod. Dev. 46 (1997) 4-10).

The biologically active homodimer CSF-1 binds to the CSF-1R within the subdomains D1 to D3 of the extracellular domain of the CSF-1 receptor (CSF-1R-ECD). The CSF-1R-ECD comprises five immunoglobulin-like subdomains (designated D1 to D5). The subdomains D4 to D5 of the extracellular domain (CSF-1R-ECD) are not involved in the CSF-1 binding. (Wang, Z., et al Molecular and Cellular Biology 13 (1993) 5348-5359). The subdomain D4 is involved in dimerization (Yeung, Y-G., et al Molecular & Cellular Proteomics 2 (2003) 1143-1155; Pixley, F. J., et al., Trends Cell Biol 14 (2004) 628-638).

Further signaling is mediated by the p85 subunit of PI3K and Grb2 connecting to the PI3K/AKT and Ras/MAPK pathways, respectively. These two important signaling pathways can regulate proliferation, survival and apoptosis. Other signaling molecules that bind the phosphorylated intracellular domain of CSF-1R include STAT1, STAT3, PLCy, and Cbl (Bourette, R. P. and Rohrschneider, L. R., Growth Factors 17 (2000) 155-166).

CSF-1R signaling has a physiological role in immune responses, in bone remodeling and in the reproductive system. The knockout animals for either CSF-1 (Pollard, J. W., Mol. Reprod. Dev. 46 (1997) 54-61) or CSF-1R (Dai, X. M., et al., Blood 99 (2002) 111-120) have been shown to have osteopetrotic, hematopoietic, tissue macrophage, and reproductive phenotypes consistent with a role for CSF-1R in the respective cell types.

Sherr, C. J, et al., Blood 73 (1989) 1786-1793 relates to some antibodies against CSF-1R that inhibit the CSF-1 activity (see Sherr, C. J. et al., Blood 73 (1989) 1786-1793). Ashmun, R. A., et al., Blood 73 (1989) 827-837 relates to CSF-1R antibodies. Lenda, D., et al., Journal of Immunology 170 (2003) 3254-3262 relates to reduced macrophage recruitment, proliferation, and activation in CSF-1-deficient mice results in decreased tubular apoptosis during renal inflammation. Kitaura, H., et al., Journal of Dental Research 87 (2008) 396-400 refers to an anti-CSF-1 antibody which inhibits orthodontic tooth movement, WO 2001/030381 mentions CSF-1 activity inhibitors including antisense nucleotides and antibodies while disclosing only CSF-1 antisense nucleotides. WO 2004/045532 relates to metastases and bone loss prevention and treatment of metastatic cancer by a CSF-1 antagonist disclosing as antagonist anti-CSF-1-antibodies only. WO 2005/046657 relates to the treatment of inflammatory bowel disease by anti-CSF-1-antibodies. US 2002/0141994 relates to inhibitors of colony stimulating factors. WO 2006/096489 relates to the treatment of rheumatoid arthritis by anti-CSF-1-antibodies. WO 2009/026303 and WO 2009/112245 relate to certain anti-CSF-1R antibodies binding to CSF-1R within the first three subdomains (D1 to D3) of the Extracellular Domain (CSF-1R-ECD).

SUMMARY OF THE INVENTION

The invention comprises an isolated antibody binding to human CSF-1R, wherein the antibody binds to human CSF-1R fragment delD4 (SEQ ID NO: 65) and to human CSF-1R Extracellular Domain (SEQ ID NO: 64) with a ratio of 1:50 or lower.

The invention further comprises an isolated antibody wherein
a) the heavy chain variable domain comprises SEQ ID NO:7 and the light chain variable domain comprises SEQ ID NO:8,
b) the heavy chain variable domain comprises SEQ ID NO:15 and the light chain variable domain comprises SEQ ID NO:16;
c) the heavy chain variable domain comprises SEQ ID NO:75 and the light chain variable domain comprises SEQ NO:76;
d) the heavy chain variable domain comprises SEQ ID NO:83 and the light chain variable domain comprises SEQ ID NO:84;
or a humanized version thereof.

The invention further comprises an isolated antibody wherein
a) the heavy chain variable domain comprises SEQ ID NO:7 and the light chain variable domain comprises SEQ ID NO:8,
b) the heavy chain variable domain comprises SEQ NO:15 and the light chain variable domain comprises SEQ ID NO: 16;
or a humanized version thereof.

In one embodiment the isolated antibody comprises
a) a heavy chain variable domain comprising SEQ ID NO:23 and a light chain variable domain comprising SEQ ID NO:24, or
b) a heavy chain variable domain comprising SEQ ID NO:31 and a light chain variable domain comprising SEQ ID NO:32, or
c) a heavy chain variable domain comprising SEQ ID NO:39 and a light chain variable domain comprising SEQ NO:40, or
d) a heavy chain variable domain comprising SEQ ID NO:47 and a light chain variable domain comprising SEQ ID NO:48, or
e) a heavy chain variable domain comprising SEQ ID NO:55 and a light chain variable domain comprising SEQ ID NO:56.

The invention further comprises an isolated antibody, wherein
a) the heavy chain variable domain comprises a CDR3 region comprising SEQ ID NO: 1, a CDR2 region comprising SEQ ID NO: 2, and a CDR1 region comprising SEQ ID NO:3, and the light chain variable domain comprises a CDR3 region comprising SEQ ID NO: 4, a CDR2 region comprising SEQ ID NO:5, and a CDR1 region comprising SEQ NO:6, or
b) the heavy chain variable domain comprises a CDR3 region comprising SEQ ID NO: 9, a CDR2 region comprising SEQ ID NO: 10, and a CDR1 region comprising SEQ ID NO: 11, and the light chain variable domain comprises a CDR3 region comprising SEQ ID NO:12, a CDR2 region comprising SEQ ID NO: 13, and a CDR1 region comprising SEQ ID NO: 14, or
c) the heavy chain variable domain comprises a CDR3 region comprising SEQ ID NO: 17, a CDR2 region comprising SEQ ID NO: 18, and a CDR1 region comprising SEQ ID NO:19, and the light chain variable domain comprises a CDR3 region comprising SEQ ID NO: 20, a CDR2 region comprising SEQ ID NO:21, and a CDR1 region comprising SEQ ID NO:22, or
d) the heavy chain variable domain comprises a CDR3 region comprising SEQ ID NO: 25, a CDR2 region comprising SEQ ID NO: 26, and a CDR1 region comprising SEQ ID NO: 27, and the light chain variable domain comprises a CDR3 region comprising SEQ ID NO:28, a CDR2 region comprising SEQ ID NO: 29, and a CDR1 region comprising SEQ ID NO: 30, or
e) the heavy chain variable domain comprises a CDR3 region comprising SEQ ID NO: 33, a CDR2 region comprising SEQ ID NO: 34, and a CDR1 region comprising SEQ ID NO: 35, and the light chain variable domain comprises a CDR3 region comprising SEQ ID NO:36, a CDR2 region comprising SEQ ID NO: 37, and a CDR1 region comprising SEQ ID NO: 38, or
f) the heavy chain variable domain comprises a CDR3 region comprising SEQ ID NO:41, a CDR2 region comprising SEQ ID NO: 42, and a CDR1 region comprising SEQ ID NO:43, and the light chain variable domain comprises a CDR3 region comprising SEQ IT) NO: 44, a CDR2 region comprising SEQ ID NO:45, and a CDR1 region comprising SEQ ID NO:46, or
g) the heavy chain variable domain comprises a CDR3 region comprising SEQ ID NO: 49, a CDR2 region comprising SEQ ID NO: 50, and a CDR1 region comprising SEQ NO: 51, and the light chain variable domain comprises a CDR3 region comprising SEQ ID NO:52, a CDR2 region comprising SEQ ID NO: 53, and a CDR1 region comprising SEQ ID NO: 54; or
h) the heavy chain variable domain comprises a CDR3 region comprising SEQ ID NO:69, a CDR2 region comprising SEQ ID NO: 70, and a CDR1 region comprising SEQ ID NO:71, and the light chain variable domain comprises a CDR3 region comprising SEQ ID NO: 72, a CDR2 region comprising SEQ ID NO:73, and a CDR1 region comprising SEQ ID NO:74, or
i) the heavy chain variable domain comprises a CDR3 region comprising SEQ ID NO: 77, a CDR2 region comprising SEQ ID NO: 78, and a CDR1 region comprising SEQ ID NO: 79, and the light chain variable domain comprises a CDR3 region comprising SEQ ID NO:80, a CDR2 region comprising SEQ ID NO: 81, and a CDR1 region comprising SEQ ID NO: 82.

Preferably the antibody according to the invention is of human IgG1 subclass or of human IgG4 subclass.

A further embodiment of the invention is a pharmaceutical composition comprising any of the antibodies described herein.

The invention further comprises the use an of an antibody according to the invention for the manufacture of a medicament for treatment of a CSF-1R mediated disease.

The invention further comprises the use an of an antibody according to the invention for the manufacture of a medicament for treatment of cancer.

The invention further comprises the use an of an antibody according to the invention for the manufacture of a medicament for treatment of bone loss.

The invention further comprises the use an of an antibody according to the invention for the manufacture of a medicament for treatment of metastasis.

The invention further comprises the use an of an antibody according to the invention for the manufacture of a medicament for treatment of inflammatory diseases.

The invention further comprises an antibody according to the invention for treatment of a CSF-1R mediated disease.

The invention further comprises an antibody according to the invention for treatment of cancer.

The invention further comprises an antibody according to the invention for treatment of bone loss.

The invention further comprises an antibody according to the invention for treatment of metastasis.

The invention further comprises an antibody according to the invention for treatment of inflammatory diseases.

A further embodiment of the invention is a nucleic acid encoding an antibody wherein.

a) the heavy chain variable domain comprises a CDR3 region comprising SEQ ID NO: 1, a CDR2 region comprising SEQ ID NO: 2, and a CDR1 region comprising SEQ ID NO:3, and the light chain variable domain comprises a CDR3 region comprising SEQ ID NO: 4, a CDR2 region comprising SEQ ID NO:5, and a CDR1 region comprising SEQ NO:6, or, b) the heavy chain variable domain comprises a CDR3 region comprising SEQ ID NO: 9, a CDR2 region comprising SEQ ID NO: 10, and a CDR1 region comprising SEQ ID NO: 11, and the light chain variable domain comprises a CDR3 region comprising SEQ ID NO:12, a CDR2 region comprising SEQ ID NO: 13, and a CDR1 region comprising SEQ ID NO: 14, or c) the heavy chain variable domain comprises a CDR3 region comprising SEQ ID NO: 17, a CDR2 region comprising SEQ ID NO: 18, and a CDR1 region comprising SEQ ID NO:19, and the light chain variable domain comprises a CDR3 region comprising SEQ ID NO: 20, a CDR2 region comprising SEQ NO:21, and a CDR1 region comprising SEQ ID NO:22, or d) the heavy chain variable domain comprises a CDR3 region comprising SEQ ID NO: 25, a CDR2 region comprising SEQ ID NO: 26, and a CDR1 region comprising SEQ ID NO: 27, and the light chain variable domain comprises a CDR3 region comprising SEQ NO:28, a CDR2 region comprising SEQ ID NO: 29, and a CDR1 region comprising SEQ ID NO: 30, of e) the heavy chain variable domain comprises a CDR3 region comprising SEQ ID NO: 33, a CDR2 region comprising SEQ ID NO: 34, and a CDR1 region comprising SEQ ID NO: 35, and the light chain variable domain comprises a CDR3 region comprising SEQ ID NO:36, a CDR2 region comprising SEQ ID NO: 37, and a CDR1 region comprising SEQ ID NO: 38, or f) the heavy chain variable domain comprises a CDR3 region comprising SEQ ID NO:41, a CDR2 region comprising SEQ ID NO: 42 and a CDR1 region comprising SEQ ID NO:43, and the light chain variable domain comprises a CDR3 region comprising SEQ ID NO: 44, a CDR2 region comprising SEQ ID NO:45, and a CDR1 region comprising SEQ ID NO:46, or g) the heavy chain variable domain comprises a CDR3 region comprising SEQ ID NO: 49, a CDR2 region comprising SEQ ID NO: 50, and a CDR1 region comprising SEQ ID NO: 51, and the light chain variable domain comprises a CDR3 region comprising SEQ ID NO:52, a CDR2 region comprising SEQ ID NO: 53, and a CDR1 region comprising SEQ ID NO: 54, or h) the heavy chain variable domain comprises a CDR3 region comprising SEQ ID NO:69, a CDR2 region comprising SEQ ID NO: 70, and a CDR1 region comprising SEQ ID NO:71, and the light chain variable domain comprises a CDR3 region comprising SEQ ID NO: 72, a CDR2 region comprising SEQ ID NO:73, and a CDR1 region comprising SEQ ID NO:74, or i) the heavy chain variable domain comprises a CDR3 region comprising SEQ ID NO: 77, a CDR2 region comprising SEQ ID NO: 78, and a CDR1 region comprising SEQ ID NO: 79, and the light chain variable domain comprises a CDR3 region comprising SEQ ID NO:80, a CDR2 region comprising SEQ ID NO: 81, and a CDR1 region comprising SEQ ID NO: 82, A further embodiment of the invention is a nucleic acid encoding an antibody wherein a) the heavy chain variable domain comprises SEQ ID NO:7 and the light chain variable domain comprises SEQ ID NO:8, b) the heavy chain variable domain comprises SEQ ID NO:15 and the light chain variable domain comprises SEQ ID NO:16;

c) the heavy chain variable domain comprises SEQ ID NO:75 and the light chain variable domain comprises SEQ ID NO:76;

d) the heavy chain variable domain comprises SEQ ID NO:83 and the light chain variable domain comprises SEQ ID NO:84;

or a humanized version thereof.

A further embodiment of the invention is a nucleic acid encoding an antibody wherein a) the heavy chain variable domain comprises SEQ ID NO:23 and the light chain variable domain comprises SEQ ID NO:24, or b) the heavy chain variable domain comprises SEQ ID NO:31 and the light chain variable domain comprises SEQ ID NO:32, or c) the heavy chain variable domain comprises SEQ ID NO:39 and the light chain variable domain comprises SEQ ID NO:40, or d) the heavy chain variable domain comprises SEQ ID NO:47 and the light chain variable domain comprises SEQ ID NO:48, or e) the heavy chain variable domain comprises SEQ ID NO:55 and the light chain variable domain comprises SEQ ID NO:56.

The invention further provides expression vectors containing nucleic acid according to the invention capable of expressing said nucleic acid in a prokaryotic or eukaryotic host cell, and host cells containing such vectors for the recombinant production of an antibody according to the invention.

The invention further comprises a prokaryotic or eukaryotic host cell comprising a vector according to the invention.

The invention further comprises a method for the production of a recombinant human or humanized antibody according to the invention, the method comprising expressing a nucleic acid according to the invention in a prokaryotic or eukaryotic host cell and recovering said antibody from said cell or the cell culture supernatant. The invention further comprises the antibody obtained by such a recombinant method.

Antibodies according to the invention show benefits for patients in need of a CSF-1R targeting therapy. The antibodies according to the invention show efficient antiproliferative activity against ligand-independent and ligand-dependant proliferation and are therefore especially useful in the treatment of cancer and metastasis.

The invention further provides a method for treating a patient suffering from cancer, the method comprising administering to a patient diagnosed as having such a disease (and therefore being in need of such a therapy) an effective amount of an antibody according to the invention. The antibody is administered preferably in a pharmaceutical composition.

A further embodiment of the invention is a method for treating a patient suffering from cancer the method comprising administering to the patient an antibody according to the invention.

These and other embodiments of the invention are further described in the detailed description that follows.

DESCRIPTION OF THE SEQUENCES

SEQ ID NO: 1 heavy chain CDR3, Mab 2F11
SEQ ID NO: 2 heavy chain CDR2, Mab 2F11
SEQ ID NO: 3 heavy chain CDR1, Mab 2F11
SEQ ID NO: 4 light chain CDR3, Mab 2F11
SEQ ID NO: 5 light chain CDR2, Mab 2F11
SEQ ID NO: 6 light chain CDR1, Mab 2F11
SEQ ID NO: 7 heavy chain variable domain, Mab 2E11
SEQ ID NO: 8 light chain variable domain, Mab 2E11
SEQ ID NO: 9 heavy chain CDR3, Mab 2E10
SEQ ID NO: 10 heavy chain CDR2, Mab 2E10
SEQ ID NO: 11 heavy chain CDR1, Mab 2E10
SEQ ID NO: 12 light chain CDR3, Mab 2E10
SEQ ID NO: 13 light chain CDR2, Mab 2E10
SEQ ID NO: 14 light chain CDR1, Mab 2E10
SEQ ID NO: 15 heavy chain variable domain, Mab 2E10
SEQ ID NO: 16 light chain variable domain, Mab 2E10
SEQ ID NO: 17 heavy chain CDR3, hMab 2F11-c11
SEQ ID NO: 18 heavy chain CDR2, hMab 2F11-c11
SEQ ID NO: 19 heavy chain CDR1, hMab 2F11-c11
SEQ ID NO: 20 light chain CDR3, hMab 2F11-c11
SEQ ID NO: 21 light chain CDR2, hMab 2F11-c11
SEQ ID NO: 22 light chain CDR1, hMab 2F11-c11
SEQ ID NO: 23 heavy chain variable domain, hMab 2F11-c11
SEQ ID NO: 24 light chain variable domain, hMab 2F11-c11
SEQ ID NO: 25 heavy chain CDR3, hMab 2F11-d8
SEQ ID NO: 26 heavy chain CDR2, hMab 2F11-d8
SEQ ID NO: 27 heavy chain CDR1, hMab 2F11-d8
SEQ ID NO: 28 light chain CDR3, hMab 2F11-d8
SEQ ID NO: 29 light chain CDR2, hMab 2F11-d8
SEQ ID NO: 30 light chain CDR1, hMab 2F11-d8
SEQ ID NO: 31 heavy chain variable domain, hMab 2F11-d8
SEQ ID NO: 32 light chain variable domain, hMab 2F11-d8
SEQ ID NO: 33 heavy chain CDR3, hMab 2F11-e7
SEQ ID NO: 34 heavy chain CDR2, hMab 2F11-e7
SEQ ID NO: 35 heavy chain CDR1, hMab 2F11-e7
SEQ ID NO: 36 light chain CDR3, hMab 2F11-e7
SEQ ID NO: 37 light chain CDR2, hMab 2F11-e7
SEQ ID NO: 38 light chain CDR1, hMab 2F11-e7
SEQ ID NO: 39 heavy chain variable domain, hMab 2F11-e7
SEQ ID NO: 40 light chain variable domain, hMab 2F11-e7
SEQ ID NO: 41 heavy chain CDR3, hMab 2F11-f12
SEQ ID NO: 42 heavy chain CDR2, hMab 2F11-f12
SEQ ID NO: 43 heavy chain CDR1, hMab 2F11-f12
SEQ ID NO: 44, light chain CDR3, hMab 2F11-f12
SEQ ID NO: 45 light chain CDR2, hMab 2F11-f12
SEQ ID NO: 46 light chain CDR1, hMab 2F11-f12
SEQ ID NO: 47 heavy chain variable domain, hMab 2F11-f12
SEQ ID NO: 48 light chain variable domain, hMab 2F11-f12
SEQ ID NO: 49 heavy chain CDR3, hMab 2F11-g1
SEQ ID NO: 50 heavy chain CDR2, hMab 2F11-g1
SEQ ID NO: 51 heavy chain CDR1, hMab 2F11-g1
SEQ ID NO: 52 light chain CDR3, hMab 2F11-g1
SEQ ID NO: 53 light chain CDR2, hMab 2F11-g1
SEQ ID NO: 54 light chain CDR1, hMab 2F11-g1
SEQ ID NO: 55 heavy chain variable domain, hMab 2F11-g1
SEQ ID NO: 56 light chain variable domain, hMab 2F11-g1
SEQ ID NO: 57 human kappa light chain constant region
SEQ ID NO: 58 human heavy chain constant region derived from IgG1
SEQ ID NO: 59 human heavy chain constant region derived from IgG1 mutated on L234A and L235A
SEQ ID NO: 60 human heavy chain constant region derived from IgG4
SEQ ID NO: 61 human heavy chain constant region derived from IgG4 mutated on S228P
SEQ ID NO: 62 human wildtype CSF-1R (wt CSF-1R)
SEQ ID NO: 63 human mutant CSF-1R L301S Y969F
SEQ ID NO: 64 human CSF-1R Extracellular Domain
SEQ ID NO: 65 human CSF-1R fragment delD4
SEQ ID NO: 66 human CSF-1R fragment D1-D3
SEQ ID NO: 67 signal peptide
SEQ ID NO: 68 Primer
SEQ ID NO: 69 heavy chain CDR3, Mab 1G10
SEQ ID NO: 70 heavy chain CDR2, Mab 1G10
SEQ ID NO: 71 heavy chain CDR1, Mab 1G10
SEQ ID NO: 72 light chain CDR3, Mab 1G10
SEQ ID NO: 73 light chain CDR2, Mab 1G10
SEQ ID NO: 74 light chain CDR1, Mab 1G10
SEQ ID NO: 75 heavy chain variable domain, Mab 1G10
SEQ ID NO: 76 light chain variable domain, Mab 1G10
SEQ ID NO: 77 heavy chain CDR3, Mab 2H7
SEQ ID NO: 78 heavy chain CDR2, Mab 2H7
SEQ ID NO: 79 heavy chain CDR 1, Mab 2H7
SEQ ID NO: 80 light chain CDR3, Mab 2H7
SEQ ID NO: 81 light chain CDR2, Mab 2H7
SEQ ID NO: 82 light chain CDR1, Mab 2H7
SEQ ID NO: 83 heavy chain variable domain, Mab 2H7
SEQ ID NO: 84 light chain variable domain, Mab 2H7

DETAILED DESCRIPTION OF THE INVENTION

I. Introduction

Figure 1A:
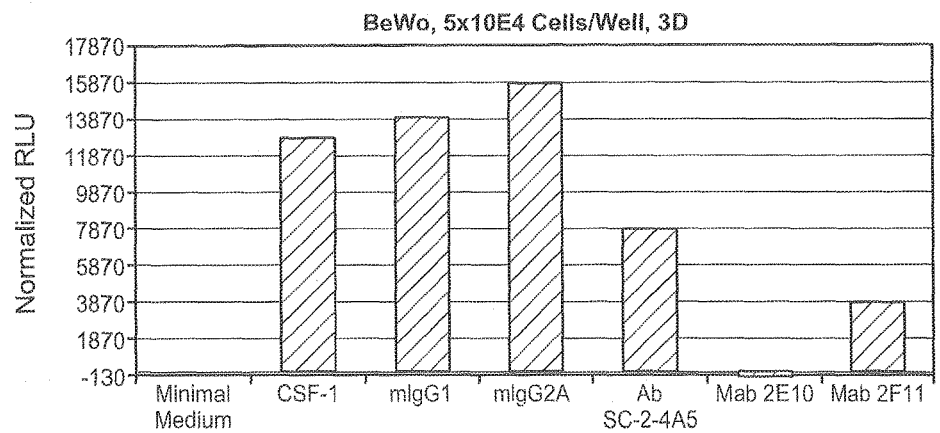
FIG. 1A-1B Growth inhibition of BeWo tumor cells in 3D culture under treatment with different anti-CSF-1R monoclonal antibodies at a concentration of 10 µg/ml. X axis: viability normalized mean relative light units (RLU) corresponding to the ATP-content of the cells (CellTiterGlo assay). Y axis: tested probes: Minimal Medium (0.5% FBS), mouse IgG1 (mIgG1, 10 µg/ml), mouse IgG2a (mIgG2a 10 µg/ml), CSF-1 only, Mab 2F11, Mab 2E10, Mab2H7, Mab 1G10 and SC 2-4A5. Highest inhibition of CSF-1 induced growth was observed with the anti-CSF-1R antibodies according to the invention.
Figure 1B:
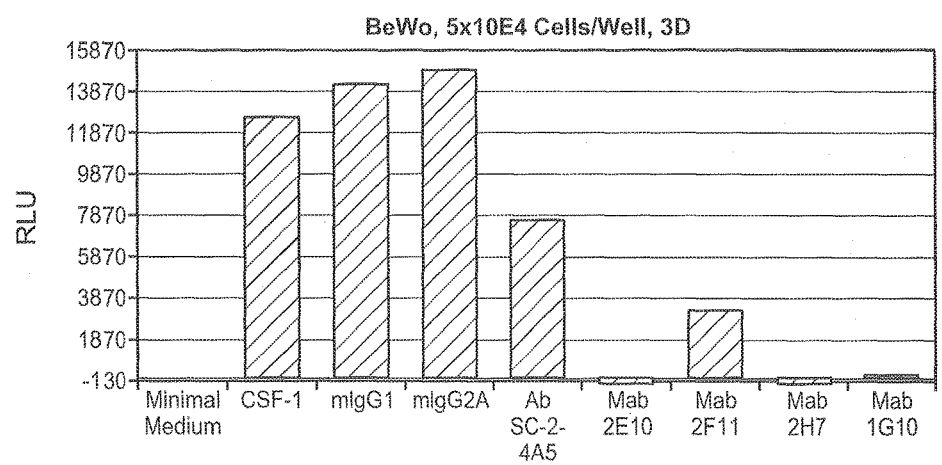

The present invention provides compositions that bind human CSF-1R or a portion thereof, kits and articles of manufacture comprising such compositions, and methods of using such compositions, including, e.g., methods for modulating ligand binding to CSF-1R and for modulating biological/physiological activities associated with ligand binding to CSF-1R. The invention is based in part on the identification of a variety of anti-CSF-1R antibodies that bind CSF-1R. The anti-CSF-1R antibodies of the invention can conveniently be used as therapeutic and diagnostic agents for use in targeting CSF-1R-mediated diseases including, e.g., cancer (including, for example, metastatic cancer), bone disorders (including, for example, bone loss), and inflammatory disorders.

Surprisingly it has been found that, using a human CSF-1R fragment delD4 in which the D4 subdomain of human CSF-1R-ECD was deleted (SEQ ID NO:65), the new anti-CSF-1R antibodies according to the invention could be selected. These antibodies show valuable properties like excellent ligand-dependant cell growth inhibition and at the same time ligand independent cell growth inhibition of NIH 3T3 cell, retrovirally infected with either an expression vector for full-length wildtype CSF-1R (SEQ ID NO:62) or mutant CSF-1R L301S Y969F (SEQ ID NO:63) whereby mutant CSF-1R recombinant cells are able to form spheroids independent of the CSF-1 ligand. Furthermore the antibodies according to the invention inhibit (both) human and cynomolgous macrophage differentiation, as they inhibit survival of human and cynomolgous monocytes.

II. Definitions

As used herein, the following terms have the meanings ascribed to them below unless otherwise specified.

The human CSF-1R (CSF-1 receptor; synonyms: M-CSF receptor; Macrophage colony-stimulating factor 1 receptor, Fms proto-oncogene, c-fms, SEQ ID NO: 22)) is known since 1986 (Coussens, L., et al., Nature 320 (1986) 277-280). CSF-1R is a growth factor and encoded by the c-fms proto-oncogene (reviewed e.g. in Roth, P. and Stanley, E. R., Curr. Top. Microbiol. Immunol. 181 (1992) 141-67).

CSF-1R is the receptor for CSF-1 (macrophage colony stimulating factor, also called M-CSF) and IL-34 and mediates the biological effects of these cytokines (Sherr, C. J., et al., Cell 41 (1985) 665-676 (Lin, H., et al., Science 320 (2008) 807-811). The cloning of the colony stimulating factor-1 receptor (also called c-fms) was described for the first time in Roussel, M. F., et al., Nature 325 (1987) 549-552. In that publication, it was shown that CSF-1R had transforming potential dependent on changes in the C-terminal tail of the protein including the loss of the inhibitory tyrosine 969 phosphorylation which binds Cb1 and thereby regulates receptor down regulation (Lee, P. S., et al., Embo J. 18 (1999) 3616-3628).

CSF-1R is a single chain, transmembrane receptor tyrosine kinase (RTK) and a member of the family of immunoglobulin (Ig) motif containing RTKs characterized by 5 repeated Ig-like subdomains D1-D5 in the extracellular domain (ECD) of the receptor (Wang, Z., et al Molecular and Cellular Biology 13 (1993) 5348-5359). The human CSF-1R Extracellular Domain (CSF-1R-ECD) (SEQ ID NO: 64) comprises all five extracellular Ig-like subdomains D1-D5. The human CSF-1R fragment delD4 (SEQ ID NO: 65) comprises the extracellular subdomains D1-D3 and D5, but is missing the D4 subdomain. The human CSF-1R fragment D1-D3 (SEQ ID NO: 66) comprises the respective subdomains D1-D3. The sequences are listed without the signal peptide MGSGPGVLLL LLVATAWHGQ G (SEQ ID NO: 67).

The intracellular protein tyrosine kinase domain is interrupted by a unique insert domain that is also present in the other related RTK class III family members that include the platelet derived growth factor receptors (PDGFR), stem cell growth factor receptor (c-Kit) and fins-like cytokine receptor (FLT3). In spite of the structural homology among this family of growth factor receptors, they have distinct tissue-specific functions.

CSF-1R is mainly expressed on cells of the monocytic lineage and in the female reproductive tract and placenta. In addition expression of CSF-1R has been reported in Langerhans cells in skin, a subset of smooth muscle cells (Inaba, T., et al., J. Biol. Chem. 267 (1992) 5693-5699), B cells (Baker, A. H., et al., Oncogene 8 (1993) 371-378) and microglia (Sawada, M., et al., Brain Res. 509 (1990) 119-124). Cells with mutant human CSF-1R ((SEQ ID NO: 23) are known to proliferate independently of ligand stimulation.

As used herein, "binding to human CSF-1R" or "specifically binding to human CSF-1R" refers to an antibody specifically binding to the human CSF-1R antigen with a binding affinity of KD-value of $1.0 \times 10^{-8}$ mol/l or lower at 35° C., in one embodiment of a KD-value of $1.0 \times 10^{-9}$ mail or lower at 35° C. The binding affinity is determined with a standard binding assay at 35° C., such as surface plasmon resonance technique (BIAcore®, GE-Healthcare Uppsala, Sweden) A method for determining the KD-value of the binding affinity is described in Example 9. Thus an "antibody binding to human CSF-1R" as used herein refers to an antibody specifically binding to the human CSF-1R antigen with a binding affinity of KD $1.0 \times 10^{-8}$ mol/l or lower (preferably $1.0 \times 10^{-8}$ mol/l-$1.0 \times 10^{-12}$ mol/l) at 35° C., preferably of a KD $1.0 \times 10^{-9}$ mol/l or lower at 35° C. (preferably $1.0 \times 10^{-9}$ mol/l-$1.0 \times 10^{-12}$ mol/l).

The "binding to human CSF-1R fragment delD4 (SEQ ID NO: 65) and to human CSF-1R Extracellular Domain (SEQ ID NO: 64)" as used herein is measured by a Surface Plasmon Resonance assay (Biacore assay) as described in Example 4. The human CSF-1R fragment delD4 (SEQ ID NO: 65) or human CSF-1R Extracellular Domain (SEQ ID NO: 64), respectively, are captured to the surface (each to a separate surface) and the test antibodies were added (each in a separate measurement), and the respective binding signals (Response Units (RU)) were determined. Reference signals (blank surface) were subtracted. If signals of nonbinding test antibodies were slightly below 0 the values were set as 0. Then the ratio of the respective binding signals (binding signal (RU) to human CSF-1R fragment delD4/binding signal (RU) to human CSF-1R Extracellular Domain (CSF-1R-ECD)) is determined. The antibodies according to the invention have a ratio of the binding signals (RU(delD4)/RU(CSF-1R-ECD) of 1:50 or lower, preferably of 1:100 or lower (the lower included end is 0 (e.g. if the RU is 0, then the ratio is 0:50 or 0:100)).

This means that such anti-CSF-1R antibodies according to the invention do not bind to the human CSF-1R fragment delD4 (like the anti-CCR5 antibody m<CCR5>Pz03.1C5 (deposited as DSM ACC 2683 on 18 Aug. 2004 at DSMZ) and have binding signals for binding to the human CSF-1R fragment delD4 in the range of the anti-CCR5 antibody m<CCR5>Pz03.1C5, which are below 20 RU (Response Units), preferably below 10 RU in a Surface Plasmon Resonance (BIAcore) assay as shown in Example 4.

The term "binding to human CSF-1R fragment D1-D3" refers to a binding affinity determination by a Surface Plasmon Resonance assay (Biacore assay). The test antibody is captured to the surface and the human CSF-1R fragment D1-D3 (SEQ ID NO: 66) was added and the respective binding affinities were determined. The term "not binding to human CSF-1R fragment D1-D3" denotes that in such an assay the detected signal was in the area of no more than 1.2 fold of background signal and therefore no significant binding could be detected and no binding affinity could he determined (see Example 10).

The term "antibody" encompasses the various forms of antibodies including but not being limited to whole antibodies, antibody fragments, human antibodies, humanized antibodies, chimeric antibodies, T cell epitope depleted antibodies, and further genetically engineered antibodies as long as the characteristic properties according to the invention are retained. "Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g., described in Houston, J. S., Methods in Enzymol, 203 (1991) 46-88). In addition, antibody fragments comprise single chain polypeptides having the characteristics of a $V_H$ domain binding to CSF-1R, namely being able to assemble together with a $V_L$ domain, or of a $V_L$ domain binding to CSF-1R, namely being able to assemble together with a $V_H$ domain to a functional antigen binding site and thereby providing the property.

The terms "monoclonal antibody" or "monoclonal antibody composition" as used herein refer to a preparation of antibody molecules of a single amino acid composition.

The term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising a mouse variable region and a human constant region are especially preferred. Such rat/human chimeric antibodies are the product of expressed immunoglobulin genes comprising DNA segments encoding rat immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad Sci. USA 81 (1984) 6851-6855; U.S. Pat. No. 5,202,238 and U.S. Pat. No. 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See e.g. Riechmann, L., et al., Nature 332 (1988) 323-327; and Neuberger, M. S., et al., Nature 314 (1985) 268-270. Optionally the framework region can be modified by further mutations. Also the CDRs can be modified by one or more mutations to generate antibodies according to the invention e.g. by mutagenesis based upon molecular modeling as described by Riechmann, L., et al., Nature 332 (1988) 323-327 and Queen, C., et al., Proc. Natl. Acad. Sci. USA 86 (1989) 10029-10033, or others. Particularly preferred CDRs correspond to those representing sequences recognizing the antigens noted above for chimeric antibodies. A "humanized version of an antibody according to the invention" (which is e.g. of mouse origin) refers to an antibody, which is based on the mouse antibody sequences in which the $V_H$ and $V_L$ are humanized by standard techniques (including CDR grafting and optionally subsequent mutagenesis of certain amino acids in the framework region and the CDRs). Preferably such humanized version is chimerized with a human constant region (see e.g. Sequences SEQ ID NO:57-61).

Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

In the following examples the terms "Mab" or "muMab" refer to murine monoclonal antibodies such as Mab 2F11 or Mab 2E10, whereas the term "hMab" refers to humanized monoclonal versions of such murine antibodies such as hMab 2F11-c11, hMab 2F11-d8, hMab 2F11-e7 hMab 2F11-f12, etc.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits., et al., Nature 362 (1993) 255-258; Brueggemann, M., et al., Year Immunol. 7 (1993) 33-40). Human antibodies can also be produced in phage display libraries (Hoogenboom, H. R., and Winter, G. J. Mol. Biol. 227 (1992) 381-388; Marks, J. D., et al., J. Mol. Biol. 222 (1991) 581-597). The techniques of Cole, et al and Boemer, et al., are also available for the preparation of human monoclonal antibodies (Cole, S. P. C., et al., Monoclonal Antibodies and Cancer Therapy, Alan R. Liss, p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The antibodies according to the invention include, in addition, such antibodies having "conservative sequence modifications", nucleotide and amino acid sequence modifications which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-CSF-1R antibody can he preferably replaced with another amino acid residue from the same side chain family.

Amino acid substitutions can be performed by mutagenesis based upon molecular modeling as described by Riechmann, L., et al, Nature 332 (1988) 323-327 and Queen, C., et al., Proc. Natl. Acad. Sci. USA 86 (1989) 10029-10033.

The term "epitope" denotes a protein determinant of human CSF-1R capable of specifically binding to an antibody. Epitopes usually consist of chemically active surface groupings of molecules such as amino acids or sugar side chains and usually epitopes have specific three dimensional structural characteristics, as well as specific charge characteristics. Conformational and nonconformational epitopes are distinguished in that the binding to the former but not the latter is lost in the presence of denaturing solvents. Preferably an antibody according to the invention binds specifically to native and to denatured CSF-1R.

The "variable domain" (variable domain of a light chain ($V_L$), variable domain of a heavy chain ($V_H$)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

The "Fc part" or "Fc portion" of an antibody is not involved directly in binding of an antibody to an antigen, but exhibit various effector functions. A "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ, and μ, respectively. The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described e.g. by Boackle, R. J., et al., Nature 282 (1979) 742-743, Lukas, T. J., et al., J. Immunol. 127 (1981) 2555-2560, Brunhouse, R., and Cebra, J. J., Mol. Immunol. 16 (1979) 907-917, Burton, D. R., et al., Nature 288 (1980) 338-344, Thommesen, J. E., et al., Mol. Immunol. 37 (2000) 995-1004, Idusogie, E. E., et al., J. Immunol.164 (2000) 4178-4184, Hezareh, M., et al., J. Virology 75 (2001) 12161-12168, Morgan, A., et al., Immunology 86 (1995) 319-324, EP 0307434. Such binding sites are e.g. L234, L235, D270, N297, E318, K320, K322, P331 and P329 (numbering according to EU index of Kabat, E. A., see below). Antibodies of subclass IgG1, IgG2 and IgG3 usually show complement activation and C1q and C3 binding, whereas IgG4 do not activate the complement system and do not bind C1q and C3.

In one embodiment the antibody according to the invention comprises a Fc part derived from human origin and preferably all other parts of the human constant regions. As used herein the term "Fc part derived from human origin" denotes a Fc part which is either a Fc part of a human antibody of the subclass IgG1, IgG2, IgG3 or IgG4, preferably a Fc part from human IgG1 subclass, a mutated Fc part from human IgG1 subclass (preferably with a mutation on L234A+L235A), a Fc part from human IgG4 subclass or a mutated Fc part from human IgG4 subclass (preferably with a mutation on S228P). Mostly preferred are the human heavy chain constant regions of SEQ ID NO: 58 (human IgG1 subclass), SEQ ID NO: 59 (human IgG1 subclass with mutations L234A and L235A), SEQ ID NO: 60 human IgG4 subclass), or SEQ ID NO: 61 (human IgG4 subclass with mutation S228P).

The terms "nucleic acid" or "nucleic acid molecule", as used herein, are intended to include DNA molecules and RNA molecules. A nucleic acid molecule may be single-stranded or double-stranded, but preferably is double-stranded DNA.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

As used herein, the expressions "cell", "cell line", and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount encompasses an amount in which any toxic or detrimental effects of the substance/molecule are outweighed by the therapeutically beneficial effects. A therapeutically effective amount also encompasses an amount sufficient to confer benefit, e.g., clinical benefit.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount. A prophylactically effective amount encompasses an amount sufficient to confer benefit, e.g., clinical benefit.

In the case of pre-cancerous, benign, early or late-stage tumors, the therapeutically effective amount of the angiogenic inhibitor may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit or delay, to some extent, tumor growth or tumor progression; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

To "reduce" or "inhibit" is to decrease or reduce an activity, function, and/or amount as compared to a reference. In certain embodiments, by "reduce" or "inhibit" is meant the ability to cause an overall decrease of 20% or greater. In another embodiment, by "reduce" or "inhibit" is meant the ability to cause an overall decrease of 50% or greater. In yet another embodiment, by "reduce" or "inhibit" is meant the ability to cause an overall decrease of 75%, 85%, 90%, 95%, or greater. Reduce or inhibit can refer to the symptoms of the disorder being treated, the presence or size of metastases, the size of the primary tumor, or the size or number of the blood vessels in angiogenic disorders.

A "disorder" is any condition that would benefit from treatment including, but not limited to, chronic and acute disorders or diseases including those pathological conditions which predispose the mammal to the disorder in question. Disorders include cancer (including metastatic cancer), bone disorders (including, e.g., bone loss such as osteoporosis), and inflammatory disorders.

III. Antibodies and Methods of the Invention

The invention comprises an antibody binding to human CSF-1R, wherein the antibody binds to human CSF-1R fragment delD4 (comprising the extracellular subdomains D1-D3 and D5) (SEQ ID NO: 65) and to human CSF-1R Extracellular Domain (CSF-1R-ECD) (comprising the extracellular subdomains D1-D5) (SEQ ID NO: 64) with a ratio of 1:50 or lower.

The invention further comprises an antibody comprising a heavy chain variable domain CDR3 region comprising SEQ ID NO: 1, SEQ ID NO: 9, SEQ ID NO:23, SEQ ID NO:31, SEQ NO:39, SEQ ID NO:47 or SEQ ID NO:55.

The invention further comprises an antibody wherein
a) the heavy chain variable domain comprises SEQ ID NO:7 and the light chain variable domain comprises SEQ ID NO:8,
b) the heavy chain variable domain comprises SEQ ID NO:15 and the light chain variable domain comprises SEQ ID NO:16; or a humanized version thereof.

The invention further comprises an antibody wherein
a) the heavy chain variable domain comprises SEQ ID NO:7 and the light chain variable domain comprises SEQ ID NO:8,
b) the heavy chain variable domain comprises SEQ ID NO:15 and the light chain variable domain comprises SEQ ID NO:16;
c) the heavy chain variable domain comprises SEQ ID NO:75 and the light chain variable domain comprises SEQ ID NO:76;
d) the heavy chain variable domain comprises SEQ ID NO:83 and the light chain variable domain comprises SEQ ID NO:84;
or a humanized version thereof.

The invention further comprises an antibody wherein the heavy chain variable domain comprises SEQ NO:7 and the light chain variable domain comprises SEQ NO:8, or a humanized version thereof.

In one embodiment the antibody comprises
a) a heavy chain variable domain comprising SEQ ID NO:23 and a light chain variable domain comprising SEQ ID NO:24, or
b) a heavy chain variable domain comprising SEQ ID NO:31 and a light chain variable domain comprising SEQ ID NO:32, or
c) a heavy chain variable domain comprising SEQ ID NO:39 and a light chain variable domain comprising SEQ ID NO:40, or
d) a heavy chain variable domain comprising SEQ ID NO:47 and a light chain variable domain comprising SEQ ID NO:48, or
e) a heavy chain variable domain comprising SEQ ID NO:55 and a light chain variable domain comprising SEQ ID NO:56.

In one embodiment the antibody comprises
a) a heavy chain variable domain comprising SEQ ID NO:23 and a light chain variable domain comprising SEQ ID NO:24, or
b) a heavy chain variable domain comprising SEQ ID NO:31 and a light chain variable domain comprising SEQ ID NO:32, or
c) a heavy chain variable domain comprising SEQ NO:39 and a light chain variable domain comprising SEQ ID NO:40, or
d) a heavy chain variable domain comprising SEQ ID NO:47 and a light chain variable domain comprising SEQ ID NO:48.

In one embodiment the antibody comprises
a heavy chain variable domain comprising SEQ ID NO:23 and a light chain variable domain comprising SEQ ID NO:24, or In one embodiment the antibody comprises
a heavy chain variable domain comprising SEQ ID NO:31 and a light chain variable domain comprising SEQ ID NO:32.

In one embodiment the antibody comprises
a heavy chain variable domain comprising SEQ ID NO:39 and a light chain variable domain comprising SEQ ID NO:40.

In one embodiment the antibody comprises
a heavy chain variable domain comprising SEQ ID NO:47 and a light chain variable domain comprising SEQ ID NO:48.

The invention further comprises an antibody wherein the heavy chain variable domain comprises SEQ ID NO: 15 and the light chain variable domain comprises SEQ ID NO:16, or a humanized version thereof.

The invention further comprises an antibody wherein the heavy chain variable domain comprises SEQ ID NO:75 and the light chain variable domain comprises SEQ ID NO:76; or a humanized version thereof.

The invention further comprises an antibody wherein the heavy chain variable domain comprises SEQ NO:83 and the light chain variable domain comprises SEQ ID NO:84; or a humanized version thereof.

The invention further comprises an antibody, wherein
a) the heavy chain variable domain comprises a CDR3 region comprising SEQ ID NO:1, a CDR2 region comprising SEQ ID NO: 2, and a CDR1 region comprising SEQ ID NO:3, and the light chain variable domain comprises a CDR3 region comprising SEQ ID NO: 4, a CDR2 region comprising SEQ ID NO:5, and a CDR1 region comprising SEQ ID NO:6, or,
b) the heavy chain variable domain comprises a CDR3 region comprising SEQ ID NO: 9, a CDR2 region comprising SEQ ID NO: 10, and a CDR1 region comprising SEQ ID NO: 11, and the light chain variable domain comprises a CDR3 region comprising SEQ ID NO: 12, a CDR2 region comprising SEQ ID NO: 13, and a CDR1 region comprising SEQ ID NO: 14, or
c) the heavy chain variable domain comprises a CDR3 region comprising SEQ ID NO: 17, a CDR2 region comprising SEQ ID NO: 18, and a CDR1 region comprising SEQ ID NO: 19, and the light chain variable domain comprises a CDR3 region comprising SEQ ID NO: 20, a CDR2 region comprising SEQ ID NO:21, and a CDR1 region comprising SEQ ID NO:22, or d) the heavy chain variable domain comprises a CDR3 region comprising SEQ ID NO: 25, a CDR2 region comprising SEQ ID NO: 26, and a CDR1 region comprising SEQ ID NO: 27, and the light chain variable domain comprises a CDR3 region comprising SEQ ID NO:28, a CDR2 region comprising SEQ ID NO: 29, and a CDR1 region comprising SEQ ID NO: 30, or e) the heavy chain variable domain comprises a CDR3 region comprising SEQ ID NO: 33, a CDR2 region comprising SEQ ID NO: 34, and a CDR1 region comprising SEQ ID NO: 35, and the light chain variable domain comprises a CDR3 region comprising SEQ ID NO:36, a CDR2 region comprising SEQ ID NO: 37, and a CDR1 region comprising SEQ ID NO: 38, or f) the heavy chain variable domain comprises a CDR3 region comprising SEQ ID NO:41, a CDR2 region comprising SEQ ID NO: 42, and a CDR1 region comprising SEQ ID NO:43, and the light chain variable domain comprises a CDR3 region comprising SEQ ID NO: 44, a CDR2 region comprising SEQ ID NO:45, and a CDR1 region comprising SEQ ID NO:46, or g) the heavy chain variable domain comprises a CDR3 region comprising SEQ ID NO: 49, a CDR2 region comprising SEQ ID NO: 50, and a CDR1 region comprising SEQ ID NO: 51, and the light chain variable domain comprises a CDR3 region comprising SEQ ID NO:52, a CDR2 region comprising SEQ ID NO: 53, and a CDR1 region comprising SEQ ID NO: 54.

The invention further comprises an antibody, wherein a) the heavy chain variable domain comprises a CDR3 region comprising SEQ ID NO:1, a CDR2 region comprising SEQ ID NO: 2, and a CDR1 region comprising SEQ ID NO:3, and the light chain variable domain comprises a CDR3 region comprising SEQ ID NO: 4, a CDR2 region comprising SEQ ID NO:5, and a CDR1 region comprising SEQ ID NO:6, or, b) the heavy chain variable domain comprises a CDR3 region comprising SEQ ID NO: 9, a CDR2 region comprising SEQ ID NO: 10, and a CDR1 region comprising SEQ ID NO: 11, and the light chain variable domain comprises a CDR3 region comprising SEQ ID NO:12, a CDR2 region comprising SEQ NO: 13, and a CDR1 region comprising SEQ ID NO: 14, or c) the heavy chain variable domain comprises a CDR3 region comprising SEQ ID NO: 17, a CDR2 region comprising SEQ ID NO: 18, and a CDR1 region comprising SEQ ID NO:19, and the light chain variable domain comprises a CDR3 region comprising SEQ ID NO: 20, a CDR2 region comprising SEQ ID NO:21, and a CDR1 region comprising SEQ ID NO:22, or d) the heavy chain variable domain comprises a CDR3 region comprising SEQ ID NO: 25, a CDR2 region comprising SEQ ID NO: 26, and a CDR1 region comprising SEQ ID NO: 27, and the light chain variable domain comprises a CDR3 region comprising SEQ NO:28, a CDR2 region comprising SEQ ID NO: 29, and a CDR1 region comprising SEQ ID NO: 30, or e) the heavy chain variable domain comprises a CDR3 region comprising SEQ ID NO: 33, a CDR2 region comprising SEQ ID NO: 34, and a CDR1 region comprising SEQ ID NO: 35, and the light chain variable domain comprises a CDR3 region comprising SEQ NO:36, a CDR2 region comprising SEQ ID NO: 37, and a CDR1 region comprising SEQ ID NO: 38, or f) the heavy chain variable domain comprises a CDR3 region comprising SEQ NO:41, a CDR2 region comprising SEQ ID NO: 42, and a CDR1 region comprising SEQ ID NO:43, and the light chain variable domain comprises a CDR3 region comprising SEQ ID NO: 44, a CDR2 region comprising SEQ ID NO:45, and a CDR1 region comprising SEQ NO:46, g) the heavy chain variable domain comprises a CDR3 region comprising SEQ ID NO: 49, a CDR2 region comprising SEQ ID NO: 50, and a CDR1 region comprising SEQ ID NO: 51, and the light chain variable domain comprises a CDR3 region comprising SEQ ID NO:52, a CDR2 region comprising SEQ ID NO: 53, and a CDR1 region comprising SEQ ID NO: 54;

h) the heavy chain variable domain comprises a CDR3 region comprising SEQ ID NO:69, a CDR2 region comprising SEQ ID NO: 70, and a CDR1 region comprising SEQ ID NO:71, and the light chain variable domain comprises a CDR3 region comprising SEQ ID NO: 72, a CDR2 region comprising SEQ ID NO:73, and a CDR1 region comprising SEQ ID NO:74, or i) the heavy chain variable domain comprises a CDR3 region comprising SEQ ID NO: 77, a CDR2 region comprising SEQ ID NO: 78, and a CDR1 region comprising SEQ ID NO: 79, and the light chain variable domain comprises a CDR3 region comprising SEQ ID NO:80, a CDR2 region comprising SEQ ID NO: 81, and a CDR1 region comprising SEQ ID NO: 82.

In one embodiment the antibody comprises a) the heavy chain variable domain comprises a CDR3 region comprising SEQ ID NO:69, a CDR2 region comprising SEQ ID NO: 70, and a CDR1 region comprising SEQ ID NO:71, and the light chain variable domain comprises a CDR3 region comprising SEQ ID NO: 72, a CDR2 region comprising SEQ NO:73, and a CDR1 region comprising SEQ ID NO:74, or b) the heavy chain variable domain comprises a CDR3 region comprising SEQ ID NO: 77, a CDR2 region comprising SEQ ID NO: 78, and a CDR1 region comprising SEQ ID NO: 79, and the light chain variable domain comprises a CDR3 region comprising SEQ ID NO:80, a CDR2 region comprising SEQ ID NO: 81, and a CDR1 region comprising SEQ ID NO: 82.

In one embodiment the antibody comprises a) the heavy chain variable domain comprises a CDR3 region comprising SEQ ID NO: 17, a CDR2 region comprising SEQ ID NO: 18, and a CDR1 region comprising SEQ ID NO: 19, and the light chain variable domain comprises a CDR3 region comprising SEQ ID NO: 20, a CDR2 region comprising SEQ ID NO:21, and a CDR1 region comprising SEQ ID NO:22, or b) the heavy chain variable domain comprises a CDR3 region comprising SEQ ID NO: 25, a CDR2 region comprising SEQ ID NO: 26, and a CDR1 region comprising SEQ ID NO: 27, and the light chain variable domain comprises a CDR3 region comprising SEQ ID NO:28, a CDR2 region comprising SEQ ID NO: 29, and a CDR1 region comprising SEQ ID NO: 30, or c) the heavy chain variable domain comprises a CDR3 region comprising SEQ ID NO: 33, a CDR2 region comprising SEQ ID NO: 34, and a CDR1 region comprising SEQ ID NO: 35, and the light chain variable domain comprises a CDR3 region comprising SEQ ID NO:36, a CDR2 region comprising SEQ ID NO: 37, and a CDR1 region comprising SEQ ID NO: 38, or d) the heavy chain variable domain comprises a CDR3 region comprising SEQ ID NO:41, a CDR2 region comprising SEQ ID NO: 42, and a CDR1 region comprising SEQ ID NO:43, and the light chain variable domain comprises a CDR3 region comprising SEQ ID NO: 44, a CDR2 region comprising SEQ ID NO:45, and a CDR1 region comprising SEQ ID NO:46, or e) the heavy chain variable domain comprises a CDR3 region comprising SEQ ID NO: 49, a CDR2 region comprising SEQ ID NO: 50, and a CDR1 region comprising SEQ ID NO: 51, and the light chain variable domain comprises a CDR3 region comprising SEQ ID NO:52, a CDR2 region comprising SEQ ID NO: 53, and a CDR1 region comprising SEQ ID NO: 54.

In one embodiment the antibody comprises a) the heavy chain variable domain comprises a CDR3 region comprising SEQ ID NO: 17, a CDR2 region comprising SEQ ID NO: 18, and a CDR1 region comprising SEQ ID NO:19, and the light chain variable domain comprises a CDR3 region comprising SEQ ID NO: 20, a CDR2 region comprising SEQ ID NO:21, and a CDR1 region comprising SEQ ID NO:22, or b) the heavy chain variable domain comprises a CDR3 region comprising SEQ ID NO: 25, a CDR2 region comprising SEQ ID NO: 26, and a CDR1 region comprising SEQ ID NO: 27, and the light chain variable domain comprises a CDR3 region comprising SEQ ID NO:28, a CDR2 region comprising SEQ ID NO: 29, and a CDR1 region comprising SEQ ID NO: 30, or c) the heavy chain variable domain comprises a CDR3 region comprising SEQ ID NO: 33, a CDR2 region comprising SEQ ID NO: 34, and a CDR1 region comprising SEQ ID NO: 35, and the light chain variable domain comprises a CDR3 region comprising SEQ ID NO:36, a CDR2 region comprising SEQ ID NO: 37, and a CDR1 region comprising SEQ ID NO: 38, or d) the heavy chain variable domain comprises a CDR3 region comprising SEQ NO:41, a CDR2 region comprising SEQ ID NO: 42, and a CDR1 region comprising SEQ ID NO:43, and the light chain variable domain comprises a CDR3 region comprising SEQ ID NO: 44, a CDR2 region comprising SEQ ID NO:45, and a CDR1 region comprising SEQ ID NO:46.

In one embodiment the antibody comprises
the heavy chain variable domain comprises a CDR3 region comprising SEQ ID NO: 17, a CDR2 region comprising SEQ ID NO: 18, and a CDR1 region comprising SEQ ID NO:19, and the light chain variable domain comprises a CDR3 region comprising SEQ ID NO: 20, a CDR2 region comprising SEQ ID NO:21, and a CDR1 region comprising SEQ ID NO:22, In one embodiment the antibody comprises
the heavy chain variable domain comprises a CDR3 region comprising SEQ ID NO: 25, a CDR2 region comprising SEQ ID NO: 26, and a CDR1 region comprising SEQ ID NO: 27, and the light chain variable domain comprises a CDR3 region comprising SEQ ID NO:28, a CDR2 region comprising SEQ ID NO: 29, and a CDR1 region comprising SEQ ID NO: 30.

In one embodiment the antibody comprises
the heavy chain variable domain comprises a CDR3 region comprising SEQ ID NO: 33, a CDR2 region comprising SEQ ID NO: 34, and a CDR1 region comprising SEQ ID NO: 35, and the light chain variable domain comprises a CDR3 region comprising SEQ ID NO:36, a CDR2 region comprising SEQ ID NO: 37 and a CDR1 region comprising SEQ ID NO: 38.

In one embodiment the antibody comprises
the heavy chain variable domain comprises a CDR3 region comprising SEQ ID NO:41, a CDR2 region comprising SEQ ID NO: 42, and a CDR1 region comprising SEQ ID NO:43, and the light chain variable domain comprises a CDR3 region comprising SEQ ID NO: 44, a CDR2 region comprising SEQ ID NO:45, and a CDR1 region comprising SEQ ID NO:46.

In one embodiment the antibody binding to human CSF-1R binds to human CSF-1R fragment delD4 (SEQ ID NO: 65) and to human CSF-1R-ECD (SEQ ID NO: 64) with a ratio of 1:50 or lower, further does not bind to human CSF-1R fragment D1-D3 (SEQ ID NO: 66).

One embodiment of the invention is a screening method for selecting antibodies according to the invention comprising the following steps:

a) determining the binding signal (Response Units (RU)) of anti-CSF-1R antibodies to human CSF-1R fragment delD4 (SEQ ID NO: 65) and to human CSF1R Extracellular Domain (CSF-1R-ECD) (SEQ ID NO: 64) by a Surface Plasmon Resonance assay (Biacore assay).

h) selecting antibodies with ratio of the binding signals (human CSF-1R fragment delD4/human CSF-1R Extracellular Domain (CSF-1R-ECD)) of 50:1 or lower.

In one embodiment the determination is performed at 25° C.

In one embodiment the screening method comprises as further steps the measuring of the binding of anti-CSF-1R antibodies to human CSF-1R fragment D1-D3 (SEQ ID NO: 66) (D1-D3) and the selecting of antibodies which show no binding to said fragment.

In one embodiment the antibodies according to the invention inhibit CSF-1 binding to CSF-1R. In one embodiment with an IC50 of 200 ng/ml or lower, in one embodiment with an IC50 of 50 ng/ml or lower. The IC50 of inhibition of CSF-1 binding to CSF-1R can be determined as shown in Example 2.

In one embodiment the antibodies according to the invention inhibit CSF-1-induced CSF-1R phosphorylation (in NIH3T3-CSF-1R recombinant cells).

In one embodiment with an IC50 of 800 ng/ml or lower, in one embodiment with an IC50 of 600 ng/ml or lower, in one embodiment with an IC50 of 250 ng/ml or lower. The IC50 of CSF-1-induced CSF-1R phosphorylation can be determined as shown in Example 3.

In one embodiment the antibodies according to the invention inhibit the growth of recombinant NIH3T3 cells expressing human CSF-1R (SEQ ID No: 62). In one embodiment with an IC50 of 10 µg/ml or lower, in one embodiment with an IC50 of 5 µg/ml or lower, in one embodiment with an IC50 of 2 µg/ml or lower. In one embodiment with an IC30 of 10 µg/ml or lower, in one embodiment with an IC30 of 5 µg/ml or lower, in one embodiment with an IC30 of 2 µg/ml or lower. The IC50 value, the IC30 value or the % growth inhibition is determined as shown in Example 5.

In one embodiment the antibodies according to the invention inhibit the growth of recombinant NIH3T3 cells expressing human mutant CSF-1R L301S Y969F (SEQ ID No: 63). In one embodiment with an IC50 of 15 µg/ml or lower, in one embodiment with an IC50 of 10 µg/ml or lower. In one embodiment with an IC30 of 10 µg/ml or lower, in one embodiment with an IC50 of 5 µg/ml ng/ml or lower; in one embodiment with an IC50 of 2 µg/ml or lower. The IC50 value, the IC30 value or the % growth inhibition is determined as shown in Example 5.

In one embodiment the antibodies according to the invention inhibit the growth of BeWo tumor cells (ATCC CCL-98) by 65% or more (at an antibody concentration of 10 µg/ml; and as compared to the absence of antibody). The % growth inhibition is determined as shown in Example 8. E.g. Mab 2F11 shows a growth inhibition of BeWo tumor cells of 70%.

In one embodiment the antibodies according to the invention inhibit (both) human and cynomolgous macrophage differentiation (which is indicated by the inhibition of the survival of human and cynomolgous monocytes as shown in Examples 7 and 8). In one embodiment the antibodies according to the invention inhibit the survival of human monocytes with an IC50 of 0.15 µg/ml or lower, in on embodiment with an IC50 of 0.10 µg/ml or lower. The inhibition of the survival, of human monocytes is determined as shown in Example 7. In one embodiment the antibodies according to the invention inhibit the survival of cynomolgous monocytes by 80% or more, in one embodiment by 90% or more (at an antibody concentration of 5 µg/ml; and as compared to the absence of antibody). The inhibition of the survival of human monocytes is determined as shown in Example 8.

A further embodiment of the invention is a method for the production of an antibody against CSF-1R wherein the sequence of a nucleic acid encoding the heavy chain of a human IgG1 class antibody binding to human CSF-1R according to the invention said modified nucleic acid and the nucleic acid encoding the light chain of said antibody are inserted into an expression vector, said vector is inserted in a eukaryotic host cell, the encoded protein is expressed and recovered from the host cell or the supernatant.

The antibodies according to the invention are preferably produced by recombinant means. Therefore the antibody is preferably an isolated monoclonal antibody. Such recombinant methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in appropriate prokaryotic or eukaryotic host cells like CHO cells, NS0 cells, SP2/0 cells, HEK293 cells, COS cells, yeast, or E.coli cells, and the antibody is recovered from the cells (supernatant or cells after lysis).

Recombinant production of antibodies is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The antibodies may be present in whole cells, in a cell lysate, or in a partially purified or substantially pure form.

Purification is performed in order to eliminate other cellular components or other contaminants, e.g. other cellular nucleic acids or proteins, by standard techniques, including alkaline/SDS treatment, CsCl handing, column chromatography, agarose gel electrophoresis, and others well known in the art. See Ausubel, F., et al., ed. Current Protocols in Molecular Biology, Greene Publishing and Wiley Interscience, New York (1987).

The monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies are readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Expression in NS0 cells is described by, e.g., Barnes, L. M., et al., Cytotechnology 32 (2000) 109-123; and Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

In some embodiments, the antibody according to the invention is of human IgG1 subclass or of human IgG4 subclass. In one embodiment the antibody according to the invention is of human IgG1 subclass. In one embodiment the antibody according to the invention is of human IgG4 subclass.

In one embodiment the constant chains are of human origin. Such constant chains are well known in the state of the art and e.g. described by Kabat, E. A., (see e.g., Johnson, G. and Wu, T. T., Nucleic Acids Res. 28 (2000) 214-218). For example, a useful human heavy chain constant region comprises an amino acid sequence of SEQ ID NO: 58. For example, a useful human light chain constant region comprises an amino acid sequence of a kappa-light chain constant region of SEQ ID NO: 57.

Another aspect of the invention is an antibody binding to human CSF-1R, wherein
 a) the heavy chain variable domain comprises SEQ ID NO:7 and the light chain variable domain comprises SEQ ID NO:8,
 b) the heavy chain variable domain comprises SEQ ID NO:15 and the light chain variable domain comprises SEQ ID NO:16;
 or a humanized version thereof.

Another aspect of the invention is an antibody binding to human CSF-1R, wherein a) the heavy chain variable domain comprises SEQ ID NO:7 and the light chain variable domain comprises SEQ ID NO:8,
b) the heavy chain variable domain comprises SEQ ID NO:15 and the light chain variable domain comprises SEQ ID NO:16;
c) the heavy chain variable domain comprises SEQ ID NO:75 and the light chain variable domain comprises SEQ ID NO:76;
d) the heavy chain variable domain comprises SEQ ID NO:83 and the light chain variable domain comprises SEQ ID NO:84;
or a humanized version thereof.

Another aspect of the invention is an antibody binding to human CSF-1R, wherein
the heavy chain variable domain comprises SEQ ID NO:7 and the light chain variable domain comprises SEQ ID NO:8, or a humanized version thereof.

Another aspect of the invention is an antibody binding to human CSF-1R, wherein
a) the heavy chain variable domain comprises SEQ ID NO:23 and the light chain variable domain comprises SEQ ID NO:24, or
b) the heavy chain variable domain comprises SEQ NO:31 and the light chain variable domain comprises SEQ ID NO:32, or
c) the heavy chain variable domain comprises SEQ ID NO:39 and the light chain variable domain comprises SEQ ID NO:40, or
d) the heavy chain variable domain comprises SEQ ID NO:47 and the light chain variable domain comprises SEQ ID NO:48, or
e) the heavy chain variable domain comprises SEQ ID NO:55 and the light chain variable domain comprises SEQ ID NO:56.

Another aspect of the invention is an antibody binding to human CSF-1R, wherein
a) the heavy chain variable domain comprises SEQ ID NO:23 and the light chain variable domain comprises SEQ ID NO:24, or
b) the heavy chain variable domain comprises SEQ ID NO:31 and the light chain variable domain comprises SEQ ID NO:32, or
c) the heavy chain variable domain comprises SEQ ID NO:39 and the light chain variable domain comprises SEQ NO:40, or
d) the heavy chain variable domain comprises SEQ ID NO:47 and the light chain variable domain comprises SEQ ID NO:48.

Another aspect of the invention is an antibody binding to human CSF-1R, wherein
the heavy chain variable domain comprises SEQ ID NO:23 and the light chain variable domain comprises SEQ ID NO:24, or Another aspect of the invention is an antibody binding to human CSF-1R, wherein the heavy chain variable domain comprises SEQ ID NO:31 and the light chain variable domain comprises SEQ ID NO:32.

Another aspect of the invention is an antibody binding to human CSF-1R, wherein
the heavy chain variable domain comprises SEQ ID NO:39 and the light chain variable domain comprises SEQ ID NO:40, Another aspect of the invention is an antibody binding to human CSF-1R, wherein
the heavy chain variable domain comprises SEQ ID NO:47 and the light chain variable domain comprises SEQ ID NO:48.

Another aspect of the invention is an antibody binding to human CSF-1R, wherein
the heavy chain variable domain comprises SEQ ID NO:15 and the light chain variable domain comprises SEQ ID NO:16, or a humanized version thereof.

Another aspect of the invention is an antibody binding to human CSF-1R, wherein
the heavy chain variable domain comprises SEQ ID NO:75 and the light chain variable domain comprises SEQ ID NO:76;
or a humanized version thereof.

Another aspect of the invention is an antibody binding to human CSF-1R, wherein
the heavy chain variable domain comprises SEQ ID NO:83 and the light chain variable domain comprises SEQ ID NO:84;
or a humanized version thereof.

Another aspect of the invention is an antibody binding to human CSF-1R, wherein
a) the heavy chain variable domain comprises a CDR3 region comprising SEQ ID NO:1, a CDR2 region comprising SEQ ID NO: 2, and a CDR1 region comprising SEQ ID NO:3, and the light chain variable domain comprises a CDR3 region comprising SEQ ID NO: 4, a CDR2 region comprising SEQ ID NO:5, and a CDR1 region comprising SEQ ID NO:6, or,
b) the heavy chain variable domain comprises a CDR3 region comprising SEQ ID NO: 9, a CDR2 region comprising SEQ ID NO: 10, and a CDR1 region comprising SEQ ID NO: 11, and the light chain variable domain comprises a CDR3 region comprising SEQ ID NO:12, a CDR2 region comprising SEQ ID NO: 13, and a CDR1 region comprising SEQ ID NO: 14, or
c) the heavy chain variable domain comprises a CDR3 region comprising SEQ ID NO: 17, a CDR2 region comprising SEQ ID NO: 18, and a CDR1 region comprising SEQ ID NO:19, and the light chain variable domain comprises a CDR3 region comprising SEQ ID NO: 20, a CDR2 region comprising SEQ ID NO:21, and a CDR1 region comprising SEQ ID NO:22, or
d) the heavy chain variable domain comprises a CDR3 region comprising SEQ ID NO: 25, a CDR2 region comprising SEQ ID NO: 26, and a CDR1 region comprising SEQ ID NO: 27, and the light chain variable domain comprises a CDR3 region comprising SEQ ID NO:28, a CDR2 region comprising SEQ ID NO: 29, and a CDR1 region comprising SEQ ID NO: 30, or
e) the heavy chain variable domain comprises a CDR3 region comprising SEQ ID NO: 33, a CDR2 region comprising SEQ ID NO: 34, and a CDR1 region comprising SEQ ID NO: 35, and the light chain variable domain comprises a CDR3 region comprising SEQ ID NO:36, a CDR2 region comprising SEQ ID NO: 37, and a CDR1 region comprising SEQ ID NO: 38, or
f) the heavy chain variable domain comprises a CDR3 region comprising SEQ ID NO:41, a CDR2 region comprising SEQ ID NO: 42, and a CDR1 region comprising SEQ ID NO:43, and the light chain variable domain comprises a CDR3 region comprising SEQ ID NO: 44, a CDR2 region comprising SEQ ID NO:45, and a CDR1 region comprising SEQ ID NO:46, g) the heavy chain variable domain comprises a CDR3 region comprising SEQ ID NO: 49, a CDR2 region comprising SEQ ID NO: 50, and a CDR1 region comprising SEQ ID NO: 51, and the light chain variable domain comprises a CDR3 region comprising SEQ ID NO:52, a CDR2 region comprising SEQ ID NO: 53, and a CDR1 region comprising SEQ ID NO: 54;

h) the heavy chain variable domain comprises a CDR3 region comprising SEQ ID NO:69, a CDR2 region comprising SEQ ID NO: 70, and a CDR1 region comprising SEQ ID NO:71, and the light chain variable domain comprises a CDR3 region comprising SEQ ID NO: 72, a CDR2 region comprising SEQ ID NO:73, and a CDR1 region comprising SEQ ID NO:74, or i) the heavy chain variable domain comprises a CDR3 region comprising SEQ ID NO: 77, a CDR2 region comprising SEQ ID NO: 78, and a CDR1 region comprising SEQ ID NO: 79, and the light chain variable domain comprises a CDR3 region comprising SEQ ID NO:80, a CDR2 region comprising SEQ ID NO: 81, and a CDR1 region comprising SEQ ID NO: 82.

Another aspect of the invention is an antibody binding to human CSF-1R, wherein
a) the heavy chain variable domain comprises a CDR3 region comprising SEQ ID NO: 17, a CDR2 region comprising SEQ ID NO: 18, and a CDR1 region comprising SEQ ID NO: 19, and the light chain variable domain comprises a CDR3 region comprising SEQ ID NO: 20, a CDR2 region comprising SEQ ID NO:21, and a CDR1 region comprising SEQ ID NO:22, or
b) the heavy chain variable domain comprises a CDR3 region comprising SEQ ID NO: 25, a CDR2 region comprising SEQ ID NO: 26, and a CDR1 region comprising SEQ ID NO: 27, and the light chain variable domain comprises a CDR3 region comprising SEQ ID NO:28, a CDR2 region comprising SEQ ID NO: 29, and a CDR1 region comprising SEQ ID NO: 30, or
c) the heavy chain variable domain comprises a CDR3 region comprising SEQ ID NO: 33, a CDR2 region comprising SEQ ID NO: 34, and a CDR1 region comprising SEQ ID NO: 35, and the light chain variable domain comprises a CDR3 region comprising SEQ ID NO:36, a CDR2 region comprising SEQ ID NO: 37, and a CDR1 region comprising SEQ ID NO: 38, or
d) the heavy chain variable domain comprises a CDR3 region comprising SEQ NO:41, a CDR2 region comprising SEQ ID NO: 42, and a CDR1 region comprising SEQ ID NO:43, and the light chain variable domain comprises a CDR3 region comprising SEQ ID NO: 44, a CDR2 region comprising SEQ ID NO:45, and a CDR1 region comprising SEQ ID NO:46, or
e) the heavy chain variable domain comprises a CDR3 region comprising SEQ ID NO: 49, a CDR2 region comprising SEQ ID NO: 50, and a CDR1 region comprising SEQ ID NO: 51, and the light chain variable domain comprises a CDR3 region comprising SEQ ID NO:52, a CDR2 region comprising SEQ ID NO: 53, and a CDR1 region comprising SEQ ID NO: 54.

Another aspect of the invention is an antibody binding to human CSF-1R, wherein
a) the heavy chain variable domain comprises a CDR3 region comprising SEQ ID NO: 17, a CDR2 region comprising SEQ ID NO: 18, and a CDR1 region comprising SEQ ID NO: 19, and the light chain variable domain comprises a CDR3 region comprising SEQ ID NO: 20, a CDR2 region comprising SEQ NO:21, and a CDR1 region comprising SEQ ID NO:22, or
b) the heavy chain variable domain comprises a CDR3 region comprising SEQ ID NO: 25, a CDR2 region comprising SEQ ID NO: 26, and a CDR1 region comprising SEQ ID NO: 27, and the light chain variable domain comprises a CDR3 region comprising SEQ ID NO:28, a CDR2 region comprising SEQ ID NO: 29, and a CDR1 region comprising SEQ ID NO: 30, or
c) the heavy chain variable domain comprises a CDR3 region comprising SEQ ID NO: 33, a CDR2 region comprising SEQ ID NO: 34, and a CDR1 region comprising SEQ ID NO: 35, and the light chain variable domain comprises a CDR3 region comprising SEQ NO:36, a CDR2 region comprising SEQ ID NO: 37, and a CDR1 region comprising SEQ ID NO: 38, or
d) the heavy chain variable domain comprises a CDR3 region comprising SEQ ID NO:41, a CDR2 region comprising SEQ ID NO: 42, and a CDR1 region comprising SEQ ID NO:43, and the light chain variable domain comprises a CDR3 region comprising SEQ ID NO: 44, a CDR2 region comprising SEQ ID NO:45, and a CDR1 region comprising SEQ ID NO:46.

Another aspect of the invention is an antibody binding to human CSF-1R, wherein
the heavy chain variable domain comprises a CDR3 region comprising SEQ ID NO: 17, a CDR2 region comprising SEQ ID NO: 18, and a CDR1 region comprising SEQ ID NO:19, and the light chain variable domain comprises a CDR3 region comprising SEQ ID NO: 20, a CDR2 region comprising SEQ ID NO:21, and a CDR1 region comprising SEQ ID NO:22.

Another aspect of the invention is an antibody binding to human CSF-1R, wherein
the heavy chain variable domain comprises a CDR3 region comprising SEQ ID NO: 25, a CDR2 region comprising SEQ ID NO: 26, and a CDR1 region comprising SEQ ID NO: 27, and the light chain variable domain comprises a CDR3 region comprising SEQ ID NO:28, a CDR2 region comprising SEQ ID NO: 29, and a CDR1 region comprising SEQ ID NO: 30.

Another aspect of the invention is an antibody binding to human CSF-1R, wherein
the heavy chain variable domain comprises a CDR3 region comprising SEQ ID NO: 33, a CDR2 region comprising SEQ ID NO: 34, and a CDR1 region comprising SEQ ID NO: 35, and the light chain variable domain comprises a CDR3 region comprising SEQ ID NO:36, a CDR2 region comprising SEQ ID NO: 37, and a CDR1 region comprising SEQ ID NO: 38.

Another aspect of the invention is an antibody binding to human CSF-1R, wherein
the heavy chain variable domain comprises a CDR3 region comprising SEQ ID NO:41, a CDR2 region comprising SEQ ID NO: 42, and a CDR1 region comprising SEQ ID NO:43, and the light chain variable domain comprises a CDR3 region comprising SEQ ID NO: 44, a CDR2 region comprising SEQ ID NO:45, and a CDR1 region comprising SEQ ID NO:46.

The invention comprises a method for the treatment of a patient in need of therapy, comprising administering to the patient a therapeutically effective amount of an antibody according to the invention.

The invention comprises the use of an antibody according to the invention for therapy.

One preferred embodiment of the invention are the CSF-1R antibodies of the present invention for use in the treatment of "CSF-1R mediated diseases" or the CSF-1R antibodies of the present invention for use for the manufacture of a medicament in the treatment of "CSF-1R mediated diseases", which can be described as follows:

There are 3 distinct mechanisms by which CSF-1R signaling is likely involved in tumor growth and metastasis. The first is that expression of CSF-ligand and receptor has been found in tumor cells originating in the female reproductive system (breast, ovarian, endometrium, cervical) (Scholl, S. M., et al, J. Natl. Cancer Inst. 86 (1994) 120-126; Kacinski, B. M., Mol. Reprod. Dev. 46 (1997) 71-74; Ngan, H. Y., et al., Eur. J. Cancer 35 (1999) 1546-1550; Kirma, N., et al., Cancer Res 67 (2007) 1918-1926) and the expression has been associated with breast cancer xenograft growth as well as poor prognosis in breast cancer patients. Two point mutations were seen in CSF-1R in about 10-20% of acute myelocytic leukemia, chronic myelocytic leukemia and myelodysplasia patients tested in one study, and one of the mutations was found to disrupt receptor turnover (Ridge, S. A., et al., Proc. Natl. Acad. Sci USA 87 (1990) 1377-1380). However the incidence of the mutations could not be confirmed in later studies (Abu-Duhier, F. M., et al., Br. J. Haematol. 120 (2003) 464-470). Mutations were also found in some cases of hepatocellular cancer (Yang, D. H., et al., Hepatobiliary Pancreat. Dis. Int. 3 (2004) 86-89) and idiopathic myelofibrosis (Abu-Duhier, F. M., et al., Br. J. Haematol. 120 (2003) 464-470). Recently, in the GDM-1 cell line derived from a patient with myelomonoblastic leukemia the Y571D mutation in CSF-1R was identified (Chase, A., et al., Leukemia 23 (2009) 358-364).

Pigmented villonodular synovitis (PVNS) and Tenosynovial Giant cell tumors (TGCT) can occur as a result of a translocation that fuses the M-CSF gene to a collagen gene COL6A3 and results in overexpression of M-CSF (West, R. B., et al., Proc. Natl. Acad. Sci. USA 103 (2006) 690-695). A landscape effect is proposed to be responsible for the resulting tumor mass that consists of monocytic cells attracted by cells that express M-CSF. TGCTs are smaller tumors that can be relatively easily removed from fingers where they mostly occur. PVNS is more aggressive as it can recur in large joints and is not as easily controlled surgically.

The second mechanism is based on blocking signaling through M-CSF/CSF-1R at metastatic sites in bone which induces osteoclastogenesis, bone resorption and osteolytic bone lesions. Breast, multiple myeloma and lung cancers are examples of cancers that have been found to metastasize to the bone and cause osteolytic bone disease resulting in skeletal complications. M-CSF released by tumor cells and stroma induces the differentiation of hematopoietic myeloid monocyte progenitors to mature osteoclasts in collaboration with the receptor activator of nuclear factor kappa-B ligand-RANKL. During this process, M-CSF acts as a permissive factor by giving the survival signal to osteoclasts (Tanaka, S., et al., J. Clin. Invest. 91 (1993) 257-263). Inhibition of CSF-1R activity during osteoclast differentiation and maturation with a anti-CSF-1R antibody is likely to prevent unbalanced activity of osteoclasts that cause osteolytic disease and the associated skeletal related events in metastatic disease. Whereas breast, lung cancer and multiple myeloma typically result in osteolytic lesions, metastasis to the bone in prostate cancer initially has an osteoblastic appearance in which increased bone forming activity results in 'woven bone' which is different from typical lamellar structure of normal bone. During disease progression bone lesions display a significant osteolytic component as well as high serum levels of bone resorption and suggests that anti-resorptive therapy may be useful. Bisphosphonates have been shown to inhibit the formation of osteolytic lesions and reduced the number of skeletal-related events only in men with hormone-refractory metastatic prostate cancer but at this point their effect on osteoblastic lesions is controversial and bisphosphonates have not been beneficial in preventing bone metastasis or hormone responsive prostate cancer to date. The effect of anti-resorptive agents in mixed osteolytic/osteoblastic prostate cancer is still being studied in the clinic (Choueiri, M. B., et al., Cancer Metastasis Rev. 25 (2006) 601-609; Vessella R. L. and Corey, E., Clin. Cancer Res. 12 (20 Pt 2) (2006) 6285s-6290s).

The third mechanism is based on the recent observation that tumor associated macrophages (TAM) found in solid tumors of the breast, prostate, ovarian and cervical cancers correlated with poor prognosis (Bingle, L., et al., J. Pathol. 196 (2002) 254-265; Pollard, J. W., Nat. Rev. Cancer 4 (2004) 71-78). Macrophages are recruited to the tumor by M-CSF and other chemokines. The macrophages can then contribute to tumor progression through the secretion of angiogenic factors, proteases and other growth factors and cytokines and may be blocked by inhibition of CSF-1R signaling. Recently it was shown by Zins et al (Zins, K., et al., Cancer Res. 67 (2007) 1038-1045) that expression of siRNA of Tumor necrosis factor alpha (TNF alpha), M-CSF or the combination of both would reduce tumor growth in a mouse xenograft model between 34% and 50% after intratumoral injection of the respective siRNA. SiRNA targeting the TNF alpha secreted by the human SW620 cells reduced mouse M-CSF levels and led to reduction of macrophages in the tumor. In addition treatment of MCF7 tumor xenografts with an antigen binding fragment directed against M-CSF did result in 40% tumor growth inhibition, reversed the resistance to chemotherapeutics and improved survival of the mice when given in combination with chemotherapeutics (Paulus, P., et al., Cancer Res. 66 (2006) 4349-4356).

TAMs are only one example of an emerging link between chronic inflammation and cancer. There is additional evidence for a link between inflammation and cancer as many chronic diseases are associated with an increased risk of cancer, cancers arise at sites of chronic inflammation, chemical mediators of inflammation are found in many cancers; deletion of the cellular or chemical mediators of inflammation inhibits development of experimental cancers and long-term use of anti-inflammatory agents reduce the risk of some cancers. A link to cancer exists for a number of inflammatory conditions among—those *H.pylori* induced gastritis for gastric cancer, Schistosomiasis for bladder cancer, HHVX for Kaposi's sarcoma, endometriosis for ovarian cancer and prostatitis for prostate cancer (Balkwill, F., et al., Cancer Cell 7 (2005) 211-217). Macrophages are key cells in chronic inflammation and respond differentially to their microenvironment. There are two types of macrophages that are considered extremes in a continuum of functional states: M1 macrophages are involved in Type 1 reactions. These reactions involve the activation by microbial products and consequent killing of pathogenic microorganisms that result in reactive oxygen intermediates. On the other end of the extreme are M2 macrophages involved in Type 2 reactions that promote cell proliferation, tune inflammation and adaptive immunity and promote tissue remodeling, angiogenesis and repair (Mantovani, A., et al., Trends Immunol. 25 (2004) 677-686). Chronic inflammation resulting in established neoplasia is usually associated with M2 macrophages. A pivotal cytokine that mediates inflammatory reactions is TNF alpha that true to its name can stimulate anti-tumor immunity and hemorrhagic necrosis at high doses but has also recently been found to be expressed by tumor cells and acting as a tumor promoter (Zins, K., et al., Cancer Res. 67 (2007) 1038-1045; Balkwill, F., Cancer Metastasis Rev. 25 (2006) 409-416). The specific role of macrophages with respect to the tumor still needs to be better understood including the potential spatial and temporal dependence on their function and the relevance to specific tumor types.

Thus one embodiment of the invention are the CSF-1R antibodies of the present invention for use in the treatment of cancer. The term "cancer" as used herein may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra., cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers. Preferably such cancer is a breast cancer, ovarian cancer, cervical cancer, lung cancer or prostate cancer. Preferably such cancers are further characterized by CSF-1 or CSF-1R expression or overexpression. One further embodiment the invention are the CSF-1R antibodies of the present invention for use in the simultaneous treatment of primary tumors and new metastases.

Thus another embodiment of the invention are the CSF-1R antibodies of the present invention for use in the treatment of periodontitis, histiocytosis X. osteoporosis, Paget's disease of bone (PDB), bone loss due to cancer therapy, periprosthetic osteolysis, glucocorticoid-induced osteoporosis, rheumatoid arthritis, psiratic arthritis, osteoarthritis, inflammatory arthridities, and inflammation.

Rabello, D., et al., Biochem. Biophys. Res. Commun. 347 (2006) 791-796 has demonstrated that SNPs in the CSF1 gene exhibited a positive association with aggressive periodontitis: an inflammatory disease of the periodontal tissues that causes tooth loss due to resorption of the alveolar bone.

Histiocytosis X (also called Langerhans cell histiocytosis, LCH) is a proliferative disease of Langerhans dendritic cells that appear to differentiate into osteoclasts in bone and extra osseous LCH lesions. Langerhans cells are derived from circulating monocytes. Increased levels of M-CSF that have been measured in sera and lesions where found to correlate with disease severity (da Costa, C. E., et al., J. Exp. Med. 201 (2005) 687-693). The disease occurs primarily in a pediatric patient population and has to be treated with chemotherapy when the disease becomes systemic or is recurrent.

The pathophysiology of osteoporosis is mediated by loss of bone forming osteoblasts and increased osteoclast dependent bone resorption. Supporting data has been described by Cenci et al showing that an anti-M-CSF antibody injection preserves bone density and inhibits bone resorption in ovariectomized mice (Cenci, S., et al., J. Clin. Invest. 105 (2000) 1279-1287). Recently a potential link between postmenopausal bone loss due to estrogen deficiency was identified and found that the presence of TNF alpha producing T-cell affected bone metabolism (Roggia, C., et al., Minerva Med. 95 (2004) 125-132). A possible mechanism could be the induction of M-CSF by TNF: alpha in vivo. An important role for M-CSF in TNF-alpha-induced osteoclastogenesis was confirmed by the effect of an antibody directed against. M-CSF that blocked the TNF alpha induced osteolysis in mice and thereby making inhibitors of CSF-1R signaling potential targets for inflammatory arthritis (Kitaura, H., et al., J. Clin. Invest. 115 (2005) 3418-3427).

Paget's disease of bone (PDB) is the second most common bone metabolism disorder after osteoporosis in which focal abnormalities of increased bone turnover lead to complications such as bone pain, deformity, pathological fractures and deafness. Mutations in four genes have been identified that regulate normal osteoclast function and predispose individuals to PDB and related disorders: insertion mutations in TNFRSF11A, which encodes receptor activator of nuclear factor (NT) kappaB (RANK)-a critical regulator of osteoclast function, inactivating mutations of TNFRSF11B which encodes osteoprotegerin (a decoy receptor for RANK ligand), mutations of the sequestosome I gene (SQSTM41), which encodes an important scaffold protein in the NFkappaB pathway and mutations in the valosin-containing protein (VCP) gene. This gene encodes VCP, which has a role in targeting the inhibitor of NFkappaB for degradation by the proteasome (Daroszewska. A. and Ralston, S. H., Nat. Clin. Pract. Rheumatol. 2 (2006) 270-277). Targeted CSF-1R inhibitors provide an opportunity to block the deregulation of the RANKL signaling indirectly and add an additional treatment option to the currently used bisphosphonates.

Cancer therapy induced bone loss especially in breast and prostate cancer patients is an additional indication where a targeted CSF-1R inhibitor could prevent bone loss (Lester, J. E., et al., Br. J. Cancer 94 (2006) 30-35). With the improved prognosis for early breast cancer the long-term, consequences of the adjuvant therapies become more important as some of the therapies including chemotherapy, irradiation, aromatase inhibitors and ovary ablation affect bone metabolism by decreasing the bone mineral density, resulting in increased risk for osteoporosis and associated fractures (Lester, J. E., et al., Br. J. Cancer 94 (2006) 30-35). The equivalent to adjuvant aromatase inhibitor therapy in breast cancer is androgen ablation therapy in prostate cancer which leads to loss of bone mineral density and significantly increases the risk of osteoporosis-related fractures (Stoch, S. A., et al., J. Clin. Endocrinol. Metab. 86 (2001) 2787-2791).

Targeted inhibition of CSF-1R signaling is likely to be beneficial in other indications as well when targeted cell types include osteoclasts and macrophages e.g. treatment of specific complications in response to joint replacement as a consequence of rheumatoid arthritis. Implant failure due to periprosthetic bone loss and consequent loosing of prostheses is a major complication of joint replacement and requires repeated surgery with high socioeconomic burdens for the individual patient and the health-care system. To date, there is no approved drug therapy to prevent or inhibit periprosthetic osteolysis (Drees, P., et al., Nat. Clin. Pract. Rheumatol. 3 (2007) 165-171).

Glucocorticoid-induced osteoporosis (GIOP) is another indication in which a CSF-1R inhibitor could prevent bone loss after longterm glucocorticocosteroid use that is given as a result of various conditions among those chronic obstructive pulmonary disease, asthma and rheumatoid arthritis (Guzman-Clark, J. R., et al., Arthritis Rheum. 57 (2007) 140-146; Feldstein, A. C., et al., Osteoporos. Int. 16 (2005) 2168-2174).

Rheumatoid arthritis, psioratic arthritis and inflammatory arthridities are in itself potential indications for CSF-1R signaling inhibitors in that they consist of a macrophage component and to a varying degree bone destruction (Ritchlin, C. T., et al., J. Clin. Invest. 111 (2003) 821-831). Osteoarthritis and rheumatoid arthritis are inflammatory autoimmune disease caused by the accumulation of macrophages in the connective tissue and infiltration of macrophages into the synovial fluid, which is at least partially mediated by M-CSF. Campbell, I., K., et al., J. Leukoc, Biol. 68 (2000) 144-150, demonstrated that M-CSF is produced by human-joint tissue cells (chondrocytes, synovial fibroblasts) in vitro and is found in synovial fluid of patients with rheumatoid arthritis, suggesting that it contributes to the synovial tissue proliferation and macrophage infiltration which is associated with the pathogenesis of the disease. Inhibition of CSF-1R signaling is likely to control the number of macrophages in the joint and alleviate the pain from the associated bone destruction. In order to minimize adverse affects and to further understand the impact of the CSF-1R signaling in these indications, one method is to specifically inhibit CSF-1R without targeting a myriad other kinases, such as Raf kinase.

Recent literature reports correlate increased circulating M-CSF with poor prognosis and atherosclerotic progression in chronic coronary artery disease (Saitoh, T., et al., J. Am. Coll. Cardiol. 35 (2000) 655-665; Ikonomidis, I., et al., Eur. Heart. J. 26 (2005) p. 1618-1624); M-CSF influences the atherosclerotic process by aiding the formation of foam cells (macrophages with ingested oxidized LDL) that express CSF-1R and represent the initial plaque (Murayama, T., et al., Circulation 99 (1999) 1740-1746).

Expression and signaling of M-CSF and CSF-1R is found in activated microglia. Microglia, which are resident macrophages of the central nervous system, can he activated by various insults, including infection and traumatic injury, M-CSF is considered a key regulator of inflammatory responses in the brain and M-CSF levels increase in HIV-1, encephalitis, Alzheimer's disease (AD) and brain tumors. Microgliosis as a consequence of autocrine signaling by M-CSF/CSF-1R results in induction of inflammatory cytokines and nitric oxides being released as demonstrated by e.g. using an experimental neuronal damage model (Hao, A. J., et al., Neuroscience 112 (2002) 889-900; Murphy, G. M., Jr., et al., J. Biol. Chem. 273 (1998) 20967-20971). Microglia that have increased expression of CSF-1R are found to surround plaques in AD and in the amyloid precursor protein V717F transgenic mouse model of AD (Murphy, G. M, Jr., et al., Am. J. Pathol. 157 (2000) 895-904). On the other hand op/op mice with fewer microglia in the brain resulted in fibrilar deposition of A-beta and neuronal loss compared to normal control suggesting that microglia do have a neuroprotective function in the development of AD lacking in the op/op mice (Kaku, M., et al., Brain Res. Brain Res. Protoc. 12 (2003) 104-108).

Expression and signaling of M-CSF and CSF-1R is associated with inflammatory bowel disease (IBD) (WO 2005/046657). The term "inflammatory bowel disease" refers to serious, chronic disorders of the intestinal tract characterized by chronic inflammation at various sites in the gastrointestinal tract, and specifically includes ulcerative colitis (UC) and Crohn's disease.

The invention comprises an antibody binding to human CSF-1R comprising the above mentioned epitope binding properties or alternatively by the above mentioned amino acid sequences and amino acid sequence fragments for the treatment of cancer.

The invention comprises an antibody binding to human CSF-1R comprising the above mentioned epitope binding properties or alternatively by the above mentioned amino acid sequences and amino acid sequence fragments for the treatment of bone loss.

The invention comprises an antibody binding to human CSF-1R comprising the above mentioned epitope binding properties or alternatively by the above mentioned amino acid sequences and amino acid sequence fragments for the prevention or treatment of metastasis.

The invention comprises an antibody binding to human CSF-1R comprising the above mentioned epitope binding properties or alternatively by the above mentioned amino acid sequences and amino acid sequence fragments for treatment of inflammatory diseases.

The invention comprises the use of an antibody comprising the antibody binding to human CSF-1R, wherein the antibody comprises the above mentioned epitope binding properties or alternatively by the above mentioned amino acid sequences and amino acid sequence fragments for the treatment of cancer or alternatively for the manufacture of a medicament for the treatment of cancer.

The invention comprises the use of an antibody comprising the antibody binding to human CSF-1R, wherein the antibody comprises the above mentioned epitope binding properties or alternatively by the above mentioned amino acid sequences and amino acid sequence fragments for the treatment of bone loss or alternatively for the manufacture of a medicament for the treatment of bone loss.

The invention comprises the use of an antibody comprising the antibody binding to human CSF-1R, wherein the antibody comprises the above mentioned epitope binding properties or alternatively by the above mentioned amino acid sequences and amino acid sequence fragments for the prevention or treatment of metastasis or alternatively for the manufacture of a medicament for the prevention or treatment of metastasis.

The invention comprises the use of an antibody comprising the antibody binding to human CSF-1R, wherein the antibody comprises the above mentioned epitope binding properties or alternatively by the above mentioned amino acid sequences and amino acid sequence fragments for treatment of inflammatory diseases or alternatively for the manufacture of a medicament for the treatment of inflammatory diseases.

A further embodiment of the invention is a method for the production of an antibody against CSF-1R wherein the sequence of a nucleic acid encoding the heavy chain of a human IgG1 class antibody binding to human CSF-1R according to the invention said modified nucleic acid and the nucleic acid encoding the light chain of said antibody are inserted into an expression vector, said vector is inserted in a eukaryotic host cell, the encoded protein is expressed and recovered from the host cell or the supernatant.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or E. coli cells, and the antibody is recovered from the cells (from the supernatant or after cells lysis).

Recombinant production of antibodies is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The antibodies may be present in whole cells, in a cell lysate, or in a partially purified, or substantially pure form. Purification is performed in order to eliminate other cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley interscience, New York (1987).

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; Norderhaug, L., et al., J. Immunol. Methods 204 (1997) 77-87. A preferred transient expression system (FMK 293) is described by Schlaeger, E.-J. and Christensen. K., in Cytotechnology 30 (1999) 71-83, and by Schlaeger, E.-J., in J. Immunol. Methods 194 (1996) 191-199.

Nucleic acid molecules encoding amino acid sequence variants of anti-CSF-1R antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-CSF-1R antibody.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

In another aspect, the present invention provides a composition, e.g. a pharmaceutical composition, containing one or a combination of monoclonal. antibodies, or the antigen-binding portion thereof, of the present invention, formulated together with a pharmaceutically acceptable carrier.

As used herein, "pharmaceutically acceptable carrier" includes any and all solvents, dispersion media, coatings, antibacterial and antifungal agents, isotonic and absorption/resorption delaying agents, and the like that are physiologically compatible. Preferably, the carrier is suitable for injection or infusion.

A composition of the present invention can be administered by a variety of methods known in the art. As will be appreciated by the skilled artisan, the route and/or mode of administration will vary depending upon the desired results.

Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient (effective amount). The selected dosage level will depend upon a variety of pharmacokinetic factors including the activity of the particular compositions of the present invention employed, or the ester, salt or amide thereof, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

The invention comprises the use of the antibodies according to the invention for the treatment of a patient suffering from cancer, especially from colon, lung or pancreas cancer.

The invention comprises also a method for the treatment of a patient suffering from such disease.

The invention further provides a method for the manufacture of a pharmaceutical composition comprising an effective amount of an antibody according to the invention together with a pharmaceutically acceptable carrier and the use of the antibody according to the invention for such a method.

The invention further provides the use of an antibody according to the invention in an effective amount for the manufacture of a pharmaceutical agent, preferably together with a pharmaceutically acceptable carrier, for the treatment of a patient suffering from cancer.

The invention also provides the use of an antibody according to the invention in an effective amount for the manufacture of a pharmaceutical agent, preferably together with a pharmaceutically acceptable carrier, for the treatment of a patient suffering from cancer.

EXAMPLES

The examples and figures are provided to aid the understanding of the present invention, the true scope of which is set forth in the appended claims. It is understood that modifications can be made in the procedures set forth without departing from the spirit of the invention.

Example 1

Generation of a Hybridoma Cell Line Producing Anti-CSF-1R Antibodies

Immunization Procedure of NMRI Mice

NMRI mice were immunized with an expression vector pDisplay™ (Invitrogen, USA) encoding the extracellular domain of huCSF-1R by utilizing electroporation. Every mouse was 4 times immunized with 100 µg DNA. When serum titers of anti-huCSF-1R were found to be sufficient, mice were additionally boosted once with 50 µg of a 1:1 mixture huCSF-1R ECD/huCSF-1R ECDhuFc chimera in 200 µl PBS intravenously (i.v.) 4 and 3 days before fusion.

Antigen Specific ELISA

Anti-CSF-1R titers in sera of immunized mice were determined by antigen specific ELISA.

0.3 µg/ml huCSF-1R-huFc chimera (soluble extracellular domain) was captured on a streptavidin plate (MaxiSorb; MicroCoat, DE, Cat.No. 11974998/MC1099) with 0.1 mg/ml biotinylated anti Fcγ (Jackson ImmunoResearch., Cat.No. 109-066-098) and horse radish peroxidase (HRP)-conjugated F(ab')$_2$ anti mouse IgG (GE Healthcare, UK, Cat.No.NA9310V) diluted 1/800 in PBS/005% Tween20/0.5% BSA was added. Sera from all taps were diluted 1/40 in PBS/0.05% Tween20/0.5% BSA and serially diluted up to 1/1638400. Diluted sera were added to the wells. Pre-tap serum was used as negative control. A dilution series of mouse anti-human CSF-1R Mab3291 (R&D Systems, UK) from 500 ng/ml to 0.25 ng/ml was used as positive control. All components were incubated together for 1.5 hours, Wells were washed 6 times with PBST (PBS/0.2% Tween20) and assays were developed with freshly prepared ABTS® solution (1 mg/ml) (ABTS: 2,2'-azino bis (3-ethylbenzthiazoline-6-sulfonic acid) for 10 minutes at RT. Absorbance was measured at 405 nm.

Hybridoma Generation

The mouse lymphocytes can be isolated and fused with a mouse myeloma cell line using PEG based standard protocols to generate hybridomas. The resulting hybridomas are then screened for the production of antigen-specific antibodies. For example, single cell suspensions of splenic derived lymphocytes from immunized mice are fused to Ag8 non-secreting mouse myeloma cells P3X63Ag8.653 (ATCC, CRL-1580) with 50% PEG. Cells are plated at approximately $10^4$ in flat bottom 96 well micro titer plate, followed by about two weeks incubation in selective medium. Individual wells are then screened by ELISA for human anti-CSF-1R monoclonal 104 and IgG antibodies. Once extensive hybridoma growth occurs, the antibody secreting hybridomas are replated, screened again, and if still positive for human IgG, anti-CSF-1R monoclonal antibodies, can he subcloned by FACS. The stable subclones are then cultured in vitro to produce antibody in tissue culture medium for characterization. Antibodies according to the invention could be selected using the determination of the binding of anti-CSF-1R antibodies to human CSF-1R fragment delD4 and to human CSF-1R Extracellular Domain (CSF-1R-ECD) as described in Example 4, as well as the determination of growth inhibition of NIH3T3 cells transfected with wildtype CSF-1R (ligand dependent signalling) or mutant CSF-1R L301S Y969F (ligand independent signalling) under treatment with anti-CSF-1R monoclonal antibodies as described in Example 5.

Culture of Hybridomas

Generated muMAb hybridomas were cultured in RPMI 1640 (PAN—Catalogue No. (Cat. No.) PO4-17500) supplemented with 2 mM L-glutamine (GIBCO—Cat. No. 35050-038), 1 mM Na-Pyruvat (GIBCO—Cat. No. 11360-039), 1× NEAA (GIBCO—Cat. No. 11140-035), 10% FCS (PAA—Cat. NoA15-649), 1× Pen Strep (Roche Cat. No. 1074440), 1× Nutridoma CS (Roche—Cat. No.1363743), 50 µM Mercaptoethanol (GIBCO—Cat. No.31350-010) and 50 U/ml IL 6 mouse (Roche—Cat. No. 1 444 581) at 37° C. and 5% $CO_2$. Some of the resulting mouse antibodies have been humanized (e.g. Mab 2F11) and been expressed recombinantly.

Example 2

Inhibition of CSF-1 Binding to CSF-1R (ELISA)

By setting-up this assay to first allow for anti-CSF-1R antibody binding to the CSF-1R-ECD followed by detection of ligand not bound to the receptor both-ligand displacing antibodies and dimerization inhibitor anti-CSF-1R antibodies—can be tested. The test was performed on 384 well microtiter plates (MicroCoat, DE, Cat.No. 464718) at RT. After each incubation step plates were washed 3 times with PBST.

At the beginning, plates were coated with 0.5 mg/ml goat F(ab')2 biotinylated anti Fcγ (Jackson ImmunoResearch, Cat.No. 109-006-170) for 1 hour (h).

Thereafter the wells were blocked with PBS supplemented with 0.2% Tween®-20 and 2% BSA (Roche Diagnostics GmbH, DE) for 0.5 h. 75 ng/ml of huCSF-1R-huFc chimera (which forms the dimeric soluble extracellular domain of huCSF-1R) was immobilized to plate for 1 h. Then dilutions of purified antibodies in PBS/0.05% Tween20/0.5% BSA were incubated for 1 h. After adding a mixture of 3 ng/ml CSF-1 (Biomol, DE, Cat.No. 60530), 50 ng/ml biotinylated anti CSF-1 clone BAF216 (R&D Systems,UK) and 1:5000 diluted streptavidin HRP (Roche Diagnostics GmbH, DE, Cat.No. 11089153001) for 1 h the plates were washed 6 times with PBST. Anti CSF-1R SC 2-4A5 (Santa Cruz Biotechnology, US), which inhibits the ligand-receptor interaction, was used as positive control. Plates were developed with freshly prepared BM blue® POD substrate solution (BM blue®: 3,3'-5,5'-Tetramethylbenzidine, Roche Diagnostics GmbH, DE, Cat.No. 11484281001) for 30 minutes at RT. Absorbance was measured at 370 nm. A decrease of absorbance is found, if the anti-CSF-1R antibody causes a release of CSF-1 from the dimeric complex. All anti-CSF-1R antibodies showed significant inhibition of the CSF-1 interaction with CSF-1R (see Table 1). Anti CSF-1R SC 2-4A5 (Santa Cruz Biotechnology, US see also Sherr, C. J. et al., Blood 73 (1989) 1786-1793), which inhibits the ligand-receptor interaction, was used as reference control.

TABLE 1

Calculated IC50 values for the inhibition of the CSF-1/CSF-1R interaction

| CSF-1R Mab | IC50 CSF-1/CSF-1R Inhibition [ng/ml] |
|---|---|
| Mab 2F11 | 19.3 |
| Mab 2E10 | 20.6 |
| Mab 2H7 | 18.2 |
| Mab 1G10 | 11.8 |
| SC-2-4A5 | 35.2 |

Example 3

Inhibition of CSF-1-Induced CSF-1R Phosphorylation in NIH3T3-CSF-1R Recombinant Cells 4.5×10³ NTH 3T3 cells, retrovirally infected with an expression vector for full-length CSF-1R, were cultured in DMEM (PAA Cat. No. E15-011), 2 mM L-glutamine (Sigma, Cat.No.G7513, 2 mM Sodium pyruvate, 1× nonessential aminoacids, 10% FKS (PAA, Cat.NoA15-649) and 100 µg/ml PenStrep (Sigma, Cat.No. P4333 [10 mg/ml]) until they reached confluency. Thereafter cells were washed with serum-free DMEM media (PAA Cat.No.E15-011) supplemented with sodium selenite [5 ng/ml] (Sigma, Cat.No. S9133), transferrin [10 µg/ml] (Sigma, Cat.No. T8158), BSA [400 µg/ml] (Roche Diagnostics GmbH, Cat.No. 10735078), 4 mM L-glutamine (Sigma, Cat.No. G7513), 2 mM sodium pyruvate (Gibco, Cat.No. 11360), 1× nonessential aminoacids (Gibco, Cat: 11140-035), 2-mercaptoethanol [0.05 mM] (Merck, Cat.No. M7522), 100 µg/ml and PenStrep (Sigma, Cat. No. P4333) and incubated in 30 µl of the same medium for 16 hours to allow for receptor up-regulation. 10 µl of diluted anti-CSR-1R antibodies were added to the cells for 1.5 h. Then cells were stimulated with 10 µl of 100 ng/ml huM-CSF-1 (Biomol Cat.No. 60530) for 5 min. After the incubation, supernatant was removed, cells were washed twice with 80 µl of ice-cold PBS and 50 µl of freshly prepared ice-cold lysis buffer (150 mM NaCl/20 mM Tris pH 7.5/1 mM EDTA/1 mM EGTA/ 1% Triton X-100/1 protease inhibitor tablet (Roche Diagnostics GmbH Cat.No. 1 836 170) per 10 ml buffer/10 µl/ml phosphatase inhibitor cocktail 1 (Sigma Cat.No. P-2850, 100× Stock)/ 10 µl/ml protease inhibitor 1 (Sigma Cat.No.P-5726, 1.00× Stock)/10 µl/ml 1 M NaF) was added. After 30 minutes on ice the plates were shaken vigourously on a plateshaker for 3 minutes and then centrifuged 10 minutes at 2200 rpm (Heraeus Megafuge 10).

The presence of phosphorylated and total CSF-1 receptor in the cell lysate was analyzed with Elisa. For detection of the phosphorylated receptor the kit from R&D Systems (Cat. No. DYC3268-2) was used according to the instructions of the supplier. For detection of total CSF-1R 10 µl of the lysate was immobilized on plate by use of the capture antibody contained in the kit. Thereafter 1:750 diluted biotinylated anti CSF-1R antibody BAF329 (R&D Systems) and 1:1000 diluted streptavidin-HRP conjugate was added. After 60 minutes plates were developed with freshly prepared ABTS® solution and the absorbance was detected. Data were calculated as % of positive control without antibody and the ratio value phosphoitotal receptor expressed. The negative control was defined without addition of M-CSF-1. Anti CSF-1R, SC 2-4A5 (Santa Cruz Biotechnology, US, see also Sherr, C. J. et al., Blood 73 (1989) 1786-1793), which inhibits the ligand-receptor interaction, was used as reference control.

TABLE 2

Calculated IC50 values for the inhibition of CSF-1 receptor phosphorylation.

| CSF-1R Mab | IC50 CSF-1R Phosphorylation [ng/ml] |
|---|---|
| Mab 2F11 | 219.4 |
| Mab 2E10 | 752.0 |
| Mab 2H7 | 703.4 |
| Mab 1G10 | 56.6 |
| SC-2-4A5 | 1006.6 |

Example 4

Determination of the Binding of Anti-CSF-1R Antibodies to Human CSF-1R Fragment delD4 and to Human CSF-1R Extracellular Domain (CSF-1R-ECD)

Preparation of Human CSF-1R Extracellular Domain (CSF-1R-ECD) (Comprising the Extracellular Subdomains D1-D5, hCSF-1R-ECD) of SEQ ID NO: 64:

pCMV-preS-Fc-hCSF-1R-ECD (7836 bp) encodes the complete ECD of human CSF-1R (SEQ ID NO: 64) C-terminally fused to a PreScission protease cleavage site, followed by aa100-330 of human IgG1 and a 6× His-Tag, under the control of CMV promoter. The natural signal peptide has been varied by insertion of amino acids G and S after the first M, in order to create a BamHI restriction site.

Preparation of Human CSF-1R Fragment delD4 (Comprising the Extracellular Subdomains D1-D3 and D5,hCSF-1R-delD4) of SEQ ID NO: 65:

hCSF R-delD4-V1-PreSc-hFc-His was cloned from pCMV-preS-Fc-hCSF-1R-ECD by means of the Stratagene QuikChange XL site-directed mutagenesis protocol, using delD4-for with sequence CACCTCCATGTTCTTCCGG-TACCCCCCAGA.GGTAAG (SEQ ID NO: 68) as the forward primer and delD4-rev with the reverse complement sequence as the reverse primer. A protocol variation published in BioTechniques 26 (1999) 680 was used to extend both primers in separate reactions in three cycles preceeding the regular Stratagene protocol:

Two separate 50 µl reaction mixtures were set up according to the manufacturer's manual, each containing 10 ng plasmid pCMV-preS-Fc-hCSF1R-ECD as the template and 10 pM of one of the primers delD4-for or delD4-rev, and 0.5 µl Pfu DNA polymerase as provided with the kit. Three PCR cycles 95° C. 30 sec/55° C. 60 sec/68° C. 8 min were run, then 25 µl each of both reaction mixtures were combined in a new tube and 0.5 µl fresh Pfu DNA polymerase were added. The regular PCR protocol with 18 temperature cycles as specified by Stratagene in the kit manual was carried out, followed by 2 hrs final digestion with the Dpn1 restriction enzyme provided with the kit. Clones bearing the deletion were detected by digestion with Cel II and Not I and verified by sequencing.

Protein was prepared by transient transfection in the Hek293 FreeStyle suspension cell system (Invitrogen) according to the manufacturer's specifications. After 1 week 500 ml supernatant was filtered and loaded onto a 1 ml HiTrap MabSelect Xtra (GE healthcare) protein A column (0.2 ml/min). The colomn was washed first with PBS, then with 50 mM Tris/150 mM NaCl/1 mM EDTA/pH 7.3. 75 µl PreScission Protease (GE #27-0843-01) diluted in 375 µl of the same buffer were loaded onto the column and the closed column was incubated over night at 4° C. with rolling. The column was mounted on top of a 1 ml GSTrap FF column (GE helthcare) and the desired protein was eluted (0.2 ml/min, 0.2 ml fractions). Pooled fractions were concentrated from 1.8 ml to 0.4 ml by centrifugal ultrafiltration via a 3 k Nanosep and chromatographed over an S200 HR SEC in PBS (0.5 ml/min).

Human CSF-1R fragment delD4 was obtained in two fractions as a dimeric molecule (pool1, V=1.5 ml; c=0.30 mg/ml; apparent mass on SDS page 83 kDa, reduced 62 kDa) and as the monomer (pool 2, V=1.4 ml; c=0.25 mg/ml apparent mass on SDS page 62 kDa). The dimeric form was used for all experiments.

Determination of the Binding of Anti-CSF-1R Antibodies to Human CSF-1R Fragment delD4 and to Human CSF-1R Extracellular Domain (CSF-1R-ECD) (Binding Signals as Response Units (RU):

Instrument: Biacore T100 (GE Healthcare)

Software: T100 Control, Version 2.0.1

T100 Evaluation, Version 2.0.2

Assayformat Chip: CM5

Temperature: 25° C.

CSF-1R fragments were immobilized via amine coupling. To compare the binding of different anti-CSF-1R antibodies according to the invention one concentration of the test antibody was injected. Anti CSF-1R Mah3291 (R&D-Systems) and SC 2-4A5 (Santa Cruz Biotechnology, US—see also Sherr, C. J. et al., Blood 73 (1989) 1786-1793), was used as reference control, anti-CCR5 m<CCR5>Pz03.1C5 (deposited as DSM ACC 2683 on 18 Aug. 2004 at DSMZ) as negative control, all under the same conditions as the anti-CSF-1R antibodies according to the invention.

Amine Coupling of CSF-1R Fragments

Standard amine coupling according to the manufacturer's instructions: running buffer: PBS-T (Roche: 11 666 789+ 0.05% Tween20: 11 332 465), activation by mixture of EDC/NHS, injection of human CSF-1R fragment delD4 (comprising the extracellular subdomains D1-D3 and D5) (SEQ ID NO: 65) and human CSF-1R Extracellular Domain (CSF-1R-ECD) (comprising the extracellular subdomains D1-D5) (SEQ ID NO: 64) for 600 seconds at flow rate 10 µl/min; diluted in coupling buffer NaAc, pH 5.0, c=10 µg/mL; finally remaining activated carboxyl groups were blocked by injection of 1 M Ethanolamin.

Binding of <CSF-1R>Mab 2F11, Mab 2E10, Mab 3291 and sc2-4A5 and Other Anti-CW4R Antibodies to Human CSF-1R Fragment delD4 and Human CSF-1R Extracellular Domain (CSF-1R-ECD) at 25° C.

Running buffer: PBS-T (Roche: 11 666 789+0.05% Tween20: 11 332 465)

Analyte Sample:

Binding was measured at a flow rate of 30 µL/min by one injection of the analyte with concentration c=10 nM. (for Mab 1G10, Mab 2H7 and humanized hMab 2F11-e7 in second experiment) Each injection was 700 seconds long, followed by a dissociation phase of 180 seconds. Final regeneration was performed after each cycle using 50 mM NaOH, contact time 60 seconds, flow rate 30 µL/min.

Signals were measured by a report point 10 seconds after end of injection. Reference signals (signals from a blank reference flow cell (treated with EDC/NHS and ethanolamine, only) were subtracted to give the binding signals (as RU). If binding signals of nonbinding antibodies were slightly below 0 (Mab 2F11=−3; Mab 2E10=−2; Mab 1G10=−6, Mab 2H7=−9; and humanized hMab 2F11-e7=−7) the values were set as 0.

TABLE 3a

Binding of <CSF-1R> MAbs to human CSF-1R fragment delD4 and CSF-1R-ECD and ratio at 25° C., measured by SPR

|  | Binding to delD4 [RU] | Binding to CSF-1R-ECD [RU] | Ratio of binding of anti-CSF1R antibodies to CSF1R fragment delD4/to CSF-1R-ECD |
|---|---|---|---|
| Mab 3291 | 1015 | 627 | 1015/627 = 1.61 |
| sc2-4A5 | 374 | 249 | 374/249 = 1.50 |
| Mab 2F11 | 0 | 176 | 0/176 = 0 |
| hMab 2F11-e7 | 0 | 237 | 0/237 = 0 |
| Mab 2E10 | 0 | 120 | 0/120 = 0 |
| Mab 1G10 | 0 | 2708 | 0/2708 = 0 |
| Mab 2H7 | 0 | 147 | 0/147 = 0 |
| m<CCR5>Pz03.1C5 | 2 | 5 | — |

Mab 2F11 and Mab 2E10 showed binding to the human CSF-1R Extracellular Domain (CSF-1R-ECD) (see FIG. 2b); however no binding was detected to CSF-1R fragment delD4. (see FIG. 2a).

Figure 2A:
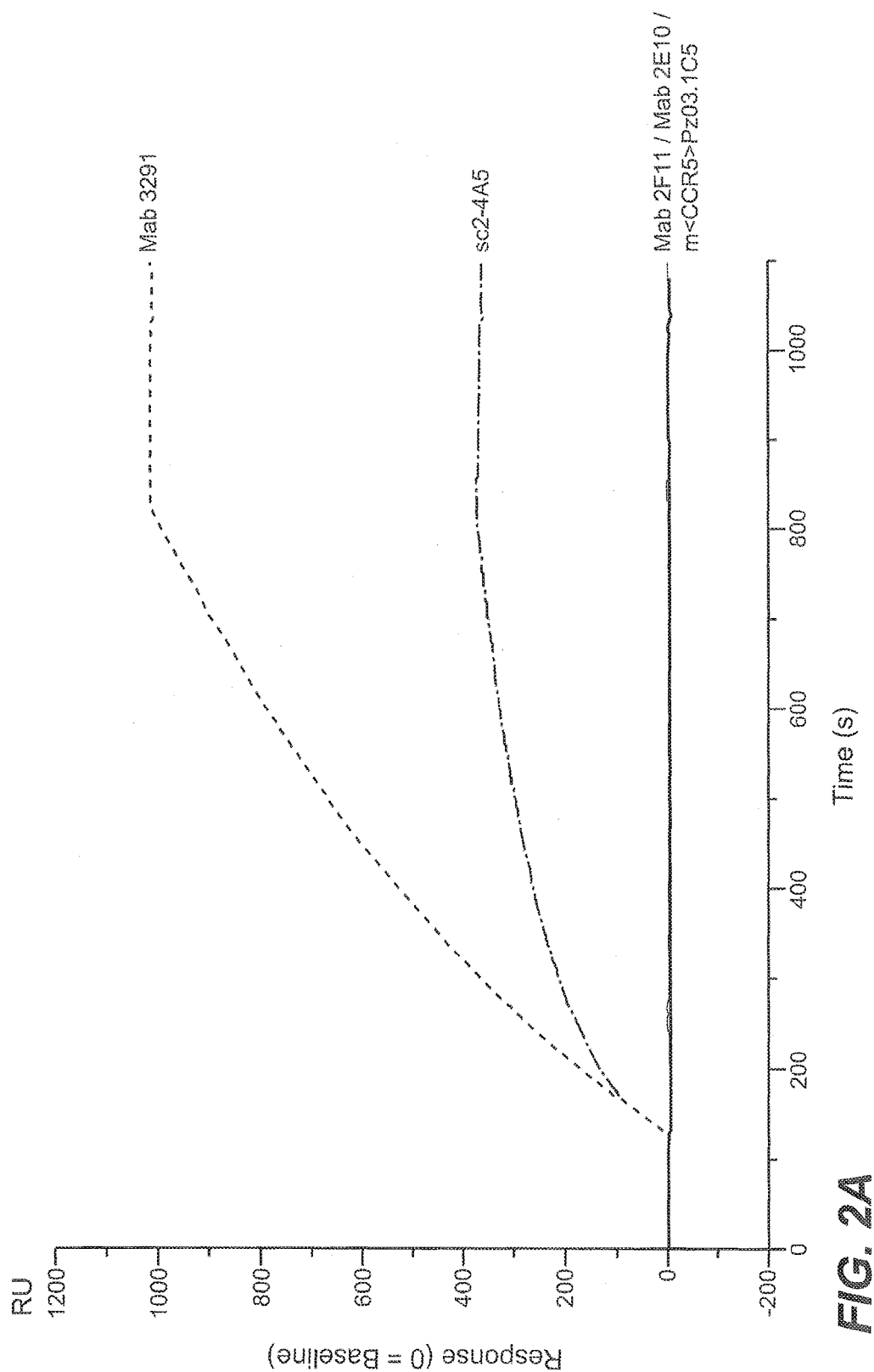
FIG. 2A Biacore sensogram of binding of different anti-CSF-1R antibodies to immobilized human CSF-1R fragment delD4 (comprising the extracellular subdomains D1-D3 and D5) (SEQ ID NO: 65) (y-axis: binding signal in Response Units (RU), baseline=0 RU, x-axis: time in seconds(s)): While the antibodies Mab 3291 and sc 2-4A5 clearly show binding to this delD4 fragment, the antibodies according to the invention e.g. Mab 2F11, and Mab 2E10, did not bind to the CSF-1R fragment delD4. The control anti-CCR5 antibody m<CCR5>Pz03.1C5 did also not bind to the CSF-1R fragment delD4.
Figure 2B:
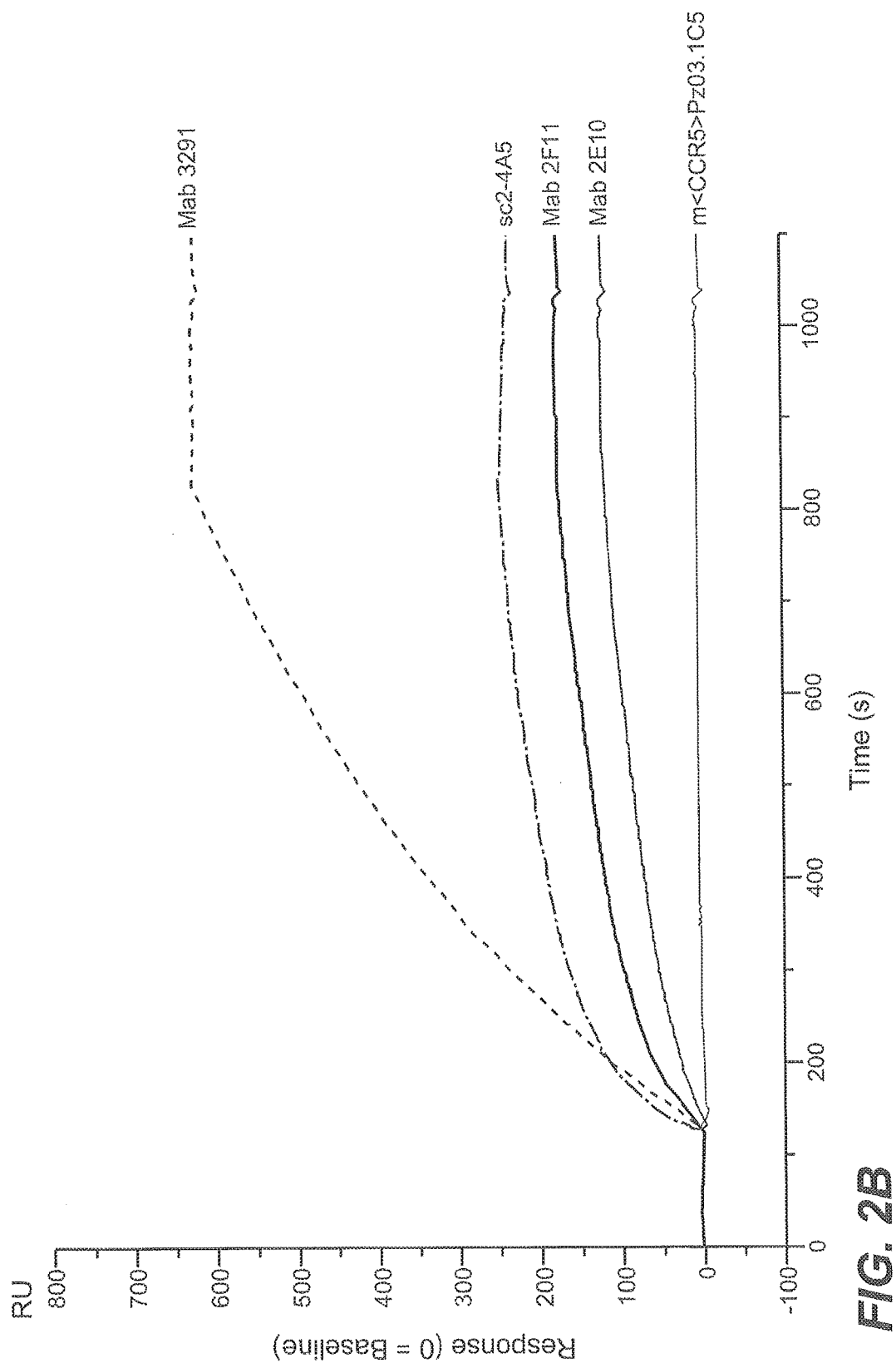
FIG. 2B Biacore sensogram of binding of different anti-CSF-1R antibodies to immobilized human CSF-1R Extracellular Domain (CSF-1R-ECD) (comprising the extracellular subdomains D1-D5) (SEQ ID NO: 64) (y-axis: binding signal in Response Units (RU), baseline=0 RU, x-axis: time in seconds(s))::  All anti-CSF-1R antibodies show binding to CSF-1R-ECD. The control anti-CCR5 antibody m<CCR5>Pz03.1C5 did not bind, to the CSF-1R-ECD.

Sc2-4A5 and MAB3291 showed binding to CSF-1R-ECD and to del D4 (see FIGS. 2b and 2a).

Thus the ratio of binding of anti-CSF-1R antibodies Mab 2F11 and Mab 2E10 to CSF1R fragment delD4/to CSF-1R-ECD was clearly below 1:50 (=0.02), while the binding ratio of MAB3291 and Sc2-4A5 were 1.61 and 1.50, respectively and were highly above 1:50 (=0.02). Negative control antibody m<CCR5>Pz03.1C5 did not show any binding (as expected).

Figure 2C:
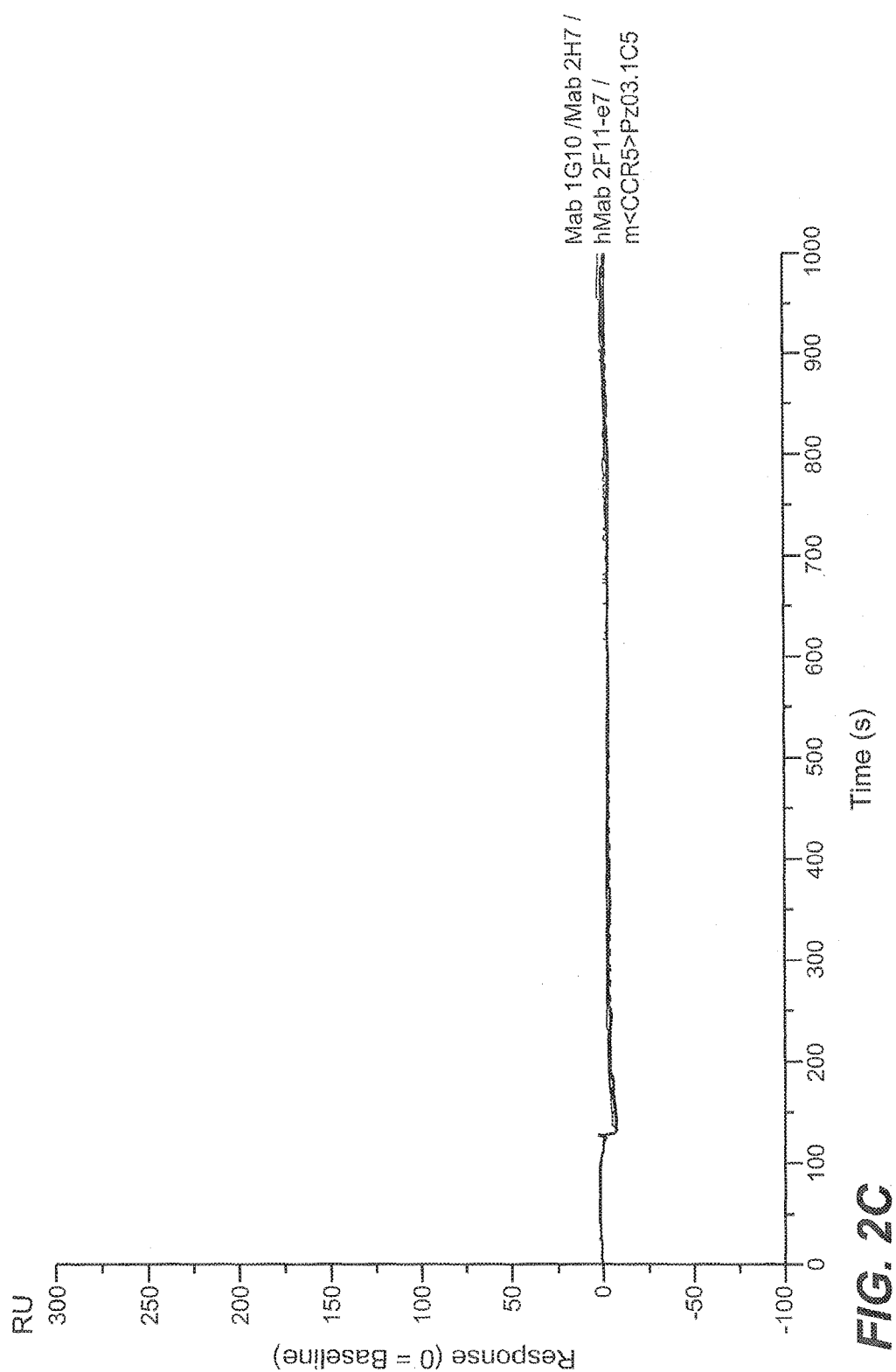
FIG. 2C Biacore sensogram of binding of different anti-CSF-1R antibodies to immobilized human CSF-1R fragment delD4 (comprising the extracellular subdomains D1-D3 and D5) (SEQ ID NO: 65) (y-axis: binding signal in Response Units (RU), baseline=0 RU, x-axis: time in seconds (s)): Mab 1G10, Mab 2H7 and humanized hMab 2F11-e7 did not bind to the CSF-1R fragment delD4. The control anti-CCR5 antibody m<CCR5>Pz03.1C5 did also not bind to the CSF-1R fragment delD4.
Figure 2D:
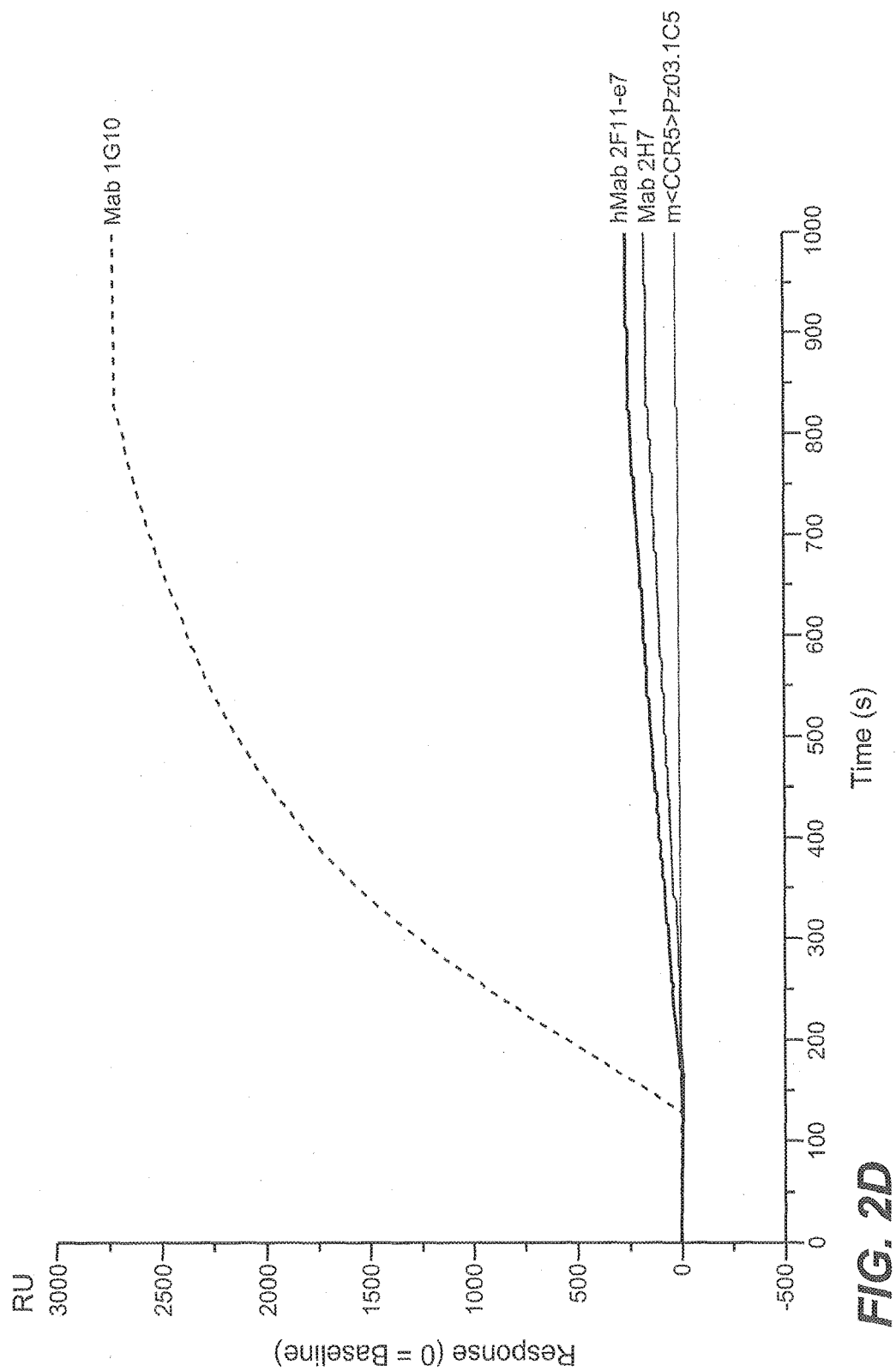
FIG. 2D Biacore sensogram of binding of different anti-CSF-1R antibodies to immobilized human CSF-1R Extracellular Domain (CSF-1R-ECD) (comprising the extracellular subdomains D1-D5) (SEQ ID NO: 64) (y-axis: binding signal in Response Units (RU), baseline=0 RU, x-axis: time in seconds (s)): All anti-CSF-1R antibodies Mab 1G10, Mab 2H17 and humanized hMab 2F11-e7 showed binding to CSF-1R-ECD. The control anti-CCR5 antibody m<CCR5>Pz03.1C5 did not bind to the CSF-1R-ECD.

Mab 1G10, Mab 2H7 and humanized hMab 2F11-e7 showed binding to the human CSF-1R Extracellular Domain (CSF-1R-ECD) (see FIG. 2d); however no binding was detected to CSF-1R fragment delD4, (see FIG. 2c). Thus the ratio of binding of anti-CSF1R antibodies Mab 1G10, Mab 2H7 and humanized hMab 2F11-e7 to CSF1R fragment delD4/to CSF-1R-ECD was clearly below 1:50 (=0.02).

In a further experiment anti-CSF-1R antibodies 1.2.SM (ligand displacing CSF-1R antibody described in WO2009026303), CXHG6 (ligand displacing CSF-1R antibody described in WO 2009/112245), the goat polyclonal anti-CSF-1R antibody ab10676 (abeam) were investigated. Anti-CSF-1R antibody Mab3291 (R&D-Systems) was used as reference control. Anti-CCR5 m<CCR5>Pz03.1C5 (deposited as DSM ACC 2683 on 18 Aug. 2004 at DSMZ) was used as negative control.

TABLE 3b

Binding of <CSF-1R> MAbs to human CSF-1R fragment delD4 and CSF-1R-ECD and ratio at 25° C., measured by SPR

|  | Binding to delD4 [RU] | Binding to CSF-1R-ECD [RU] | Ratio of binding of anti-CSF1R antibodies to CSF1R fragment delD4/to CSF-1R-ECD |
|---|---|---|---|
| MAB3291 | 1790 | 1222 | 1790/1222 = 1.47 |
| 1.2.SM | 469 | 704 | 469/704 = 0.67 |
| CXIIG6 | 1983 | 1356 | 1983/1356 = 1.46 |
| ab10676 | 787 | 547 | 787/547 = 1.44 |
| m<CCR5>Pz03.1C5 | 0 | 0 | — |

Figure 2E:
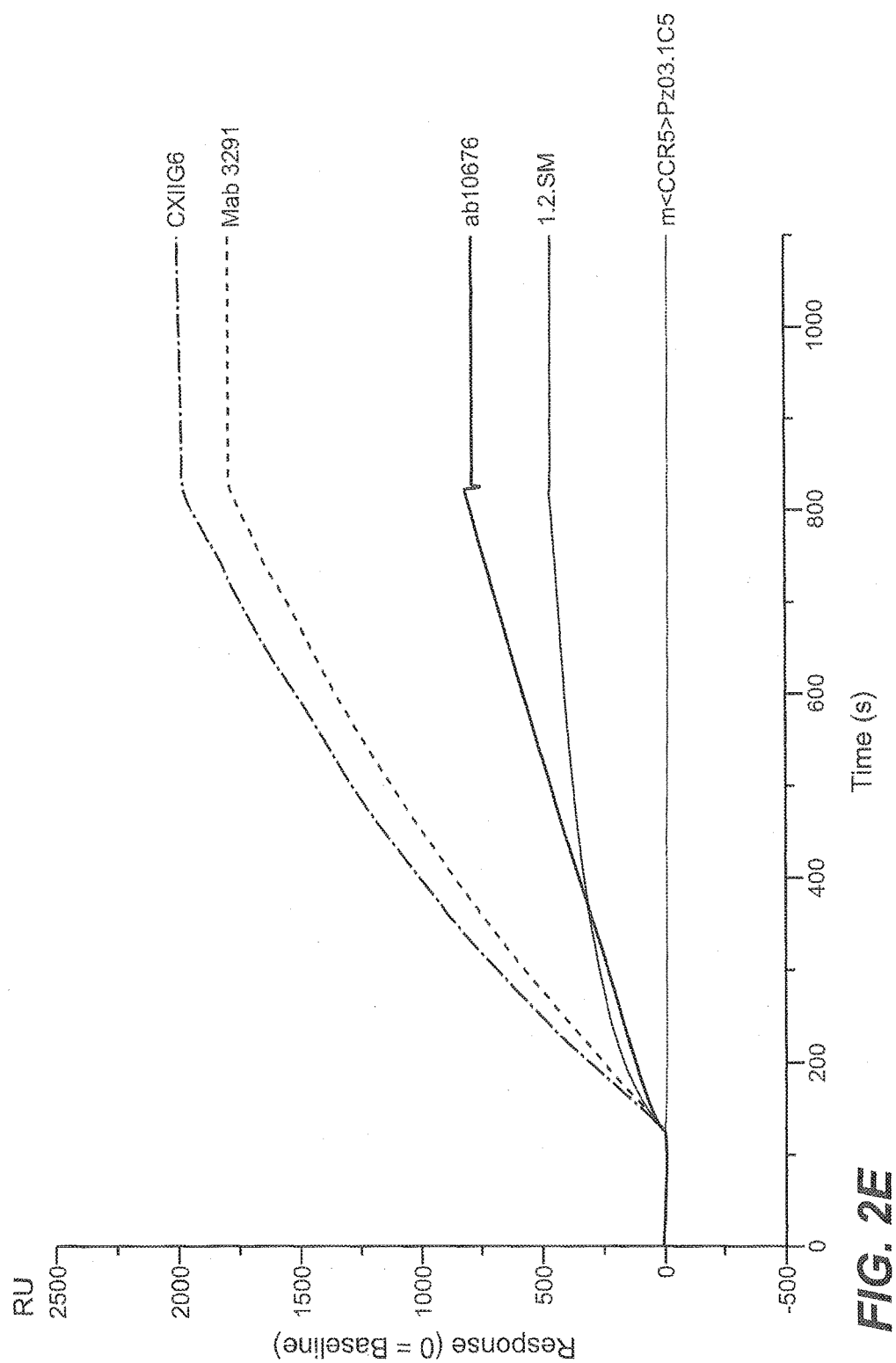
FIG. 2E Biacore sensogram of binding of different anti-CSF-1R antibodies to immobilized human CSF-1R fragment delD4 (comprising the extracellular subdomains D1-D3 and D5) (SEQ ID NO: 65) (y-axis: binding signal in Response Units (RU), baseline=0 RU, x-axis: time in seconds(s)): All anti-CSF-1R antibodies 1.2.SM, CXIIG6, ab10676 and MAB3291 show binding to to the CSF-1R fragment delD4. The control anti-CCR5 antibody m<CCR5>Pz03.1C5 did also not bind to the CSF-1R fragment delD4.
Figure 2F:
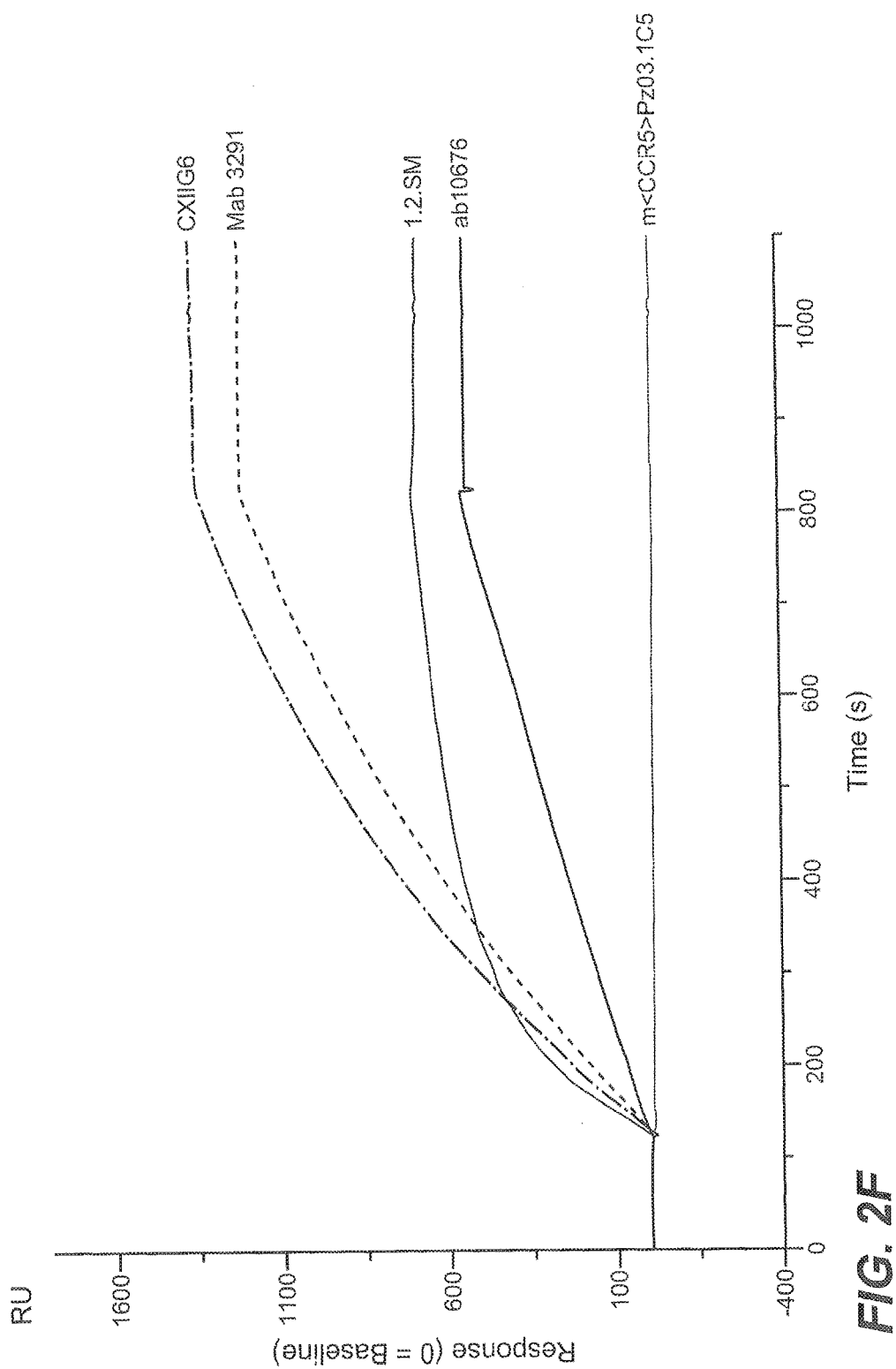
FIG. 2F Biacore sensogram of binding of different anti-CSF-1R antibodies to immobilized human CSF-1R Extracellular Domain (CSF-1R-ECD) (comprising the extracellular subdomains D1-D5) (SEQ ID NO: 64) (y-axis: binding signal in Response Units (RU), baseline=0 RU, x-axis: time in seconds(s))::  All anti-CSF-1R antibodies 1.2.SM, CXIIG6, ab10676 and MAB3291 show binding to CSF-1R-ECD. The control anti-CCR5 antibody m<CCR5>Pz03.1C5 did not bind to the CSF-1R-ECD.
Figure 3A:
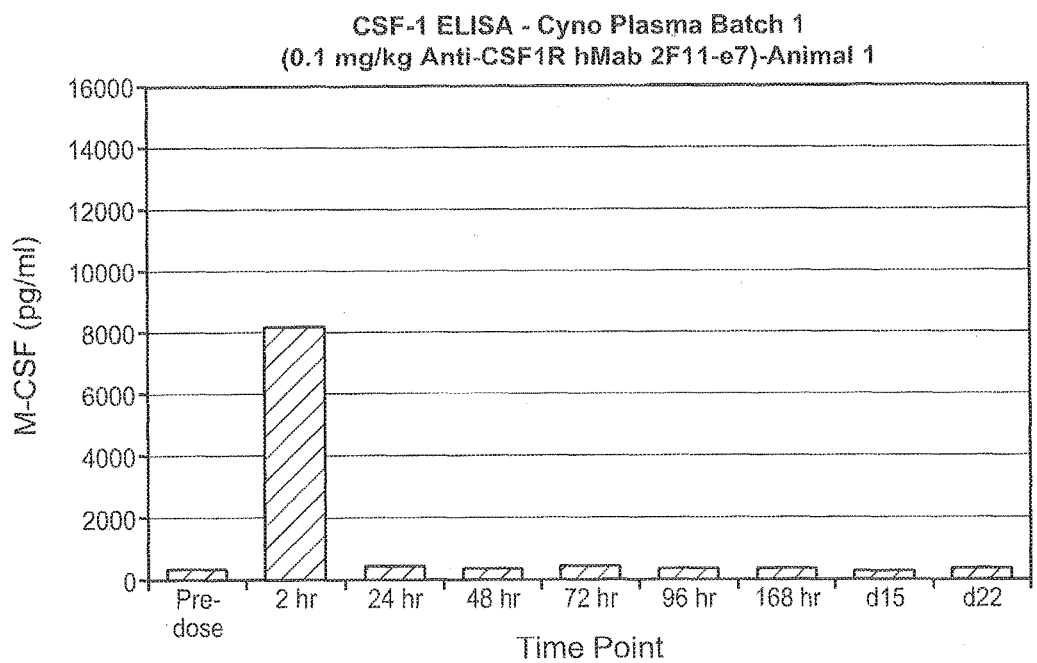
FIG. 3A-3D CSF-1 levels in Cynomolgus monkey after application of different dosages of anti-CSF-1R antibody according to the invention FIG. 4 In vivo efficacy—tumor growth inhibition of anti-CSF-1R antibodies according to the invention in breast cancer BT20 xenograft
Figure 3B:
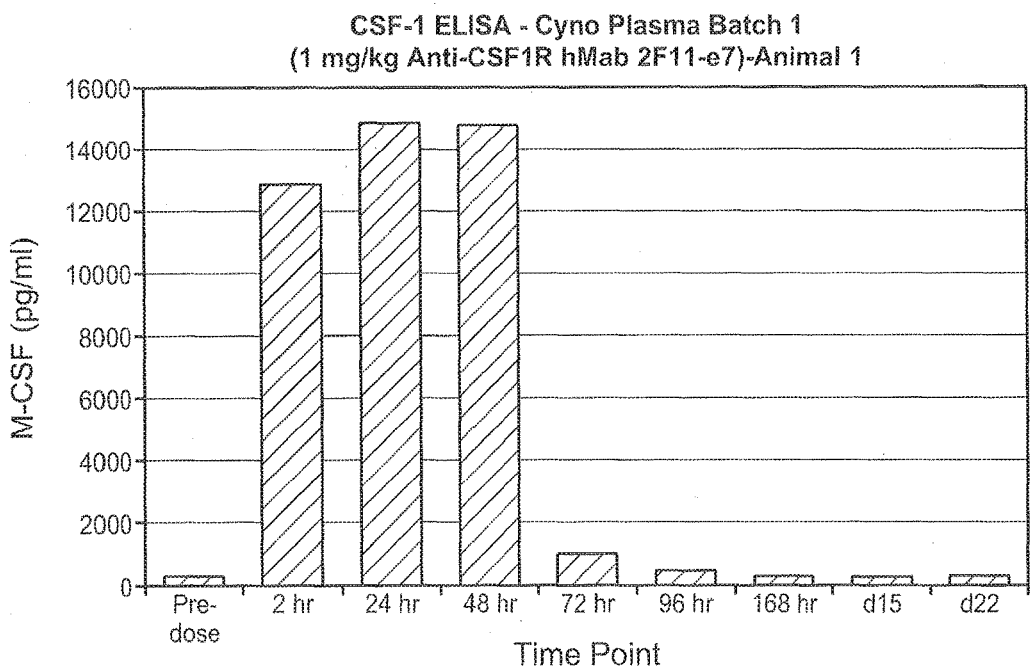
Figure 3C:
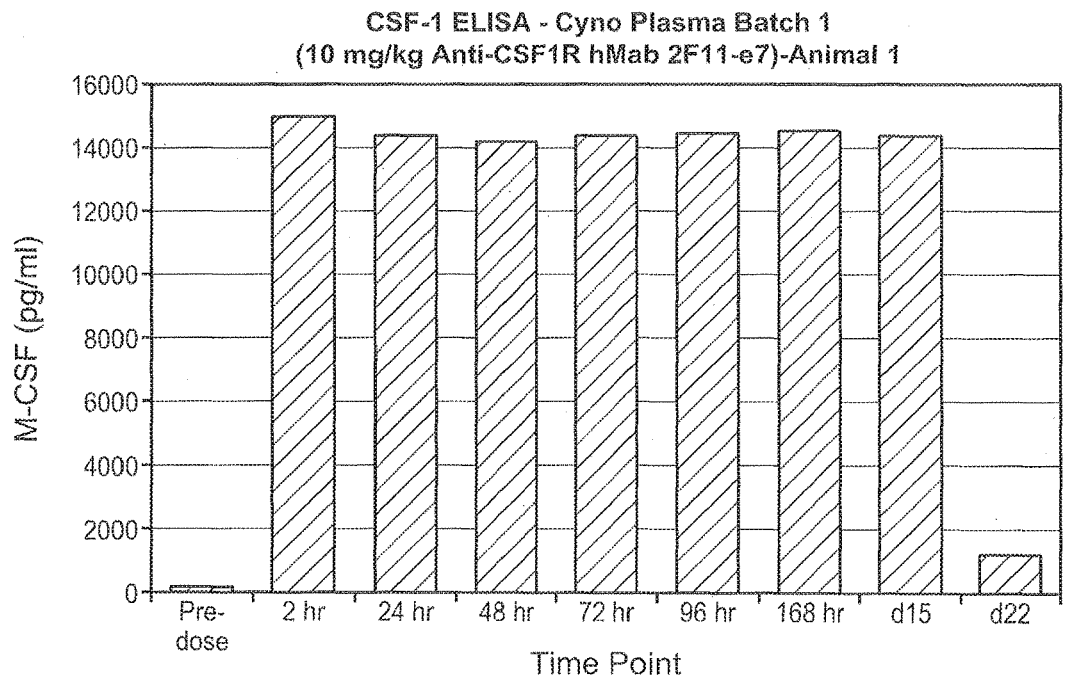
Figure 3D:
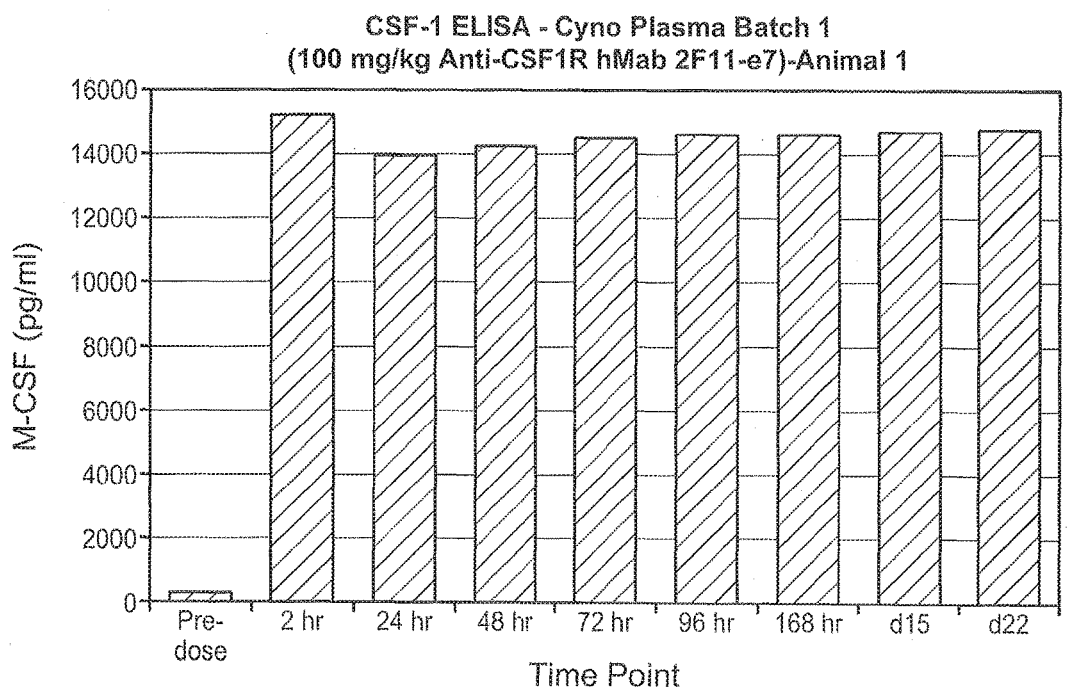

1.2.SM, CXIIG6, ab10676 and MAB3291 showed binding to CSF-1R-ECD and to del D4 (see FIGS. 2f and 2e).

The binding ratio of 1.2.SM, CXHG6, ab10676 and MAB3291 was highly above 1:50 (=0.02). Negative control antibody m<CCR5>Pz03.1C5 did not show any binding (as expected).

Example 5

Growth Inhibition of NIH3T3-CSF-1R Recombinant Cells in 3D Culture Under Treatment with Anti-CSF-1R Monoclonal Antibodies (CellTiterGlo-assay)

NIH3T3 cells, retrovirally infected with either an expression vector for full-length wildtype CSF-1R (SEQ ID NO: 62) or mutant CSF-1R L301S Y969F (SEQ ID NO: 63), were cultured in DMEM high glucose media (PAA, Pasching, Austria) supplemented with 2 mM L-glutamine, 2 mM sodium pyruvate and non-essential amino acids and 10% fetal bovine serum (Sigma, Taufkirchen, Germany) on poly-HEMA (poly(2-hydroxyethylmethacrylate)) (Polysciences, Warrington, Pa., USA)) coated dishes to prevent adherence to the plastic surface. Cells are seeded in medium replacing serum with 5 ng/ml sodium selenite, 10 mg/ml transferrin, 400 µg/ml BSA and 0.05 mM 2-mercaptoethanol. When treated with 100 ng/ml huCSF-1 (Biomol, Hamburg, Germany) wtCSF-1R (expressing cells form dense spheroids that grow three dimensionally, a property that is called anchorage independence. These spheroids resemble closely the three dimensional architecture and organization of solid tumors in situ. Mutant CSF-1R recombinant cells are able to form spheroids independent of the CSF-1 ligand. Spheroid cultures were incubated for 3 days in the presence of different concentrations of antibody in order to determine an IC50 (concentration with 50 percent inhibition of cell viability). The CellTiterGlo assay was used to detect cell viability by measuring the ATP-content of the cells.

TABLE 5a

| CSF-1R Mab | wtCSF-1R $IC_{50}$ [µg/ml] | Mutant CSF-1R $IC_{50}$ [µg/ml] |
| --- | --- | --- |
| Mab 2F11 | 1.1 | 8.0 |
| Mab 2E10 | 0.49 | 4.9 |
| Mab 2H7 | 0.31 | 5.3 |
| Mab 1G10 | 0.29 | 14.2 |
| SC 2-4A5 | 10.0 | 10.0 |

Reference control Mab R&D-Systems 3291 did not show inhibition of mutant CSF-1R recombinant cell proliferation.

In a further experiment the anti-CSF-1R antibody according to the invention hMab 2F11-e7 and the anti-CSF-1R antibodies 1.2.SM (ligand displacing CSF-1R antibody described in WO2009026303), CXIIG6 (ligand displacing CSF-1R antibody described in WO 2009/112245), the goat polyclonal anti-CSF-1R antibody ab10676 (abcam), and SC 2-4A5 (Santa Cruz Biotechnology, US—see also Sherr, C. J. et al., Blood 73 (1989) 1786-1793) were investigated.

Spheroid cultures were incubated for 3 days in the presence of different concentrations of antibody in order to determine an IC30 (concentration with 30 percent inhibition of cell viability). Maximum concentration was 20 µg/ml The CellTiterGlo assay was used to detect cell viability by measuring the ATP-content of the cells.

TABLE 5b

| CSF-1R Mab | wtCSF-1R $IC_{30}$ [µg/ml] | Mutant CSF-1R $IC_{30}$ [µg/ml] |
| --- | --- | --- |
| hMab 2F11-e7 | 4.91 | 0.54 |
| 1.2.SM | 1.19 | >20 µg/ml (−19% inhibition at 20 µg/ml = 19% stimulation) |
| CXIIG6 | >20 µg/ml (21% inhibition at 20 µg/ml) | >20 µg/ml (−36% inhibition at 20 µg/ml = 36% stimulation) |
| ab10676 | 14.15 | >20 µg/ml (0% inhibition at 20 µg/ml) |
| SC 2-4A5 | 16.62 | 2.56 |

Example 6

Growth Inhibition of BeWo Tumor Cells in 3D Culture Under Treatment with Anti-CSF-1R Monoclonal Antibodies (CellTiterGlo-assay)

BeWo choriocarcinoma cells (ATCC CCL-98) were cultured in F12K media (Sigma, Steinheim, Germany) supplemented with 10% FBS (Sigma) and 2 mM L-glutamine. $5 \times 10^4$ cells/well were seeded in 96-well poly-HEMA (poly (2-hydroxyethylmethacrylate)) coated plates containing F12K medium supplemented with 0.5% FBS and 5% BSA. Concomitantly, 200 ng/ml huCSF-1 and 10 µg/ml of different anti-CSF-1R monoclonal antibodies were added and incubated for 6 days. The CellTiterGlo assay was used to detect cell viability by measuring the ATP-content of the cells in relative light units (RLU). When BeWo spheroid cultures were treated with different anti-CSF-1R antibodies (10 µg/ml) inhibition of CSF-1 induced growth was observed. To calculate antibody-mediated inhibition the mean RLU value of unstimulated BeWo cells was subtracted from all samples. Mean RLU value of CSF-1 stimulated cells was set arbitrarily to 100%. Mean RLU values of cells stimulated with CSF-1 and treated with anti-CSF-1R antibodies were calculated in % of CSF-1 stimulated RLUs. The Table 6 shows the calculated data of growth inhibition of BeWo tumor cells in 3D culture under treatment with anti-CSF-1R monoclonal antibodies; FIGS. 1a and b depicts normalized mean RLU values.

TABLE 6

| CSF-1R Mab | % inhibition 10 µg/ml antibody concentration |
| --- | --- |
| CSF-1 only | 0 |
| Mab 2F11 | 70 |
| Mab 2E10 | 102 |
| Mab 2H7 | 103 |
| Mab 1G10 | 99 |
| SC 2-4A5 | 39 |

Example 7

Inhibition of Human Macrophage Differentiation Under Treatment with Anti-CSF-1R Monoclonal Antibodies (CellTiterGlo-assay)

Human monocytes were isolated from peripheral blood using the RosetteSep™ Human Monocyte Enrichment Cocktail (StemCell Tech.—Cat. No.15028). Enriched monocyte populations were seeded into 96 well microtiterplates ($2.5 \times 10^4$ cells/well) in 100 µl RPMI 1640 (Gibco—Cat. No. 31870) supplemented with 10% FCS (GIBCO—Cat. No. 011-090014M), 4 mM L-glutamine (GIBCO—Cat. No. 25030) and 1× PenStrep (Roche Cat. No. 1 074 440) at 37° C. and 5% $CO_2$ in a humidified atmosphere. When 150 ng/ml huCSF-1 was added to the medium, a clear differentiation into adherent macrophages could be observed. This differentiation could he inhibited by addition of anti-CSF-1R antibodies. Furthermore, the monocyte survival is affected and could be analyzed by CellTiterGlo (CTG) analysis. From the concentration dependent inhibition of the survival of monocytes by antibody treatment, an $IC_{50}$ was calculated (see Table 7).

TABLE 7

| CSF-1R Mab | $IC_{50}$ [µg/ml] |
|---|---|
| Mab 2F11 | 0.08 |
| Mab 2E10 | 0.06 |
| Mab 2H7 | 0.03 |
| Mab 1G10 | 0.06 |
| SC 2-4A5 | 0.36 |

In a seperate test series humanized versions of Mab 2 F11, e.g. hMab 2F11-c11, hMab 2F11-d8, hMab 2F11-e7, hMab 2F11-f12, showed IC50 values of 0.07 µg/ml (hMab 2F11-c11), 0.07 µg/ml (hMab 2F11-d8), 0.04 µg/ml (hMab 2F11-e7) and 0.09 µg/ml (hMab 2F11-f12).

Example 8

Inhibition of Cynomolgous Macrophage Differentiation Under Treatment with Anti-CSF-1R Monoclonal Antibodies (CellTiterGlo-assay)

Cynomolgous monocytes were isolated from peripheral blood using the CD14 MicroBeads non-human primate kit (Miltenyi Biotec—Cat.No. 130-091-097) according to the manufacturers description. Enriched monocyte populations were seeded into 96 well microtiterplates ($1-3 \times 10^4$ cells/well) in 100 µl RPMI 1640 (Gibco—Cat. No. 31870) supplemented with 10% FCS (GIBCO—Cat. No. 011-090014M), 4 mM L-glutamine (GIBCO—Cat. No. 25030) and 1× PenStrep (Roche Cat. No. 1 074 440) at 37° C. and 5% $CO_2$ in a humidified atmosphere. When 150 ng/ml huCSF-1 was added to the medium, a clear differentiation into adherent macrophages could be observed. This differentiation could be inhibited by addition of anti-CSF-1R antibodies. Furthermore, the monocyte survival, is affected and could be analyzed by CellTiterGlo (CTG) analysis. The viability was analyzed at a concentration of 5 µg/ml antibody treatment (see Table 8).

TABLE 8

| CSF-1R Mab | % survival | % inhibition (of survival) = (100% − % survival) |
|---|---|---|
| Mab 2F11 | 4* | 96 |
| Mab 2E10 | 17** | 83 |
| Mab 2H7 | 8 | 92 |
| Mab 1G10 | 2 | 98 |
| SC 2-4A5 | 31 | 69 |

*mean of four experiments (3 expts. using the murine, 1 expt. using the chimeric mAb)
**mean of two experiments using the murine mAb only Example 9

Determination of the Binding Affinity of Anti-CSF-1R Antibodies to Human CSF-1R

Instrument: BIACORE® A100
Chip: CMS (Biacore BR-1006-68)
Coupling: amine coupling
Buffer: PBS (Biacore BR-1006-72), pH 7.4, 35° C.

For affinity measurements 36 µg/ml anti mouse Fcγ antibodies (from goat, Jackson Immuno Reasearch JIR115-005-071) have been coupled to the chip surface for capturing the antibodies against CSF-1R. Human CSF-1R Extracellular Domain (CSF-1R-ECD) (comprising the extracellular subdomains D1-D5) (SEQ ID NO: 64) (R&D-Systems 329-MR or subcloned pCMV-presS-HisAvitag-hCSF-1R-ECD) was added in various concentrations in solution. Association was measured by an CSF-1R-injection of 1.5 minutes at 35° C.; dissociation was measured by washing the chip surface with buffer for 10 minutes at 35° C. For calculation of kinetic parameters the Langmuir 1:1 model was used.

TABLE 9

| Affinity data measured by SPR | | | | |
|---|---|---|---|---|
| CSF-1R Mab | $K_D$ (nM) | $k_a$ (1/Ms) | $k_d$ (1/s) | $t_{1/2}$ (min) |
| Mab 2F11 | 0.29 | $1.77E^{+05}$ | $5.18E^{-05}$ | 223 |
| Mab 2E10 | 0.2 | $1.52E^{+05}$ | $2.97E^{-05}$ | 389 |
| Mab 2H7 | 0.21 | $1.47E^{+05}$ | $3.12E^{-05}$ | 370 |
| Mab 1G10 | 0.36 | $1.75E^{+05}$ | $6.28E^{-05}$ | 184 |

In a separate biacore binding assay using the CSF-1R ECD (data not shown) some competition of the antibodies Mab 2E11 and Mab 2E10 with the antibody Ab SC-2-4A5 was shown. However Mab 2F11/Mab 2E10 do not bind to the human CSF-1R fragment delD4, whereas Ab SC-2-4A5 binds to this delD4 fragment (see Example 4 and FIG. 2a). Thus the binding region of Mab 2F11/Mab 2E10 is clearly distinct from the binding region of Ab SC-2-4A5, but probably located in a vicinity area. In such competition assay both antibodies Mab 2F11 and Mab 2E10 did not compete with Mab3291 from R&D-Systems (data not shown).

Example 10

Determination of the Binding of Anti-CSF-1R Antibodies to Human CSF-1R Fragment D1-D3

Instrument; Biacore T100 (GE Healthcare)
Software: T100 Control, Version 1.1.11.
  B3000 Evaluation, Version 4.01
  Scrubber, Version 2.0a
Assayformat Chip:CM5-Chip Antibodies against CSF-1R were captured via amine coupled capture molecules. Using the single cycle kinetics five increasing concentrations of human CSF-1R fragment D1-D3 (SEQ ID NO: 66) were injected. Human CSF-1R fragment D1-D3 was subcloned into pCMV-presS-HisAvitag expression vector, Anti CSF-1R SC 2-4A5 (Santa Cruz Biotechnology, US; Sherr, C. J., et al., Blood 73 (1989) 1786-1793) which inhibits the ligand-receptor interaction, and Mab 3291 (R&D-Systems) were used as reference controls.

Capture molecules: Anti mouse Fcγ antibodies (from goat, Jackson Immuno Reasearch JIR115-005-071) for antibodies according to the invention and the R&D-Systems control Mab 3291 and Anti rat Fcγ antibodies (from goat, Jackson Immuno Reasearch JIR112-005-071) for the reference control anti CSF-1R SC 2-4A5.

Amine Coupling of Capture Molecules

Standard amine coupling according to the manufacturer's instructions: running buffer: HBS-N buffer, activation by mixture of EDC/NHS, aim for ligand density of 2000 RU;

the capture-Abs were diluted in coupling buffer NaAc, pH 4.5, c=10 μg/mL; finally remaining activated carboxyl groups were blocked by injection of 1 M Ethanolamin.

Kinetic Characterization of Human CSF-1R Fragments D1-D3 Binding to MAbs <CSF-1R> at 37° C.

Running buffer: PBS (Biacore BR-1006-72)

Capturing of Mabs <CSF-1R> on flow cells 2 to 4: Flow 20 μL/min, contact time 90 seconds, c(Abs<CSF-1R>)=50 nM, diluted with running buffer+1 mg/mL BSA;

Analyte sample:

Single Cycle Kinetics was measured at a flow rate of 30 μL/min by five consecutive injections of the analyte with concentrations, c =7.8, 31.25, 125 500 and 2000 nM, without regeneration. Each injection was 30 seconds long and followed by a dissociation phase of 120 Seconds for the first four injections, and finally 1200 seconds for the highest concentration (=last injection).

Final regeneration was performed after each cycle using 10 mM Glycin pH 1.5 (Biacore BR-1003-54), contact time 60 seconds, flow rate 30 μL/min.

Kinetic parameters were calculated by using the usual double referencing (control reference: binding of analyte to capture molecule; Flow Cell: subdomain CSF-1R concentration "0" as Blank) and calculation with model 'titration kinetics 1:1 binding with draft'.

TABLE 10

Affinity data for binding of human CSF-1R fragment D1-D3 measured by SPR

| CSF-1R Mab | Sub domain | $K_D$ (nM) | $k_a$ (1/Ms) | $k_d$ (1/s) | $t_{1/2}$ (min) |
|---|---|---|---|---|---|
| Mab 2F11 | D1-D3 | no binding | | | |
| Mab 2E10 | D1-D3 | no binding | | | |
| Mab 2H7 | D1-D3 | not determined | | | |
| Mab 1G10 | D1-D3 | no binding | | | |
| SC-2-4A5 | D1-D3 | no binding | | | |
| R&D-Systems 3291 | D1-D3 | 5.4 | $2.2E^{+5}$ | $1.2E^{-3}$ | 9.6 |

The antibodies Mab 2F11, Mab 2E10 and Mab 1G10 showed no binding to human CSF-1R fragment D1-D3

Also reference control-Ab SC-2-4A5 did not bind to human CSF-1R fragment D1-D3.

The reference control Mab R&D-Systems 3291 showed binding to the human CSF-1R fragment D1-D3.

Example 11

CSF-1 Level Increase During CSF-1R Inhibition in Cynomolgus Monkey

Serum CSF-1 levels provide a pharmacodynamic marker of CSF-1R neutralizing activity of anti-human CSF-1R dimerization inhibitor hMab 2F11-e7. One male and one female cynomolgus monkey per dosage group (1 and 10 mg/kg) were intravenously administered anti-CSF1R antibody hMab 2F11e7. Blood samples for analysis of CSF-1 levels were collected 1 week before treatment (pre-dose), 2, 24, 48, 72, 96, 168 hours post-dose and weekly for two additional weeks. CSF-1 levels were determined using a commercially available ELISA kit (Quantikine® human M-CSF) according to the manufacturer's instructions (R&D Systems, UK). Monkey CSF-1 level were determined by comparison with CSF-1 standard curve samples provided in the kit.

Administration of hMab 2F11-e7 induced a dramatic increase in CSF-1 by ~1000-fold, which depending on the dose administered lasted for 48 hr (1 mg/kg) or 15 days (10 mg/kg). Hence, a dimerization inhibitor for CSF-1R offers the advantage to not directly compete with the dramatically upregulated ligand for binding to the receptor in contrast to a ligand displacing antibody.

Example 12

In Vivo Efficacy Tumor Growth Inhibition of Anti-CSF-1R Antibodies in Breast Cancer BT20 Xenograft Tumor Cells in SCID Beige Mice The human breast cancer cell line BT-20 expresses human CSF-1R but lacks CSF-1 expression (Sapi, E. et al Cancer Res 59 (1999) 5578-5585). Since the mouse derived CSF-1 fails to activate human CSF-1R on the tumor cells recombinant human CSF-1 (Biomol, Hamburg, Germany) was supplemented via osmotic minipumps (ALZET, Cupertino, Calif.) providing a continuous CSF-1 infusion rate of 2 μg/day (Martin, T. A., Carcinogenesis 24 (2003) 1317-1323).

To directly compare the efficacy of an antibody interfering with dimerization of CSF-1R with a ligand displacing CSF-1R antibody we tested the chimeric anti-CSF-1R Mab 2F11 (antibody interfering with dimerization of CSF-1R) and 1.2.SM (ligand displacing CSF-1R antibody described in WO2009026303) in the BT-20 xenograft model.

SCID beige mice (Charles River, Salzfeld, Germany) were subcutaneously coinjected with 1×107 cells BT-20 cells (ATCC HTB-19) and 100 μl of Matrigel. Treatment of animals started at day of randomization at a mean tumor volume of 100 mm3. Mice are treated once weekly i.p. with the respective antibodies (see FIG. 4) in 20 mM Histidine, 140 mM NaCl pH 6.0 buffer. The tumor dimensions are measured by caliper beginning on the staging day and subsequently 2 times per week during the whole treatment period. Tumor volume is calculated according to NCI protocol (Tumor weight=1/2ab2, where "a" and "b" are the long and the short diameters of the tumor, respectively).

Figure 4:
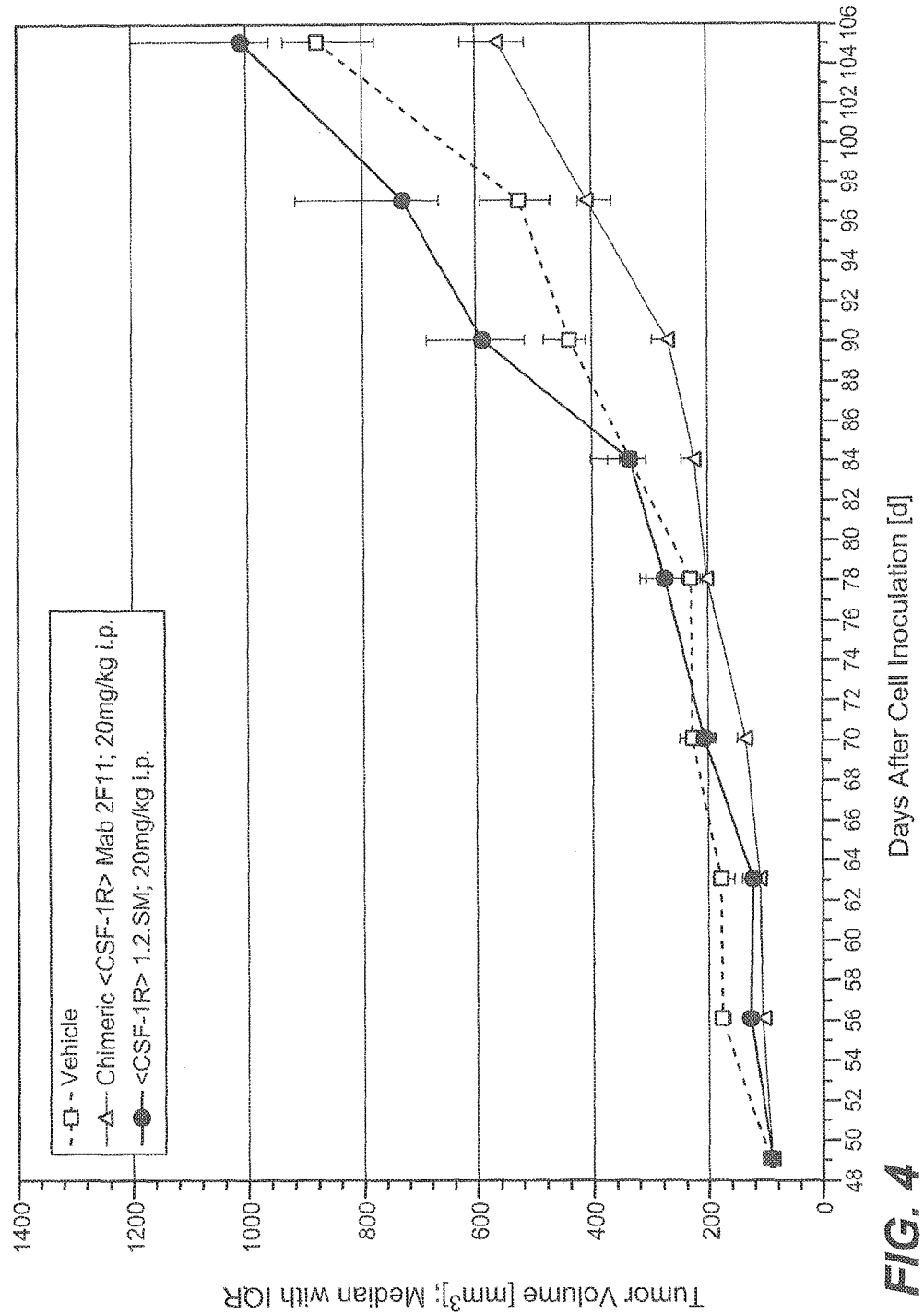

Tumor growth analysis is shown in FIG. 4. Inhibition of human CSF-1R on tumor cells with the chimeric anti-CSF-1R Mab 2F11 was statistically more efficacious in mediating tumor growth inhibition than anti-CSF-1R antibody 1.2.SM (CSF-1R antibody described in WO2009026303).

Although the foregoing, invention has been described in some detail by way of illustration and example for purposes of clarity of understanding, the descriptions and examples should not he construed as limiting the scope of the invention. The disclosures of all patents, patent applications, scientific references, and Genbank Accession Nos. cited herein are expressly incorporated by reference in their entirety for all puroposes as if each patent, patent application, scientific reference, and Genbank Accesion No. were specifically and individually incorporated by reference.

The invention claimed is:

1. An isolated antibody binding to human CSF-1R, wherein the antibody comprises a heavy chain variable domain and a light chain variable domain, and wherein the heavy chain variable domain comprises a CDR3 region comprising SEQ ID NO: 69, a CDR2 region comprising SEQ ID NO: 70, and a CDR1 region comprising SEQ ID NO: 71, and the light chain variable domain comprises a CDR3 region comprising SEQ ID NO:72, a CDR2 region comprising SEQ ID NO: 73, and a CDR1 region comprising SEQ ID NO: 74.

2. A pharmaceutical composition comprising an antibody according to claim 1.

3. The pharmaceutical composition according to claim 2, wherein said antibody is formulated in a pharmaceutically acceptable carrier.

4. The antibody according to claim 1, wherein the antibody is human IgG1 subclass or is of human IgG4 subclass.

5. The antibody according to claim 1, wherein the antibody is a chimeric, single chain, multispecific, or humanized antibody.

6. A pharmaceutical composition comprising an antibody according to claim 5.

7. The antibody according to claim 1, wherein the antibody is an antigen binding fragment.

8. A pharmaceutical composition comprising an antibody according to claim 7.

9. The antibody according to claim 1, wherein the antibody is a monoclonal antibody.

10. A pharmaceutical composition comprising an antibody according to claim 9.

11. An isolated antibody binding to human CSF-I R, wherein the antibody comprises a heavy chain variable domain and a light chain variable domain, and wherein the heavy chain variable domain comprises SEQ ID NO: 75 and the light chain variable domain comprises SEQ ID NO: 76.

12. A pharmaceutical composition comprising an antibody according to claim 11.

13. The pharmaceutical composition according to claim 12, wherein said antibody is formulated in a pharmaceutically acceptable carrier.

14. The antibody according to claim 11, wherein the antibody is human IgG1 subclass or is of human IgG4 subclass.

15. The antibody according to claim 11, wherein the antibody is a chimeric, single chain, multispecific, or humanized antibody.

16. A pharmaceutical composition comprising an antibody according to claim 15.

17. The antibody according to claim 11, wherein the antibody is an antigen binding fragment.

18. A pharmaceutical composition comprising an antibody according to claim 17.

19. The antibody according to claim 11, wherein the antibody is a monoclonal antibody.

20. A pharmaceutical composition comprising an antibody according to claim 19.

* * * * *

SEQUENCE LISTING

<160> NUMBER OF SEQ ID NOS: 84

<210> SEQ ID NO 1
<211> LENGTH: 8
<212> TYPE: PRT
<213> ORGANISM: Mus musculus

<400> SEQUENCE: 1

Asp Gln Arg Leu Tyr Phe Asp Val
1               5

<210> SEQ ID NO 2
<211> LENGTH: 16
<212> TYPE: PRT
<213> ORGANISM: Mus musculus

<400> SEQUENCE: 2

Val Ile Trp Thr Asp Gly Gly Thr Asn Tyr Asn Ser Pro Phe Met Ser
1               5                   10                  15

<210> SEQ ID NO 3
<211> LENGTH: 5
<212> TYPE: PRT
<213> ORGANISM: Mus musculus

<400> SEQUENCE: 3

Thr Tyr Asp Ile Ser
1               5

<210> SEQ ID NO 4
<211> LENGTH: 8
<212> TYPE: PRT
<213> ORGANISM: Mus musculus

<400> SEQUENCE: 4

Gly Gln Ser Phe Ser Tyr Pro Thr
1               5

<210> SEQ ID NO 5
<211> LENGTH: 7
<212> TYPE: PRT
<213> ORGANISM: Mus musculus

<400> SEQUENCE: 5

Gly Ala Ser Asn Arg Tyr Thr
1               5

<210> SEQ ID NO 6
<211> LENGTH: 11
<212> TYPE: PRT
<213> ORGANISM: Mus musculus

<400> SEQUENCE: 6

Lys Ala Ser Glu Asp Val Asn Thr Tyr Val Ser
1               5                   10

<210> SEQ ID NO 7
<211> LENGTH: 116
<212> TYPE: PRT
<213> ORGANISM: Mus musculus

<400> SEQUENCE: 7

Gln Val Gln Leu Lys Glu Ser Gly Pro Gly Leu Val Ala Pro Ser Gln
1               5                   10                  15

```
Ser Leu Ser Ile Thr Cys Thr Val Ser Gly Phe Ser Leu Thr Thr Tyr
             20                  25                  30

Asp Ile Ser Trp Ile Arg Gln Ser Pro Gly Lys Gly Leu Glu Trp Leu
             35                  40                  45

Gly Val Ile Trp Thr Asp Gly Gly Thr Asn Tyr Asn Ser Pro Phe Met
 50                  55                  60

Ser Arg Leu Ser Ile Arg Lys Asp Asn Ser Lys Ser Gln Val Phe Leu
 65                  70                  75                  80

Lys Met Asn Arg Leu Gln Thr Asp Asp Thr Ala Ile Tyr Tyr Cys Val
                 85                  90                  95

Arg Asp Gln Arg Leu Tyr Phe Asp Val Trp Gly Ala Gly Thr Thr Val
             100                 105                 110

Thr Val Ser Ser
         115

<210> SEQ ID NO 8
<211> LENGTH: 106
<212> TYPE: PRT
<213> ORGANISM: Mus musculus

<400> SEQUENCE: 8

Asn Ile Val Met Thr Gln Ser Pro Lys Ser Met Ser Met Ser Val Gly
 1               5                  10                  15

Glu Arg Val Thr Leu Asn Cys Lys Ala Ser Glu Asp Val Asn Thr Tyr
             20                  25                  30

Val Ser Trp Tyr Gln Gln Pro Glu Gln Ser Pro Lys Leu Leu Ile
             35                  40                  45

Tyr Gly Ala Ser Asn Arg Tyr Thr Gly Val Pro Asp Arg Phe Thr Gly
 50                  55                  60

Gly Gly Ser Thr Thr Asp Phe Thr Leu Thr Ile Ser Ser Val Gln Ala
 65                  70                  75                  80

Glu Asp Leu Ala Asp Tyr Phe Cys Gly Gln Ser Phe Ser Tyr Pro Thr
                 85                  90                  95

Phe Gly Thr Gly Thr Lys Leu Glu Ile Lys
             100                 105

<210> SEQ ID NO 9
<211> LENGTH: 7
<212> TYPE: PRT
<213> ORGANISM: Mus musculus

<400> SEQUENCE: 9

Asp Pro Arg Leu Tyr Phe Asp
 1               5

<210> SEQ ID NO 10
<211> LENGTH: 16
<212> TYPE: PRT
<213> ORGANISM: Mus musculus

<400> SEQUENCE: 10

Val Ile Trp Thr Gly Gly Thr Asn Tyr Asn Ser Gly Phe Met Ser
 1               5                  10                  15

<210> SEQ ID NO 11
<211> LENGTH: 5
<212> TYPE: PRT
<213> ORGANISM: Mus musculus

<400> SEQUENCE: 11
```

Ser Phe Asp Ile Ser
1               5

<210> SEQ ID NO 12
<211> LENGTH: 8
<212> TYPE: PRT
<213> ORGANISM: Mus musculus

<400> SEQUENCE: 12

Gly Gln Thr Phe Ser Tyr Pro Thr
1               5

<210> SEQ ID NO 13
<211> LENGTH: 7
<212> TYPE: PRT
<213> ORGANISM: Mus musculus

<400> SEQUENCE: 13

Gly Ala Ser Asn Arg Tyr Thr
1               5

<210> SEQ ID NO 14
<211> LENGTH: 11
<212> TYPE: PRT
<213> ORGANISM: Mus musculus

<400> SEQUENCE: 14

Lys Ala Ser Glu Asp Val Val Thr Tyr Val Ser
1               5                   10

<210> SEQ ID NO 15
<211> LENGTH: 116
<212> TYPE: PRT
<213> ORGANISM: Mus musculus

<400> SEQUENCE: 15

Gln Val Gln Leu Lys Glu Ser Gly Pro Gly Leu Val Ala Pro Ser Lys
1               5                   10                  15

Ser Leu Ser Ile Thr Cys Thr Val Ser Gly Ser Ser Leu Asp Ser Phe
            20                  25                  30

Asp Ile Ser Trp Ile Arg Gln Ser Pro Gly Lys Gly Leu Glu Trp Leu
        35                  40                  45

Gly Val Ile Trp Thr Gly Gly Thr Asn Tyr Asn Ser Gly Phe Met
    50                  55                  60

Ser Arg Leu Arg Ile Thr Lys Asp Asn Ser Lys Ser Gln Val Leu Leu
65                  70                  75                  80

Lys Met Asn Ser Leu Gln Ser Asp Asp Thr Ala Ile Tyr Tyr Cys Val
                85                  90                  95

Arg Asp Pro Arg Leu Tyr Phe Asp Val Trp Gly Ala Gly Thr Thr Val
            100                 105                 110

Thr Val Ser Ser
        115

<210> SEQ ID NO 16
<211> LENGTH: 106
<212> TYPE: PRT
<213> ORGANISM: Mus musculus

<400> SEQUENCE: 16

Asn Ile Val Met Thr Gln Ser Pro Lys Ser Met Ser Met Ser Val Gly
1               5                   10                  15

```
Glu Arg Val Thr Leu Ser Cys Lys Ala Ser Glu Asp Val Val Thr Tyr
            20                  25                  30

Val Ser Trp Tyr Gln Gln Lys Pro Asp Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr Tyr Cys Gly Gln Thr Phe Ser Tyr Pro Thr
                85                  90                  95

Phe Gly Thr Gly Thr Lys Leu Glu Ile Lys
            100                 105

<210> SEQ ID NO 17
<211> LENGTH: 8
<212> TYPE: PRT
<213> ORGANISM: Artificial
<220> FEATURE:
<223> OTHER INFORMATION: heavy chain CDR3, hMab 2F11-c11

<400> SEQUENCE: 17

Asp Gln Arg Leu Tyr Phe Asp Val
1               5

<210> SEQ ID NO 18
<211> LENGTH: 16
<212> TYPE: PRT
<213> ORGANISM: Artificial
<220> FEATURE:
<223> OTHER INFORMATION: heavy chain CDR2, hMab 2F11-c11

<400> SEQUENCE: 18

Val Ile Trp Thr Asp Gly Gly Thr Asn Tyr Asn Ser Pro Phe Met Ser
1               5                   10                  15

<210> SEQ ID NO 19
<211> LENGTH: 5
<212> TYPE: PRT
<213> ORGANISM: Artificial
<220> FEATURE:
<223> OTHER INFORMATION: heavy chain CDR1, hMab 2F11-c11

<400> SEQUENCE: 19

Thr Tyr Asp Ile Ser
1               5

<210> SEQ ID NO 20
<211> LENGTH: 8
<212> TYPE: PRT
<213> ORGANISM: Artificial
<220> FEATURE:
<223> OTHER INFORMATION: light chain CDR3, hMab 2F11-c11

<400> SEQUENCE: 20

Gly Gln Ser Phe Ser Tyr Pro Thr
1               5

<210> SEQ ID NO 21
<211> LENGTH: 7
<212> TYPE: PRT
<213> ORGANISM: Artificial
<220> FEATURE:
<223> OTHER INFORMATION: light chain CDR2, hMab 2F11-c11
```

```
<400> SEQUENCE: 21

Gly Ala Ser Asn Arg Tyr Thr
1               5

<210> SEQ ID NO 22
<211> LENGTH: 11
<212> TYPE: PRT
<213> ORGANISM: Artificial
<220> FEATURE:
<223> OTHER INFORMATION: light chain CDR1, hMab 2F11-c11

<400> SEQUENCE: 22

Arg Ala Ser Glu Asp Val Asn Thr Tyr Val Ser
1               5                   10

<210> SEQ ID NO 23
<211> LENGTH: 116
<212> TYPE: PRT
<213> ORGANISM: Artificial
<220> FEATURE:
<223> OTHER INFORMATION: heavy chain variable domain, hMab 2F11-c11

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Thr Tyr
            20                  25                  30

Asp Ile Ser Trp Ile Arg Gln Ala Pro Gly Gln Gly Leu Glu Trp Met
        35                  40                  45

Gly Val Ile Trp Thr Asp Gly Gly Thr Asn Tyr Asn Ser Pro Phe Met
    50                  55                  60

Ser Arg Val Thr Ile Thr Lys Asp Glu Ser Thr Ser Thr Ala Tyr Met
65                  70                  75                  80

Glu Leu Ser Ser Leu Arg Ser Glu Asp Thr Ala Val Tyr Tyr Cys Val
                85                  90                  95

Arg Asp Gln Arg Leu Tyr Phe Asp Val Trp Gly Gln Gly Thr Thr Val
            100                 105                 110

Thr Val Ser Ser
        115

<210> SEQ ID NO 24
<211> LENGTH: 106
<212> TYPE: PRT
<213> ORGANISM: Artificial
<220> FEATURE:
<223> OTHER INFORMATION: light chain variable domain, hMab 2F11-c11

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Phe Ser Tyr Pro Thr
                85                  90                  95
```

Phe Gly Gln Gly Thr Lys Leu Glu Ile Lys
            100                 105

<210> SEQ ID NO 25
<211> LENGTH: 8
<212> TYPE: PRT
<213> ORGANISM: Artificial
<220> FEATURE:
<223> OTHER INFORMATION: heavy chain CDR3, hMab 2F11-d8

<400> SEQUENCE: 25

Asp Gln Arg Leu Tyr Phe Asp Val
1               5

<210> SEQ ID NO 26
<211> LENGTH: 16
<212> TYPE: PRT
<213> ORGANISM: Artificial
<220> FEATURE:
<223> OTHER INFORMATION: heavy chain CDR2, hMab 2F11-d8

<400> SEQUENCE: 26

Val Ile Trp Thr Asp Gly Gly Ala Asn Tyr Ala Gln Lys Phe Gln Gly
1               5                   10                  15

<210> SEQ ID NO 27
<211> LENGTH: 5
<212> TYPE: PRT
<213> ORGANISM: Artificial
<220> FEATURE:
<223> OTHER INFORMATION: heavy chain CDR1, hMab 2F11-d8

<400> SEQUENCE: 27

Thr Tyr Asp Ile Ser
1               5

<210> SEQ ID NO 28
<211> LENGTH: 8
<212> TYPE: PRT
<213> ORGANISM: Artificial
<220> FEATURE:
<223> OTHER INFORMATION: light chain CDR3, hMab 2F11-d8

<400> SEQUENCE: 28

Gly Gln Ser Phe Ser Tyr Pro Thr
1               5

<210> SEQ ID NO 29
<211> LENGTH: 7
<212> TYPE: PRT
<213> ORGANISM: Artificial
<220> FEATURE:
<223> OTHER INFORMATION: light chain CDR2, hMab 2F11-d8

<400> SEQUENCE: 29

Gly Ala Ser Asn Arg Tyr Thr
1               5

<210> SEQ ID NO 30
<211> LENGTH: 11
<212> TYPE: PRT
<213> ORGANISM: Artificial
<220> FEATURE:
<223> OTHER INFORMATION: light chain CDR1, hMab 2F11-d8

<400> SEQUENCE: 30

Lys Ala Ser Glu Asp Val Asn Thr Tyr Val Ser
1               5                   10

<210> SEQ ID NO 31
<211> LENGTH: 116
<212> TYPE: PRT
<213> ORGANISM: Artificial
<220> FEATURE:
<223> OTHER INFORMATION: heavy chain variable domain, hMab 2F11-d8

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Thr Tyr
                20                  25                  30

Asp Ile Ser Trp Val Arg Gln Ala Pro Gly Gln Gly Leu Glu Trp Met
            35                  40                  45

Gly Val Ile Trp Thr Asp Gly Gly Ala Asn Tyr Ala Gln Lys Phe Gln
50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Asp Gln Arg Leu Tyr Phe Asp Val Trp Gly Gln Gly Thr Thr Val
            100                 105                 110

Thr Val Ser Ser
        115

<210> SEQ ID NO 32
<211> LENGTH: 106
<212> TYPE: PRT
<213> ORGANISM: Artificial
<220> FEATURE:
<223> OTHER INFORMATION: light chain variable domain, hMab 2F11-d8

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asp Val Asn Thr Tyr
                20                  25                  30

Val Ser Trp Tyr Gln Gln Lys Pro Gly Lys Ala Pro Lys Leu Leu Ile
            35                  40                  45

Tyr Gly Ala Ser Asn Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Phe Ser Tyr Pro Thr
                85                  90                  95

Phe Gly Gln Gly Thr Lys Leu Glu Ile Lys
            100                 105

<210> SEQ ID NO 33
<211> LENGTH: 8
<212> TYPE: PRT
<213> ORGANISM: Artificial
<220> FEATURE:
<223> OTHER INFORMATION: heavy chain CDR3, hMab 2F11-e7

<400> SEQUENCE: 33

Asp Gln Arg Leu Tyr Phe Asp Val

```
1               5

<210> SEQ ID NO 34
<211> LENGTH: 16
<212> TYPE: PRT
<213> ORGANISM: Artificial
<220> FEATURE:
<223> OTHER INFORMATION: heavy chain CDR2, hMab 2F11-e7

<400> SEQUENCE: 34

Val Ile Trp Thr Asp Gly Gly Thr Asn Tyr Ala Gln Lys Leu Gln Gly
1               5                   10                  15

<210> SEQ ID NO 35
<211> LENGTH: 5
<212> TYPE: PRT
<213> ORGANISM: Artificial
<220> FEATURE:
<223> OTHER INFORMATION: heavy chain CDR1, hMab 2F11-e7

<400> SEQUENCE: 35

Ser Tyr Asp Ile Ser
1               5

<210> SEQ ID NO 36
<211> LENGTH: 8
<212> TYPE: PRT
<213> ORGANISM: Artificial
<220> FEATURE:
<223> OTHER INFORMATION: light chain CDR3, hMab 2F11-e7

<400> SEQUENCE: 36

Gln Gln Ser Phe Ser Tyr Pro Thr
1               5

<210> SEQ ID NO 37
<211> LENGTH: 7
<212> TYPE: PRT
<213> ORGANISM: Artificial
<220> FEATURE:
<223> OTHER INFORMATION: light chain CDR2, hMab 2F11-e7

<400> SEQUENCE: 37

Ala Ala Ser Asn Arg Tyr Thr
1               5

<210> SEQ ID NO 38
<211> LENGTH: 11
<212> TYPE: PRT
<213> ORGANISM: Artificial
<220> FEATURE:
<223> OTHER INFORMATION: light chain CDR1, hMab 2F11-e7

<400> SEQUENCE: 38

Arg Ala Ser Glu Asp Val Asn Thr Tyr Val Ser
1               5                   10

<210> SEQ ID NO 39
<211> LENGTH: 116
<212> TYPE: PRT
<213> ORGANISM: Artificial
<220> FEATURE:
<223> OTHER INFORMATION: heavy chain variable domain, hMab 2F11-e7

<400> SEQUENCE: 39

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Asp Ile Ser Trp Val Arg Gln Ala Pro Gly Gln Gly Leu Glu Trp Met
            35                  40                  45

Gly Val Ile Trp Thr Asp Gly Gly Thr Asn Tyr Ala Gln Lys Leu Gln
 50                  55                  60

Gly Arg Val Thr Met Thr Thr Asp Thr Ser Thr Ser Thr Ala Tyr Met
 65                  70                  75                  80

Glu Leu Arg Ser Leu Arg Ser Asp Asp Thr Ala Val Tyr Tyr Cys Ala
            85                  90                  95

Arg Asp Gln Arg Leu Tyr Phe Asp Val Trp Gly Gln Gly Thr Thr Val
            100                 105                 110

Thr Val Ser Ser
        115
```

<210> SEQ ID NO 40
<211> LENGTH: 106
<212> TYPE: PRT
<213> ORGANISM: Artificial
<220> FEATURE:
<223> OTHER INFORMATION: light chain variable domain, hMab 2F11-e7

<400> SEQUENCE: 40

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
            20                  25                  30

Val Ser Trp Tyr Gln Gln Lys Pro Gly Lys Ala Pro Lys Leu Leu Ile
            35                  40                  45

Tyr Ala Ala Ser Asn Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Phe Ser Tyr Pro Thr
            85                  90                  95

Phe Gly Gln Gly Thr Lys Leu Glu Ile Lys
            100                 105
```

<210> SEQ ID NO 41
<211> LENGTH: 8
<212> TYPE: PRT
<213> ORGANISM: Artificial
<220> FEATURE:
<223> OTHER INFORMATION: heavy chain CDR3, hMab 2F11-f12

<400> SEQUENCE: 41

```
Asp Gln Arg Leu Tyr Phe Asp Val
1               5
```

<210> SEQ ID NO 42
<211> LENGTH: 16
<212> TYPE: PRT
<213> ORGANISM: Artificial
<220> FEATURE:
<223> OTHER INFORMATION: heavy chain CDR2, hMab 2F11-f12

<400> SEQUENCE: 42

```
Val Ile Trp Thr Asp Gly Gly Thr Asn Tyr Asn Ser Pro Phe Met Ser
1               5                   10                  15
```

```
<210> SEQ ID NO 43
<211> LENGTH: 5
<212> TYPE: PRT
<213> ORGANISM: Artificial
<220> FEATURE:
<223> OTHER INFORMATION: heavy chain CDR1, hMab 2F11-f12

<400> SEQUENCE: 43

Thr Tyr Asp Ile Ser
1               5

<210> SEQ ID NO 44
<211> LENGTH: 8
<212> TYPE: PRT
<213> ORGANISM: Artificial
<220> FEATURE:
<223> OTHER INFORMATION: light chain CDR3, hMab 2F11-f12

<400> SEQUENCE: 44

Gly Gln Ser Phe Ser Tyr Pro Thr
1               5

<210> SEQ ID NO 45
<211> LENGTH: 7
<212> TYPE: PRT
<213> ORGANISM: Artificial
<220> FEATURE:
<223> OTHER INFORMATION: light chain CDR2, hMab 2F11-f12

<400> SEQUENCE: 45

Gly Ala Ser Ser Leu Gln Ser
1               5

<210> SEQ ID NO 46
<211> LENGTH: 11
<212> TYPE: PRT
<213> ORGANISM: Artificial
<220> FEATURE:
<223> OTHER INFORMATION: light chain CDR1, hMab 2F11-f12

<400> SEQUENCE: 46

Arg Ala Ser Glu Asp Val Asn Thr Tyr Val Ser
1               5                   10

<210> SEQ ID NO 47
<211> LENGTH: 116
<212> TYPE: PRT
<213> ORGANISM: Artificial
<220> FEATURE:
<223> OTHER INFORMATION: heavy chain variable domain, hMab 2F11-f12

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ser Leu Thr Thr Tyr
            20                  25                  30

Asp Ile Ser Trp Val Arg Gln Ala Pro Gly Gln Gly Leu Glu Trp Met
        35                  40                  45

Gly Val Ile Trp Thr Asp Gly Gly Thr Asn Tyr Asn Ser Pro Phe Met
    50                  55                  60

Ser Arg Val Thr Ile Thr Lys Asp Glu Ser Thr Ser Thr Ala Tyr Met
65                  70                  75                  80

Glu Leu Ser Ser Leu Arg Ser Glu Asp Thr Ala Val Tyr Cys Val
                85                  90                  95
```

Arg Asp Gln Arg Leu Tyr Phe Asp Val Trp Gly Gln Gly Thr Thr Val
            100                 105                 110

Thr Val Ser Ser
        115

<210> SEQ ID NO 48
<211> LENGTH: 106
<212> TYPE: PRT
<213> ORGANISM: Artificial
<220> FEATURE:
<223> OTHER INFORMATION: light chain variable domain, hMab 2F11-f12

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
            20                  25                  30

Val Ser Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Phe Ser Tyr Pro Thr
                85                  90                  95

Phe Gly Gln Gly Thr Lys Leu Glu Ile Lys
            100                 105

<210> SEQ ID NO 49
<211> LENGTH: 8
<212> TYPE: PRT
<213> ORGANISM: Artificial
<220> FEATURE:
<223> OTHER INFORMATION: heavy chain CDR3, hMab 2F11-g1

<400> SEQUENCE: 49

Asp Gln Arg Leu Tyr Phe Asp Val
1               5

<210> SEQ ID NO 50
<211> LENGTH: 16
<212> TYPE: PRT
<213> ORGANISM: Artificial
<220> FEATURE:
<223> OTHER INFORMATION: heavy chain CDR2, hMab 2F11-g1

<400> SEQUENCE: 50

Val Ile Trp Thr Asp Gly Gly Thr Asn Tyr Asn Ser Pro Leu Lys Ser
1               5                   10                  15

<210> SEQ ID NO 51
<211> LENGTH: 5
<212> TYPE: PRT
<213> ORGANISM: Artificial
<220> FEATURE:
<223> OTHER INFORMATION: heavy chain CDR1, hMab 2F11-g1

<400> SEQUENCE: 51

Thr Tyr Asp Ile Ser
1               5

<210> SEQ ID NO 52

<210> SEQ ID NO 52
<211> LENGTH: 8
<212> TYPE: PRT
<213> ORGANISM: Artificial
<220> FEATURE:
<223> OTHER INFORMATION: light chain CDR3, hMab 2F11-g1

<400> SEQUENCE: 52

Gly Gln Ser Phe Ser Tyr Pro Thr
1               5

<210> SEQ ID NO 53
<211> LENGTH: 7
<212> TYPE: PRT
<213> ORGANISM: Artificial
<220> FEATURE:
<223> OTHER INFORMATION: light chain CDR2, hMab 2F11-g1

<400> SEQUENCE: 53

Gly Ala Ser Ser Arg Ala Thr
1               5

<210> SEQ ID NO 54
<211> LENGTH: 11
<212> TYPE: PRT
<213> ORGANISM: Artificial
<220> FEATURE:
<223> OTHER INFORMATION: light chain CDR1, hMab 2F11-g1

<400> SEQUENCE: 54

Arg Ala Ser Glu Asp Val Asn Thr Tyr Leu Ala
1               5                   10

<210> SEQ ID NO 55
<211> LENGTH: 116
<212> TYPE: PRT
<213> ORGANISM: Artificial
<220> FEATURE:
<223> OTHER INFORMATION: heavy chain variable domain, hMab 2F11-g1

<400> SEQUENCE: 55

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Asp Ile Ser Trp Ile Arg Gln Pro Pro Gly Lys Gly Leu Glu Trp Ile
        35                  40                  45

Gly Val Ile Trp Thr Asp Gly Gly Thr Asn Tyr Asn Ser Pro Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gln Arg Leu Tyr Phe Asp Val Trp Gly Gln Gly Thr Thr Val
            100                 105                 110

Thr Val Ser Ser
        115

<210> SEQ ID NO 56
<211> LENGTH: 106
<212> TYPE: PRT
<213> ORGANISM: Artificial
<220> FEATURE:
<223> OTHER INFORMATION: light chain variable domain, hMab 2F11-g1

<400> SEQUENCE: 56

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Glu Asp Val Asn Thr Tyr
            20                  25                  30

Leu Ala Trp Tyr Gln Gln Lys Pro Gly Gln Ala Pro Arg Leu Leu Ile
        35                  40                  45

Tyr Gly Ala Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gly Gln Ser Phe Ser Tyr Pro Thr
                85                  90                  95

Phe Gly Gln Gly Thr Lys Leu Glu Ile Lys
            100                 105

<210> SEQ ID NO 57
<211> LENGTH: 107
<212> TYPE: PRT
<213> ORGANISM: Homo sapiens

<400> SEQUENCE: 57

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 58
<211> LENGTH: 330
<212> TYPE: PRT
<213> ORGANISM: Homo sapiens

<400> SEQUENCE: 58

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys

```
                100             105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
            210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 59
<211> LENGTH: 330
<212> TYPE: PRT
<213> ORGANISM: Artificial
<220> FEATURE:
<223> OTHER INFORMATION: human heavy chain constant region derived from
      IgG1 mutated on L234A and L235A

<400> SEQUENCE: 59

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
                100                 105                 110
Pro Ala Pro Glu Ala Ala Gly Gly Pro Ser Val Phe Leu Phe Pro Pro
            115                 120                 125
```

```
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 60
<211> LENGTH: 327
<212> TYPE: PRT
<213> ORGANISM: Homo sapiens

<400> SEQUENCE: 60

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
                100                 105                 110
Glu Phe Leu Gly Gly Pro Ser Val Phe Leu Phe Pro Pro Lys Pro Lys
            115                 120                 125
Asp Thr Leu Met Ile Ser Arg Thr Pro Glu Val Thr Cys Val Val Val
        130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
```

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 61
<211> LENGTH: 327
<212> TYPE: PRT
<213> ORGANISM: Artificial
<220> FEATURE:
<223> OTHER INFORMATION: human heavy chain constant region derived from
      IgG4 mutated onS228P

<400> SEQUENCE: 61

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu

-continued

```
                195                 200                 205
Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 62
<211> LENGTH: 972
<212> TYPE: PRT
<213> ORGANISM: Homo sapiens

<400> SEQUENCE: 62

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240
```

```
Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
        260                 265                 270

Ala Gly Asn Tyr Ser Cys Val Ala Ser Asn Val Gln Gly Lys His Ser
    275                 280                 285

Thr Ser Met Phe Phe Arg Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
        515                 520                 525

Leu Leu Leu Leu Leu Leu Leu Leu Tyr Lys Tyr Lys Gln Lys Pro
    530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
    610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
```

```
                    660                 665                 670
Asn Phe Leu Arg Arg Lys Ala Glu Ala Met Leu Gly Pro Ser Leu Ser
            675                 680                 685

Pro Gly Gln Asp Pro Glu Gly Val Asp Tyr Lys Asn Ile His Leu
        690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
        755                 760                 765

Leu Ala Ser Lys Asn Cys Ile His Arg Asp Val Ala Ala Arg Asn Val
    770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
    850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
        915                 920                 925

Ser Ser Arg Ser Gly Gly Ser Gly Ser Ser Ser Glu Leu Glu Glu
    930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970

<210> SEQ ID NO 63
<211> LENGTH: 972
<212> TYPE: PRT
<213> ORGANISM: Artificial
<220> FEATURE:
<223> OTHER INFORMATION: mutant CSF-1R L301S Y969F

<400> SEQUENCE: 63

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val

```
                50                  55                  60
Ser Ser Ser Ile Leu Ser Thr Asn Asn Ala Thr Phe Gln Asn Thr Gly
 65                  70                  75                  80

Thr Tyr Arg Cys Thr Glu Pro Gly Asp Pro Leu Gly Gly Ser Ala Ala
                 85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
                115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
                180                 185                 190

Leu Lys Val Gln Lys Val Ile Pro Gly Pro Ala Leu Thr Leu Val
                195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
                275                 280                 285

Thr Ser Met Phe Phe Arg Val Val Glu Ser Ala Tyr Ser Asn Leu Ser
                290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
                355                 360                 365

Pro Arg Leu Lys Pro Ser Glu Ala Gly Arg Tyr Ser Phe Leu Ala Arg
370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
                420                 425                 430

Gln Cys Ser Gly His Thr Asp Arg Cys Asp Glu Ala Gln Val Leu Gln
                435                 440                 445

Val Trp Asp Asp Pro Tyr Pro Glu Val Leu Ser Gln Glu Pro Phe His
                450                 455                 460

Lys Val Thr Val Gln Ser Leu Leu Thr Val Glu Thr Leu Glu His Asn
465                 470                 475                 480
```

```
Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
        515                 520                 525

Leu Leu Leu Leu Leu Leu Leu Leu Tyr Lys Tyr Lys Gln Lys Pro
    530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
    610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
        675                 680                 685

Pro Gly Gln Asp Pro Glu Gly Gly Val Asp Tyr Lys Asn Ile His Leu
    690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
        755                 760                 765

Leu Ala Ser Lys Asn Cys Ile His Arg Asp Val Ala Ala Arg Asn Val
    770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
    850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895
```

```
Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
        915                 920                 925

Ser Ser Arg Ser Gly Gly Ser Gly Ser Ser Ser Glu Leu Glu Glu
    930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Phe Gln Phe Cys
                965                 970

<210> SEQ ID NO 64
<211> LENGTH: 493
<212> TYPE: PRT
<213> ORGANISM: Artificial
<220> FEATURE:
<223> OTHER INFORMATION: human CSF-1R Extracellular Domain

<400> SEQUENCE: 64

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
            85                  90                  95

Val Val Phe Glu Asp Gln Asp Ala Leu Leu Pro Cys Leu Leu Thr Asp
        100                 105                 110

Pro Val Leu Glu Ala Gly Val Ser Leu Val Arg Val Arg Gly Arg Pro
    115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
            165                 170                 175

Gln Lys Val Ile Pro Gly Pro Pro Ala Leu Thr Leu Val Pro Ala Glu
        180                 185                 190

Leu Val Arg Ile Arg Gly Glu Ala Ala Gln Ile Val Cys Ser Ala Ser
    195                 200                 205

Ser Val Asp Val Asn Phe Asp Val Phe Leu Gln His Asn Asn Thr Lys
210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
            245                 250                 255

Tyr Ser Cys Val Ala Ser Asn Val Gln Gly Lys His Ser Thr Ser Met
        260                 265                 270

Phe Phe Arg Val Val Glu Ser Ala Tyr Leu Asn Leu Ser Ser Glu Gln
    275                 280                 285
```

Asn Leu Ile Gln Glu Val Thr Val Gly Gly Leu Asn Leu Lys Val
290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Pro Lys Leu Ala Asn Ala Thr
            325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365

Gly Trp Arg Ala Leu Thr Phe Glu Leu Thr Leu Arg Tyr Pro Pro Glu
370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
            405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
        435                 440                 445

Val Gln Ser Leu Leu Thr Val Glu Thr Leu Glu His Asn Gln Thr Tyr
450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu
            485                 490

<210> SEQ ID NO 65
<211> LENGTH: 388
<212> TYPE: PRT
<213> ORGANISM: Artificial
<220> FEATURE:
<223> OTHER INFORMATION: human CSF-1R fragment delD4

<400> SEQUENCE: 65

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

```
Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Tyr Pro Pro Glu Val Ser Val Ile Trp Thr Phe Ile Asn
        275                 280                 285

Gly Ser Gly Thr Leu Leu Cys Ala Ala Ser Gly Tyr Pro Gln Pro Asn
    290                 295                 300

Val Thr Trp Leu Gln Cys Ser Gly His Thr Asp Arg Cys Asp Glu Ala
305                 310                 315                 320

Gln Val Leu Gln Val Trp Asp Asp Pro Tyr Pro Glu Val Leu Ser Gln
                325                 330                 335

Glu Pro Phe His Lys Val Thr Val Gln Ser Leu Leu Thr Val Glu Thr
            340                 345                 350

Leu Glu His Asn Gln Thr Tyr Glu Cys Arg Ala His Asn Ser Val Gly
        355                 360                 365

Ser Gly Ser Trp Ala Phe Ile Pro Ile Ser Ala Gly Ala His Thr His
    370                 375                 380

Pro Pro Asp Glu
385

<210> SEQ ID NO 66
<211> LENGTH: 292
<212> TYPE: PRT
<213> ORGANISM: Artificial
<220> FEATURE:
<223> OTHER INFORMATION: human CSF-1R fragment D1-D3

<400> SEQUENCE: 66

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125
```

-continued

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
            165                 170                 175

Gln Lys Val Ile Pro Gly Pro Pro Ala Leu Thr Leu Val Pro Ala Glu
        180                 185                 190

Leu Val Arg Ile Arg Gly Glu Ala Ala Gln Ile Val Cys Ser Ala Ser
    195                 200                 205

Ser Val Asp Val Asn Phe Asp Val Phe Leu Gln His Asn Asn Thr Lys
210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
            245                 250                 255

Tyr Ser Cys Val Ala Ser Asn Val Gln Gly Lys His Ser Thr Ser Met
        260                 265                 270

Phe Phe Arg Val Val Glu Ser Ala Tyr Leu Asn Leu Ser Ser Glu Gln
    275                 280                 285

Asn Leu Ile Gln
    290

<210> SEQ ID NO 67
<211> LENGTH: 21
<212> TYPE: PRT
<213> ORGANISM: Artificial
<220> FEATURE:
<223> OTHER INFORMATION: signal peptide

<400> SEQUENCE: 67

Met Gly Ser Gly Pro Gly Val Leu Leu Leu Leu Val Ala Thr Ala
1               5                   10                  15

Trp His Gly Gln Gly
            20

<210> SEQ ID NO 68
<211> LENGTH: 36
<212> TYPE: DNA
<213> ORGANISM: Artificial
<220> FEATURE:
<223> OTHER INFORMATION: Primer

<400> SEQUENCE: 68
cacctccatg ttcttccggt acccccaga ggtaag                                  36

<210> SEQ ID NO 69
<211> LENGTH: 8
<212> TYPE: PRT
<213> ORGANISM: Mus musculus

<400> SEQUENCE: 69

Asp Leu Arg Leu Tyr Phe Asp Val
1               5

<210> SEQ ID NO 70
<211> LENGTH: 16
<212> TYPE: PRT
<213> ORGANISM: Mus musculus

<400> SEQUENCE: 70

```
Val Ile Trp Ser Gly Gly Thr Asn Tyr Asn Ser Pro Phe Met Ser
1               5                   10                  15
```

<210> SEQ ID NO 71
<211> LENGTH: 10
<212> TYPE: PRT
<213> ORGANISM: Mus musculus

<400> SEQUENCE: 71

```
Gly Phe Ser Leu Thr Ser Tyr Asp Ile Ser
1               5                   10
```

<210> SEQ ID NO 72
<211> LENGTH: 8
<212> TYPE: PRT
<213> ORGANISM: Mus musculus

<400> SEQUENCE: 72

```
Gly Gln Ser Phe Thr Tyr Pro Thr
1               5
```

<210> SEQ ID NO 73
<211> LENGTH: 7
<212> TYPE: PRT
<213> ORGANISM: Mus musculus

<400> SEQUENCE: 73

```
Gly Ser Ser Asn Arg Tyr Thr
1               5
```

<210> SEQ ID NO 74
<211> LENGTH: 11
<212> TYPE: PRT
<213> ORGANISM: Mus musculus

<400> SEQUENCE: 74

```
Lys Ala Ser Glu Asp Val Gly Thr Tyr Val Ser
1               5                   10
```

<210> SEQ ID NO 75
<211> LENGTH: 116
<212> TYPE: PRT
<213> ORGANISM: Mus musculus

<400> SEQUENCE: 75

```
Arg Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
                20                  25                  30

Asp Ile Ser Trp Ile Arg Gln Ser Pro Gly Lys Gly Leu Glu Trp Leu
            35                  40                  45

Gly Val Ile Trp Ser Gly Gly Gly Thr Asn Tyr Asn Ser Pro Phe Met
        50                  55                  60

Ser Arg Leu Arg Ile Ser Lys Asp Asp Ser Arg Ser Gln Val Phe Leu
65                  70                  75                  80

Lys Val Asn Arg Leu Gln Thr Asp Asp Thr Ala Ile Tyr Tyr Cys Val
                85                  90                  95

Arg Asp Leu Arg Leu Tyr Phe Asp Val Trp Gly Ala Gly Thr Thr Val
                100                 105                 110

Thr Val Ser Ser
            115
```

```
<210> SEQ ID NO 76
<211> LENGTH: 106
<212> TYPE: PRT
<213> ORGANISM: Mus musculus

<400> SEQUENCE: 76

Lys Ile Val Met Thr Gln Ser Pro Lys Ser Met Ser Val Ser Val Gly
1               5                   10                  15

Glu Arg Val Ser Leu Ser Cys Lys Ala Ser Glu Asp Val Gly Thr Tyr
            20                  25                  30

Val Ser Trp Tyr Gln Gln Lys Pro Glu Gln Ser Pro Lys Leu Leu Ile
        35                  40                  45

Tyr Gly Ser Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr Ser Cys Gly Gln Ser Phe Thr Tyr Pro Thr
                85                  90                  95

Phe Gly Thr Gly Thr Lys Leu Glu Ile Lys
            100                 105

<210> SEQ ID NO 77
<211> LENGTH: 8
<212> TYPE: PRT
<213> ORGANISM: Mus musculus

<400> SEQUENCE: 77

Asp Pro Arg Leu Tyr Phe Asp Val
1               5

<210> SEQ ID NO 78
<211> LENGTH: 16
<212> TYPE: PRT
<213> ORGANISM: Mus musculus

<400> SEQUENCE: 78

Val Ile Trp Thr Gly Gly Thr Asn Tyr Asn Ser Gly Phe Met Ser
1               5                   10                  15

<210> SEQ ID NO 79
<211> LENGTH: 10
<212> TYPE: PRT
<213> ORGANISM: Mus musculus

<400> SEQUENCE: 79

Gly Ser Ser Leu Asp Ser Phe Asp Ile Ser
1               5                   10

<210> SEQ ID NO 80
<211> LENGTH: 8
<212> TYPE: PRT
<213> ORGANISM: Mus musculus

<400> SEQUENCE: 80

Gly Gln Thr Phe Ser Tyr Pro Thr
1               5

<210> SEQ ID NO 81
<211> LENGTH: 7
<212> TYPE: PRT
<213> ORGANISM: Mus musculus
```

```
<400> SEQUENCE: 81

Gly Ala Ser Asn Arg Tyr Thr
1               5

<210> SEQ ID NO 82
<211> LENGTH: 11
<212> TYPE: PRT
<213> ORGANISM: Mus musculus

<400> SEQUENCE: 82

Lys Ala Ser Glu Asp Val Val Thr Tyr Val Ser
1               5                   10

<210> SEQ ID NO 83
<211> LENGTH: 116
<212> TYPE: PRT
<213> ORGANISM: Mus musculus

<400> SEQUENCE: 83

Gln Val Gln Leu Lys Glu Ser Gly Pro Gly Leu Val Ala Pro Ser Lys
1               5                   10                  15

Ser Leu Ser Ile Thr Cys Thr Val Ser Gly Ser Ser Leu Asp Ser Phe
            20                  25                  30

Asp Ile Ser Trp Ile Arg Gln Pro Pro Gly Lys Gly Leu Glu Trp Leu
        35                  40                  45

Gly Val Ile Trp Thr Gly Gly Thr Asn Tyr Asn Ser Gly Phe Met
    50                  55                  60

Ser Arg Leu Arg Ile Ser Lys Asp Asn Ser Lys Ser Gln Val Phe Leu
65                  70                  75                  80

Lys Met Ser Ser Leu Gln Ser Asp Asp Thr Ala Ile Tyr Tyr Cys Val
                85                  90                  95

Arg Asp Pro Arg Leu Tyr Phe Asp Val Trp Gly Ala Gly Thr Thr Val
            100                 105                 110

Thr Val Ser Ser
        115

<210> SEQ ID NO 84
<211> LENGTH: 106
<212> TYPE: PRT
<213> ORGANISM: Mus musculus

<400> SEQUENCE: 84

Asn Ile Val Met Thr Gln Ser Pro Lys Ser Met Ser Met Ser Val Gly
1               5                   10                  15

Glu Arg Val Thr Leu Ser Cys Lys Ala Ser Glu Asp Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Ile Gln Ala
65                  70                  75                  80

Glu Asp Leu Ala Asp Tyr Tyr Cys Gly Gln Thr Phe Ser Tyr Pro Thr
                85                  90                  95

Phe Gly Thr Gly Thr Lys Leu Glu Ile Lys
            100                 105
```